US010967000B2

(12) United States Patent
Kim

(10) Patent No.: US 10,967,000 B2
(45) Date of Patent: Apr. 6, 2021

(54) CELL-PENETRATING PEPTIDE, CONJUGATE COMPRISING SAME AND COMPOSITION COMPRISING SAME

(71) Applicants: GemVax & KAEL Co., Ltd., Daejeon (KR); Sang Jae Kim, Seoul (KR)

(72) Inventor: Sang Jae Kim, Seoul (KR)

(73) Assignee: Gemvax & Kael Co., Ltd., Daejon (KR)

(*) Notice: Subject to any disclaimer, the term of this patent is extended or adjusted under 35 U.S.C. 154(b) by 942 days.

(21) Appl. No.: 14/413,732

(22) PCT Filed: Jul. 11, 2013

(86) PCT No.: PCT/KR2013/006218
§ 371 (c)(1),
(2) Date: Nov. 10, 2015

(87) PCT Pub. No.: WO2014/010971
PCT Pub. Date: Jan. 16, 2014

(65) Prior Publication Data
US 2016/0151512 A1 Jun. 2, 2016

(30) Foreign Application Priority Data

Jul. 11, 2012 (KR) .................. 10-2012-0075444
Sep. 19, 2012 (KR) .................. 10-2012-0104173
Sep. 28, 2012 (KR) .................. 10-2012-0109207
Feb. 18, 2013 (KR) .................. 10-2013-0017046
Apr. 19, 2013 (KR) .................. 10-2013-0043635

(51) Int. Cl.
| C07K 7/08 | (2006.01) |
| A61K 31/711 | (2006.01) |
| A61K 49/00 | (2006.01) |
| A61K 47/64 | (2017.01) |
| A61K 31/713 | (2006.01) |
| A61K 48/00 | (2006.01) |
| A61K 49/14 | (2006.01) |
| A61K 38/00 | (2006.01) |

(52) U.S. Cl.
CPC .......... *A61K 31/711* (2013.01); *A61K 31/713* (2013.01); *A61K 47/64* (2017.08); *A61K 48/0041* (2013.01); *A61K 49/0047* (2013.01); *A61K 49/0056* (2013.01); *A61K 49/14* (2013.01); *C07K 7/08* (2013.01); *A61K 38/00* (2013.01)

(58) Field of Classification Search
CPC ............. A61K 47/48246; A61K 47/64; A61K 31/711; A61K 31/713; A61K 48/0041; A61K 49/0047; A61K 49/0056; A61K 49/14; C07K 7/08
See application file for complete search history.

(56) References Cited

U.S. PATENT DOCUMENTS

| 5,885,782 A * | 3/1999 | Edwards ................ A01N 37/46 435/7.1 |
| 6,967,211 B2 | 11/2005 | Inoue |
| 7,030,211 B1 * | 4/2006 | Gaudernack ............ A61P 35/02 530/326 |
| 7,786,084 B2 | 8/2010 | Benner et al. |
| 7,794,723 B2 | 9/2010 | Gaudernack et al. |
| 8,828,403 B2 | 9/2014 | Filaci et al. |
| 8,933,197 B2 | 1/2015 | Bogin et al. |
| 9,023,987 B2 | 5/2015 | Chung et al. |
| 9,540,419 B2 | 1/2017 | Kim et al. |
| 9,572,858 B2 | 2/2017 | Kim et al. |
| 2002/0042401 A1 | 4/2002 | Ferguson et al. |
| 2003/0027769 A1 | 2/2003 | Scialdone et al. |
| 2003/0143228 A1 | 7/2003 | Chen et al. |
| 2006/0106196 A1 | 5/2006 | Gaudernack et al. |
| 2007/0190561 A1 | 8/2007 | Morin et al. |
| 2008/0025986 A1 | 1/2008 | Ozes et al. |
| 2009/0136917 A1 | 5/2009 | Szalay et al. |
| 2009/0186802 A1 | 7/2009 | Alluis et al. |
| 2009/0215852 A1 | 8/2009 | Bascomb et al. |
| 2010/0003229 A1 | 1/2010 | Santos |
| 2011/0135692 A1 | 6/2011 | Filaci et al. |
| 2011/0150873 A1 | 6/2011 | Grainger |
| 2011/0183925 A1 | 7/2011 | Sato et al. |
| 2012/0053134 A1 | 3/2012 | Jung et al. |
| 2012/0065124 A1 | 3/2012 | Morishita et al. |
| 2012/0208755 A1 | 8/2012 | Leung |

(Continued)

FOREIGN PATENT DOCUMENTS

| CN | 1313773 A | 9/2001 |
| EP | 1020190 A3 | 10/2000 |

(Continued)

OTHER PUBLICATIONS

Du et al (J. Peptide Res., 1998, 51, pp. 235-243).*
Schwarze et al (Science, 1999, 285, pp. 1569-1572).*
Kalnins et al (The EMBO Journal, 1983, 2, pp. 593-597).*
Rudinger (Peptide Hormones, JA Parsons, Ed., 1976, pp. 1-7).*
SIGMA peptide design, 2004, 2 pages.*
Berendsen (Science, 1998, 282, pp. 642-643).*
Voet & Voet, Biochemistry, 2nd edition, 1995, pp. 234-241.*
Obesity-Merck Manual document 2014, (pp. 1-9, from http://www.merckmanuals.com/professional/nutritional_disorders/obesity_and_the_metab . . . ).*

(Continued)

Primary Examiner — Larry D Riggs, II
Assistant Examiner — Joseph Fischer
(74) *Attorney, Agent, or Firm* — Clark & Elbing LLP

(57) ABSTRACT

The present invention relates to a conjugate of cell penetrating peptide and an active ingredient; and its use. Specifically, a conjugate including a cell penetrating peptide which is a peptide comprising amino acid sequence of SEQ ID NO:1, a fragment of any one sequence of SEQ ID NO:1, or a peptide having above 80% homology with the above-mentioned sequence; and a composition comprising the same are disclosed.

16 Claims, 48 Drawing Sheets

Specification includes a Sequence Listing.

(56) References Cited

U.S. PATENT DOCUMENTS

| | | |
|---|---|---|
| 2012/0277290 A1 | 11/2012 | Collard et al. |
| 2013/0129760 A1 | 5/2013 | Gaudernack et al. |
| 2013/0230591 A1 | 9/2013 | Fellous et al. |
| 2015/0099692 A1 | 4/2015 | Kim et al. |
| 2015/0099693 A1 | 4/2015 | Kim et al. |
| 2015/0175978 A1 | 6/2015 | Kim |
| 2015/0307859 A1 | 10/2015 | Kim |
| 2015/0343095 A1 | 12/2015 | Kim |
| 2015/0353903 A1 | 12/2015 | Kim |
| 2016/0002613 A1 | 1/2016 | Kim |
| 2016/0008438 A1 | 1/2016 | Kim |
| 2016/0082089 A1 | 3/2016 | Kim |
| 2016/0120966 A1 | 5/2016 | Kim |
| 2016/0137695 A1 | 5/2016 | Kim |
| 2016/0250279 A1 | 9/2016 | Kim et al. |
| 2016/0296604 A1 | 10/2016 | Kim |
| 2016/0375091 A1 | 12/2016 | Kim |
| 2017/0028035 A1 | 2/2017 | Kim |
| 2017/0058001 A1 | 3/2017 | Kim |
| 2017/0081376 A1 | 3/2017 | Kim et al. |
| 2017/0128557 A1 | 5/2017 | Kim et al. |
| 2017/0143806 A1 | 5/2017 | Kim et al. |
| 2017/0275603 A1 | 9/2017 | Kim et al. |
| 2017/0360870 A1 | 12/2017 | Kim |

FOREIGN PATENT DOCUMENTS

| | | | |
|---|---|---|---|
| EP | 1093381 B2 | 7/2009 | |
| EP | 1817337 B1 | 1/2011 | |
| JP | 2002/520293 A | 7/2002 | |
| JP | 2002622373 A | 7/2002 | |
| JP | 2010-252810 | * 11/2010 | |
| JP | 2010252810 A | 11/2010 | |
| JP | 2011515498 A | 5/2011 | |
| JP | 2012500279 A | 1/2012 | |
| JP | 2012526524 A | 11/2012 | |
| JP | 5577472 B2 | 8/2014 | |
| KR | 19930001915 A | 2/1993 | |
| KR | 20010012613 A | 2/2001 | |
| KR | 20010020601 A | 3/2001 | |
| KR | 20040015087 A | 2/2004 | |
| KR | 20040045400 A | 6/2004 | |
| KR | 20040107492 A | 12/2004 | |
| KR | 20050020987 A | 3/2005 | |
| KR | 20050040517 A | 5/2005 | |
| KR | 20060065588 A | 6/2006 | |
| KR | 20060109903 A | 10/2006 | |
| KR | 20070083218 A | 8/2007 | |
| KR | 20080084818 A | 9/2008 | |
| KR | 20090033878 A | 4/2009 | |
| KR | 20090103957 A | 10/2009 | |
| KR | 20100058541 A | 6/2010 | |
| KR | 10-2010-0085527 | * 7/2010 | ............... C07K 7/08 |
| KR | 20100085527 A | 7/2010 | |
| KR | 20110057049 A | 5/2011 | |
| KR | 20110060940 A | 6/2011 | |
| KR | 20110062943 A | 6/2011 | |
| KR | 20110130943 A | 12/2011 | |
| KR | 20120018188 A | 2/2012 | |
| KR | 20120026408 A | 3/2012 | |
| KR | 20120026408 A | 3/2012 | |
| KR | 20120035150 A | 4/2012 | |
| KR | 20120087885 A | 8/2012 | |
| KR | 20120121196 A | 11/2012 | |
| KR | 20120130996 A | 12/2012 | |
| KR | 20120133661 A | 12/2012 | |
| KR | 20130004949 A | 1/2013 | |
| KR | 20130041896 A | 4/2013 | |
| KR | 20140037698 A | 3/2014 | |
| KR | 20140104288 A | 8/2014 | |
| WO | WO-0002581 A1 | 1/2000 | |
| WO | WO-0007565 A2 | 2/2000 | |
| WO | WO 2009/025871 | 2/2009 | |
| WO | WO-2009120914 A1 | 10/2009 | |
| WO | WO-2010003520 A2 | 1/2010 | |
| WO | WO 2010/012850 A1 | 2/2010 | |
| WO | WO-2010022125 A1 | 2/2010 | |
| WO | WO-2010128807 A2 | 11/2010 | |
| WO | WO 2011/101173 A1 | 8/2011 | |
| WO | WO 2011/150494 A1 | 12/2011 | |
| WO | WO-2013100500 A1 | 7/2013 | |
| WO | WO-2013118899 A1 | 8/2013 | |
| WO | WO-2013135266 A1 | 9/2013 | |
| WO | WO-2013167298 A1 | 11/2013 | |
| WO | WO-2013167574 A1 | 11/2013 | |
| WO | WO-2013169060 A1 | 11/2013 | |
| WO | WO-2013169067 A1 | 11/2013 | |
| WO | WO-2013169077 A1 | 11/2013 | |
| WO | WO-2014012683 A1 | 1/2014 | |
| WO | WO-2014046478 A1 | 3/2014 | |
| WO | WO-2014046481 A1 | 3/2014 | |
| WO | WO-2014046490 A1 | 3/2014 | |
| WO | WO-2014130909 A1 | 8/2014 | |
| WO | WO-2014171792 A1 | 10/2014 | |
| WO | WO-2014196841 A1 | 12/2014 | |
| WO | WO-2014204281 A1 | 12/2014 | |
| WO | WO-2015060673 A1 | 4/2015 | |
| WO | WO-2015076621 A1 | 5/2015 | |
| WO | WO-2015093854 A1 | 6/2015 | |
| WO | WO-2015156649 A1 | 10/2015 | |
| WO | WO-2015167067 A1 | 11/2015 | |
| WO | WO-2016105086 A1 | 6/2016 | |
| WO | WO-2016137162 A1 | 9/2016 | |
| WO | WO-2017078440 A1 | 5/2017 | |

OTHER PUBLICATIONS

Ngo et al., Chapter 14 in The Protein Folding Problem and Tertiary Structure Prediction, Merz and LeGrand, Eds. 1994, 4 pages provided.*

Machine translation of JP 2010-252810, published Nov. 11, 2010, inventors Guadernack et al.*

Shay and Keith, British Journal of Cancer (2008) 98, 677-683.*

Abstract of Angelis, provided as PDF, 2006 (Year: 2006).*

Lee et al., Biomaterials 34 (2013) 7495-7505 (Year: 2013).*

Milletti, Drug Discovery Today, vol. 17, Nos. 15/16, Aug. 2012 (Year: 2012).*

Bridger et al, Bioconjugate Chem. 1996, 7, 255-264 (Year: 1996).*

Meyer-Losic, Clin Cancer Res 2145 2008;14(7) Apr. 1, 2008, 2145-2153 (Year: 2008).*

Deres et al., Nature vol. 342, pp. 561-564, 1989 (Year: 1989).*

Google meaning of 'conjugate' downloaded Nov. 10, 2020 from the internet, site: https://www.google.com/search?ei=7ByrX__FPNLH5gL354NA&q=conjugation+meaning+&oq=conjugation+meaning+(full result shortened) (Year: 2020).*

Co-pending Application, U.S. Appl. No. 15/479,746, inventors Kim, S.J., et al., filed Apr. 5, 2017 (Not Published).

ClinicalTrials.gov, "Gemcitabine, Capecitabine, and Telomerase Peptide Vaccine GV1001 in Treating Patients With Locally Advanced and Metastatic Pancreatic Cancer," Identifier NCT00425360, accessed at https://clinicaltrials.gov/archive/NCT00425360/2007_01_22, last accessed on Apr. 7, 2017, 4 pages.

ClinicalTrials.gov, "Adjuvant Leuprolide with or without Docetaxel in High Risk Prostate Cancer After Radial Prostatectomy," Identifier NCT00283062, first received on Jan. 26, 2006, accessed at https://clinicaltrials.gov./ct2/show/study/NCT00283062, last accessed on May 12, 2017, 7 pages.

Eisenegger, C., et al., "The Role of Testosterone in Social Interaction," Trends in Cognitive Sciences 15(6):263-271, Elsevier Science, England (2011).

Gong, W., et al., "Invasion Potential of H22 Hepatocarcinoma Cells is Increased by HMGB1-induced Tumor NF-κB Signaling via Initiation of HSP70," Oncology Reports 30(3):1249-1256, D.A. Spandidos, Greece (Jul. 2013).

Guo, R.F., et al., "Regulatory Effects of Eotaxin on Acute Lung Inflammatory Injury," Journal of Immunology 166(8):5208-5218, American Association of Immunologists, United States (2001).

Heldin, C.H., et al., "TGF-Beta Signalling from Cell Membrane to Nucleus through SMAD Proteins," Nature 390(6659):465-471, Nature Publishing Group, England (1997).

(56) References Cited

OTHER PUBLICATIONS

International Preliminary Report on Patentability for Application No. PCT/KR2014/004752, The International Bureau of WIPO, Switzerland, dated Nov. 1, 2016, 23 pages.
International Preliminary Report on Patentability for Application No. PCT/KR2015/0036642, The International Bureau of WIPO, Switzerland, dated Oct. 12, 2016, 18 pages.
International Preliminary Report on Patentability for International Application No. PCT/KR2014/010035, Korean Intellectual Property Office, Republic of Korea, dated Apr. 26, 2016, 13 pages.
International Search Report for International Application No. PCT/KR2014/004752, Korean Intellectual Property Office, Republic of Korea, dated Jan. 16, 2015, 10 pages.
International Search Report for International Application No. PCT/KR2015/003642, Korean Intellectual Property Office, Republic of Korea, dated Jul. 3, 2015, 8 pages.
Kawasaki, H., et al., "Detection and Evaluation of Activation of Various Cancer Antigenic Peptide-specific CTLs in Mature Dendritic Cells Used for Dendritic Cell Therapy," The 21st International Congress of Personalized Medicine, Conference Program and Abstracts, Personalized Medicine Universe (Japanese edition) 4(Supplement 2): 2 pages, Oct. 17, 2015.
Kyte, J.A. et al., "Telomerase Peptide Vaccination Combined with Temozolomide: A Clinical Trial in Stage IV Melanoma Patients," Clinical Cancer Research 17(13):4568-4580, The American Association of Cancer Research, United States (2011).
Mandal, A., "Types of Fibrosis," news-medical.net, accessed at http://www.news-medical.net/health/Types-of-Fibrosis.aspx, last accessed on Jul. 3, 2014, 3 pages.
Massague, J., "Tgf-Beta Signal Transduction," Annual Reviews of Biochemistry 67:753-791, Annual Reviews, United States (1998).
Middleton, G., et al., "Gemcitabine and Capecitabine With or Without Telomerase Peptide Vaccine GV1001 in Patients With Locally Advanced or Metastatic Pancreatic Cancer (TeloVec): an Open-Label, Randomised, Phase 3 Trial," The Lancet. Oncology 15(8):829-840, Lancet Pub. Group, England (Jul. 2014).
Morishita, M., and Peppas, N.A., "Is the Oral Route Possible for Peptide and Protein Drug Delivery?," Drug Discovery Today 11(19-20):905-910, Elsevier Science Ltd., England (2006).
National Center for Biotechnology Information, "Hormones," MeSH Database, Bethesda, accessed at http://www.ncbi.nlm.nih.gov/mesh.68006728, accessed on May 8, 2017, 3 pages.
National Institute of Diabetes and Digestive and Kidney Diseases, "Porstate Enlargement; Benign Prostatic Hyperplasia," accessed at https://www.niddk.nih.gov/health-information/urologic-diseases/prostate-problems/prostate-enlargement-benign-prostatic-hyperplasia, accessed Sep. 2014, 14 pages.
Nawroth, I., et al., "Intraperitoneal Administration of Chitosen/DsiRNA Nanoparticles Targeting TNFα Prevents Radiation-induced Fibrosis," Radiotherapy and Oncology 97(1):143-148, Elsevier Ireland Ltd., Ireland (2010).
Rosenbloom, J., et al., "Strategies for Anti-fibrotic Therapies," Biochimica et Biophysica Acta 1832(7):1088-1103, Elsevier B.V., Netherlands (Jul. 2013).
Sasada, A., et al., "A Case of Elderly Patient With Lung Cancer Efficiently Treated With Dendritic Cell Immunotherapy" The 20th International Congress of Personalized Medicine, Conference Program and Abstracts, Personalized Medicine Universe (Japanese edition) 4(Supplement 1): 2 pages, May 24, 2015.
"Seoul National University Bundang Hospital excited because of '000'," Clinical trials of Dream Anticancer Drug without side effects with Kael & GemVax, 4 pages, Apr. 22, 2013.
Shaw, V.E., et al., "Current Status of GV1001 and Other Telomerase Vaccination Strategies in the Treatment of Cancer," Expert Review of Vaccines 9(9):1007-1016, Taylor & Francis, England (2010).
Song, J., et al., "Characterization and Fate of Telomerase-Expressing Eptihelia during Kidney Repair," Journal of the American Society of Nephrology 22(12):2256-2265, American Society of Nephrology, United States (2011).

Tisdale, M.J., "Catabolic Mediators of Cancer Cachexia," Current Opinion in Supportive and Palliative Care, 2(4):256-261, Lippincott Williams & Wilkins, United States (2008).
Wang, W., et al., "Alleviating the Ischemia-Reperfusion Injury of Donor Liver by Transfection of Exogenous hTERT Genes," Transplantation Proceedings 41(5):1499-1503, Elsevier Science, United States (2009).
Written Opinion for International Application No. PCT/KR2014/004752, Korean Intellectual Property Office, Republic of Korea, dated Jan. 16, 2015, 21 pages.
Written Opinion for International Application No. PCT/KR2014/010035, Korean Intellectual Property Office, Republic of Korea, dated Feb. 2, 2015, 11 pages.
Written Opinion for International Application No. PCT/KR2015/003642, Korean Intellectual Property Office, Republic of Korea, dated Jul. 3, 2015, 16 pages.
Wynn, T.A. and Ramalingam, T.R., "Mechanisms of Fibrosis: Therapeutic Translation for Fibrotic Disease," Nature Medicine 18(7):1028-1040, Nature Publishing Company, United States (2012).
Yi, A., et al., "Radiation-Induced Complications after Breast Cancer Radiation Therapy: a Pictorial Review of Multimodality Imaging Findings," Korean Journal of Radiology 10(5):496-507, Korean Society of Radiology, Korea (2009).
Zhang, H., et al., "Inhibiting TGFβ1 has a Protective Effect on Mouse Bone Marrow Suppression Following Ionizing Radiation Exposure in Vitro," Journal of Radiation Research 54:(4):630-636, Oxford University Press, England (Jan. 2013).
International Preliminary Report on Patentability and Written Opinion for International Application No. PCT/KR2015/014099, The International Bureau of WIPO, dated Jun. 27, 2017, 16 pages.
International Search Report for International Application No. PCT/KR2015/014099, Korean Intellectual Property Office, Republic of Korea, dated May 4, 2016, 8 pages.
International Search Report for International Application No. PCT/KR2016/001646, Korean Intellectual Property Office, Republic of Korea, dated May 4, 2016, 8 pages.
De Araujo, J.G., et al., "The Potential Use of Melatonin for Preventing Cisplatin Ototoxicity: An Insight for a Clinical Approach," Advances in Otolaryngology vol. 2014, Article ID 185617, Hindawi Publishing Corporation, 8 pages (2014).
Kim, B-H., "Presbycusis: Review for its Enviromental Risk Factors," Korean J Otorhinolaryngol—Head Neck Surgery 49(10):962-967, Korean Society of Otolaryngology—Head and Neck Surgery, Korea (2006).
Lee, E.K., et al., "Inhibition of Experimental Choroidal Neovascularization by Telomerase-derived Peptide GV1001," Investigative Ophthalmology & Visual Science 56(7):Abstract 2291, ARVO Annual Meeting Abstract (2015).
Rowe-Redleman, C. and Glickman, R.D., "Possible therapy for age-related macular degeneration using human telomerase," Brain Research Bulletin 62(6):549-553, Elsevier Science Inc., United States (2004).
Co-pending Application, U.S. Appl. No. 15/539,396, inventor Kim, S.J., et al., I.A. filed Dec. 22, 2015 (Not Published).
Dementia from Merck Manual, accessed on Jul. 29, 2009, pp. 1-17.
Mattson, M.P., "Pathways Towards and Away From Alzheimer's Disease," Nature 430(7000):631-639, Nature Publishing Group, England (2004).
McConnell, J.D., et al., "The Effect of Finasteride on the Risk of Acute Urinary Retention and the Need for Surgical Treatment Among Men with Benign Prostatic Hyperplasia. Finasteride Long-term Efficacy and Safety Study Group," The New England Journal of Medicine 338(9):557-563, Massachusetts Medical Society, United States (1998).
Perez, R.G., et al., "The Beta-amyloid Precursor Protein of Alzheimer's Disease Enhances Neuron Viability and Modulates Neuronal Polarity," The Journal of Neuroscience 17(24):9407-9414, Society for Neuroscience, United States (1997).
Rheumatoid Arthritis from Merck Manual, accessed on Apr. 21, 2016, pp. 1-18.
Schenk, D., et al., "Immunization with Amyloid-beta Attenuates Alzheimer-disease-like Pathology in the PDAPP Mouse," Nature 400(6740):173-177, Nature Publishing Group, England (1999).

(56) References Cited

OTHER PUBLICATIONS

Van Coppenolle, F., et al., "Effects of Hyperprolactinemia on Rat Prostate Growth: Evidence of Androgeno-dependence," American Journal of Physiology. Endocrinology and Metabolism 280(1):E120-E129, American Physiological Society, United States (2001).
Altschul, S.F., et al., "Basic Local Alignment Search Tool," Journal of Molecular Biology 215(3):403-410, Elsevier, England (1990).
Bernhardt, S.L., et al., "Telomerase Peptide Vaccination of Patients with Non-Resectable Pancreatic Cancer: A Dose Escalating Phase I/II Study," British Journal of Cancer 95(11):1474-1482, Nature Publishing Group on behalf of Cancer Research, England (2006).
Bonaldi, T., et al., "Monocytic Cells Hyperacetylate Chromatin Protein HMGB1 to Redirect it Towards Secretion," The EMBO Journal 22(20):5551-5560, Wiley Blackwell, England (2003).
Brandenburg, K., et al., "Peptide-based Treatment of Sepsis," Applied Microbiology and Biotechnology 90(3):799-808, Springer International, Germany (2011).
Brunsvig, P.F., et al., "Telomerase Peptide Vaccination in NSCLC: A Phase II Trial in Stage III Patients Vaccinated after Chemoradiotherapy and an 8-year Update on a Phase I/II Trial," Clinical Cancer Research 17(21):6847-6857, The Association, United States (2011).
Choi, S.G., "Recent Advances in Cancer Cachexia," Journal of Korean Oncology Nursing 11(1):20-25 (2011).
Co-pending U.S. Appl. No. 14/413,732, inventor Sang Jae Kim, filed Jul. 11, 2013 (Not Published).
Co-pending U.S. Appl. No. 14/896,358, inventor Sang Jae Kim, filed Dec. 4, 2015 (Not Published).
Co-pending U.S. Appl. No. 14/899,746, inventor Sang Jae Kim, filed Apr. 12, 2015 (Not Published).
Dahlgren, K.N., et al., "Oligomeric and Fibrillar Species of Amyloid-beta Peptides Differentially Affect Neuronal Viability," Journal of Biological Chemistry 277(35):32046-32053, American Society for Biochemistry and Molecular Biology, United States (2002).
Dinarello, C.A., "Interleukin-1 in the Pathogenesis and Treatment of Inflammatory Diseases," Blood 117(14):3720-3732, American Society of Hematology, United States (2011).
Engineer, D.R. and Garcia, J.M., "Leptin in Anorexia and Cachexia Syndrome," International Journal of Peptides 2012:Article ID 287457, Hindawi Publishing Corporation, United States (2012).
Fujii, H., et al., "Telomerase Insufficiency in Rheumatoid Arthritis," Proceedings of the National Academy of Sciences USA 106(11):4360-4365, National Academy of Sciences, United States (2009).
GemVax Receives Report on Anti-Inflammatory Mechanism, The Asia Economy Daily, Article written on May 7, 2013.
Ghaneh, P., et al., "Biology and Management of Pancreatic Cancer," Gut 56(8):1134-1152, British Medical Association, England (2007).
Granger, D.N. and Korthuis, R.J., "Physiologic Mechanisms of Postischemic Tissue Injury," Annual Review of Physiology 57:311-332, Annual Reviews, United States (1995).
Gunturu, K.S., et al., "Immunotherapy Updates in Pancreatic Cancer: Are we there yet?," Therapeutic Advances in Medical Oncology 5(1):81-89, Sage, England (2013).
HSE, "Rheumatoid arthritis," http://www.hse.ie/portal/eng, accessed at http://www.hse.ie/portal/eng/health/az/R/Rheumatoid-arthritis/, 14 pages (2013).
Inderberg-Suso, E.M., et al., "Widespread CD4+ T-cell Reactivity to Novel hTERT Epitopes following Vaccination of Cancer Patients with a Single hTERT Peptide GV1001," Oncoimmunology 1(5):670-686, Taylor & Francis, United States (2012).
International Preliminary Report on Patentability for International Application No. PCT/EP2013/059460, International Bureau of WIPO, Switzerland, dated Nov. 11, 2014, 5 pages.
International Preliminary Report on Patentability for International Application No. PCT/KR2013/004145, The International Bureau of WIPO, Switzerland, dated Nov. 11, 2014, 14 pages.
International Preliminary Report on Patentability for International Application No. PCT/KR2013/004176, The International Bureau of WIPO, Switzerland, dated Nov. 11, 2014, 14 pages.

International Preliminary Report on Patentability for International Application No. PCT/KR2013/006218, The International Bureau of WIPO, Switzerland, dated Jan. 13, 2015,27 pages.
International Preliminary Report on Patentability for International Application No. PCT/KR2014/003425, The International Bureau of WIPO, Switzerland, dated Oct. 20, 2015, 14 pages.
International Preliminary Report on Patentability for International Application No. PCT/KR2014/005031, The International Bureau of WIPO, Switzerland, dated Dec. 8, 2015, 8 pages.
International Preliminary Report on Patentability for International Application No. PCT/KR2014/005508, The International Bureau of WIPO, Switzerland, dated Jan. 5, 2016, 14 pages.
International Preliminary Report on Patentability for International Patent Application No. PCT/KR2013/004156, The International Bureau of WIPO, Geneva, Switzerland, dated Nov. 11, 2014, 15 pages.
International Search Report for International Application No. PCT/KR2014/003425, Korean Intellectual Property Office, Republic of Korea, dated Jul. 21, 2014, 8 pages.
International Search Report for International Application No. PCT/EP2013/059460, European Patent Office, Netherlands, dated Jul. 3, 2013, 5 pages.
International Search Report for International Application No. PCT/KR2013/004145, Korean Intellectual Property Office, Republic of Korea, dated Aug. 14, 2013, 10 pages.
International Search Report for International Application No. PCT/KR2013/004176, Korean Intellectual Property Office, Republic of Korea, dated Aug. 6, 2013, 10 pages.
International Search Report for International Application No. PCT/KR2014/005031, Korean Intellectual Property Office, Republic of Korea, dated Sep. 22, 2014, 6 pages.
International Search Report for International Application No. PCT/KR2014/005508, Korean Intellectual Property Office, Republic of Korea, dated Oct. 14, 2014, 8 pages.
International Search Report for International Patent Application No. PCT/KR2013/004156, Korean Intellectual Property Office, Republic of Korea, dated Aug. 14, 2013, 10 pages.
Kern, K.A. and Norton, J.A., "Cancer Cachexia," Journal of Parenteral and Enteral Nutrition 12(3):286-298, Sage Publications, United States (1988).
Kim, H.O. and Lee, S.I., "Experimental Animal Models for Rheumatoid Arthritis: Methods and Applications," Journal of Rheumatic Diseases 19(4):189-195, The Korean College of Rheumatology, Republic of Korea(2012).
Kokhaei, P., et al., "Telomerase (hTERT 611-626) Serves as a Tumor Antigen in B-cell Chronic Lymphocytic Leukemia and Generates Spontaneously Antileukemic, Cytotoxic T Cells," Experimental Hematology 35(2):297-304, Elsevier Science Inc., Netherlands (2007).
Kyte, J.A., "Cancer Vaccination with Telomerase Peptide GV1001," Expert Opinion on Investigational Drugs 18(5):687-694, Taylor & Francis, England (2009).
Lahdevirta, J., et al., "Elevated Levels of Circulating Cachectin/tumor Necrosis Factor in Patients with Acquired Immunodeficiency Syndrome," American Journal of Medicine 85(3):289-291, Excerpta Medica, United States (1988).
Laviano, A., et al., "Therapy Insight: Cancer Anorexia-cachexia Syndrome—When All You Can Eat is Yourself," Nature Clinical Practice. Oncology 2(3):158-165, Nature Publishing Group, England (2005).
Martinez, P. and Blasco, M.A., "Telomeric and Extra-telomeric Roles for Telomerase and the Telomere-binding Proteins," Nature Reviews Cancer 11(3):161-176, Nature Publishing Group, England (2011).
Myers, L.K., et al., "Collagen-Induced Arthritis, an Animal Model of Autoimmunity," Life Sciences 61(19):1861-1878, Elsevier, Netherlands (1997).
National Horizon Scanning Centre News on Emerging Technologies in Healthcare, GV1001 for Advanced and/or Metastatic Pancreatic Cancer, Published Apr. 2008.
NCBI, Reference Sequence: XP_003776612.1 (Jul. 17, 2012).
Oh, H., et al., "Telomerase Reverse Transcriptase Promotes Cardiac Muscle Cell Proliferation, Hypertrophy, and Survival," Proceedings

(56) References Cited

OTHER PUBLICATIONS of the National Academy of Sciences 98(18): 10308-10313, National Academy of Sciences, United States (2001).
Pearson, W.R. and Lipman, D.J., "Improved Tools for Biological Sequence Comparison," Proceedings of the National Academy of Sciences USA 85(8):2444-2448, National Academy of Sciences, United States (1988).
Roubenoff, R., et al., "Adjuvant Arthritis as a Model of Inflammatory Cachexia," Arthritis and Rheumatism 40(3):534-539, Wiley-Blackwell, United States (1997).
Schlapbach, C., et al., "Telomerase-specific GV1001 Peptide Vaccination Fails to Induce Objective Tumor Response in Patients with Cutaneous T Cell Lymphoma," Journal of Dermatological Science 62(2):75-83, Elsevier, Netherlands (2011).
Smith, T.F. and Waterman, M.S., "Comparison of Biosequences," Advances in Applied Mathematics 2(4):482-489, Academic Press, Inc., United States (1981).
Southern Cross, "Rheumatoid arthritis—causes, symptoms, and treatment," https://www.southerncross.co.nz/, accessed at https://www.southerncross.co.nz/AboutTheGroup/HealthResources/MedicalLibrary/tabid/178/vw/1/itemID/124/Rheumatoid-arthritis-causes-symptoms-treatment.aspx, last reviewed on May 31, 2013, 5 pages.
Stevenson, C.L., "Advances in Peptide Pharmaceuticals," Current Pharmaceutical Biotechnology 10(1):122-137, Bentham Science Publishers, United Arab Emirates (2009).
Taylor, P.C. and Feldmann, M., "Anti-TNF Biologic Agents: Still the Therapy of Choice for Rheumatoid Arthritis," Nature Reviews. Rheumatology 5(10):578-582, Macmillan Publishers Limited, England (2009).
Thompson, J.D., et al., "Clustal W: Improving the Sensitivity of Progressive Multiple Sequence Alignment Through Sequence Weighting, Position-specific Gap Penalties and Weight Matrix Choice," Nucleic Acids Research 22(22):4673-4680, Oxford University Press, England (1994).
Tisdale, M.J., "Mechanisms of Cancer Cachexia," Physiological Reviews 89(2):381-410, American Physiological Society, United States (2009).
Vennela, B., et al., "Current and Future Strategies for Therapy of Pancreatic Cancer," International Journal of Research in Pharmacy and Medicine 2(3):728-740 (2012).
Walsmith, J. and Roubenoff, R., "Cachexia in Rheumatoid Arthritis," International Journal of Cardiology 85(1):89-99, Elsevier, Netherlands (2002).
Written Opinion for International Application No. PCT/EP2013/059460, European Patent Office, Germany, dated Jul. 3, 2013, 4 pages.
Written Opinion for International Application No. PCT/KR2013/004145, Korean Intellectual Property Office, Republic of Korea, dated Aug. 14, 2013, 13 pages.
Written Opinion for International Application No. PCT/KR2013/004176, Korean Intellectual Property Office, Republic of Korea, dated Aug. 6, 2013, 13 pages.
Written Opinion for International Application No. PCT/KR2014/005031, Korean Intellectual Property Office, Republic of Korea, dated Sep. 22, 2014, 7 pages.
Written Opinion for International Application No. PCT/KR2014/005508, Korean Intellectual Property Office, Republic of Korea, dated Oct. 14, 2014, 13 pages.
Written Opinion for International Patent Application No. PCT/KR2013/004156, Korean Intellectual Property Office, Republic of Korea, dated Aug. 14, 2013, 13 pages.
Written Opinion for International Application No. PCT/KR2014/003425, Korean Intellectual Property Office, Republic of Korea, dated Jul. 21, 2014, 13 pages.
Yankner, B.A., et al., "Neurotrophic and Neurotoxic Effects of Amyloid Beta Protein: Reversal by Tachykinin Neuropeptides," Science 250(4978):279-282, American Association for the Advancement of Science, United States (1990).

International Search Report for International Application No. PCT/KR2014/010035, Korean Intellectual Property Office, Republic of Korea, dated Feb. 2, 2015, 8 pages.
Shay, J.W., et al., "Telomerase therapeutics for cancer: challenges and new directions," Nature Reviews Drug Discovery 5(7): 577-584, Nature Publishing Group, England (2006).
Fire, A., et al., "Potent and Specific Genetic Interference by Double-stranded RNA in Caenorhabditis Elegans," Nature 391(6669):806-811, Nature Publishing Group, England (1998).
Fittipaldi, A., et al., "Cell Membrane Lipid Rafts Mediate Caveolar Endocytosis of HIV-1 Tat Fusion Proteins," Journal of Biological Chemistry 278(36): 34141-34149, American Society for Biochemistry and Molecular Biology, United States(2003).
International Searching Authority, International Search Report for International Application No. PCT/KR2013/006218, Korean Intellectual Property Office, Republic of Korea, dated Sep. 26, 2013, 8 pages.
Luft, R., et al., "A Case of Severe Hypermetabolism of Nonthyroid Origin with a Defect in the Maintenance of Mitochondrial Respiratory Control: A Correlated Clinical, Biochemical, and Morphological Study," Journal of Clinical Investigation 41:1776-1804, American Society for Clinical Investigation, United States (1962).
Modica-Napolitano, J.S. and Singh, K.K., "Mitochondria as Targets for Detection and Treatment of Cancer," Expert Reviews in Molecular Medicine 4(9):1-19, Cambridge University Press, England (2002).
Novina, C.D. and Sharp, P.A., "The RNAi Revolution," Nature 430(6996):161-164, Nature Publishing Group, England (2004).
Rana, T.M., "Illuminating the Silence: Understanding the Structure and Function of Small RNAs," Nature Reviews. Molecular Cell Biology 8(1):23-36, Nature Publishing Group, England (2007).
Smith, D.B. and Johnson, K.S., "Single-step Purification of Polypeptides Expressed in *Escherichia coli* as Fusions with Glutathione S-transferase," Gene 67(1):31-40, Elsevier, Netherlands (1988).
Tomari Y. and Zamore, P.D., "Perspective: Machines for RNAi," Genes and Development 19(5):517-529, Cold Spring Harbor Laboratory Press, United States (2005).
International Searching Authority, Written Opinion for International Application No. PCT/KR2013/006218, Korean Intellectual Property Office, Republic of Korea, dated Sep. 26, 2013, 26 pages.
Cho, Y.J., "GemVax & Keel (082270), A Godsend About to Arrive," Hana Daetoo Securities, Company Report, Sep. 10, 2012, 8 pages.
Fonseca, S.B., et al., "Recent advances in the use of cell-penetrating peptides for medical and biological applications," Adv. Drug Deliv. Rev. 61(11):953-964, Elsevier Science Publishers, Netherlands (2009).
Heitz, F., et al., "Twenty years of cell-penetrating peptides: from molecular mechanisms to therapeutics," Br. J. Pharmacol. 157(2):195-206, Wiley, England (2009).
International Searching Authority, International Search Report for International Application No. PCT/KR2013/008459, Korean Intellectual Property Office, Republic of Korea, dated Dec. 23, 2013, 8 pages.
Lee, S.A., et al., "Heat shock protein-mediated cell penetration and cytosolic delivery of macromolecules by a telomerase-derived peptide vaccine," Biomaterials 34(30):7495-7505, Elsevier Science, Netherlands (2013).
International Searching Authority, Written Opinion for International Application No. PCT/KR2013/008459, Korean Intellectual Property Office, Republic of Korea, dated Dec. 23, 2013, 9 pages.
International Searching Authority, International Search Report for International Patent Application No. PCT/KR2013/008438, Korean Intellectual Property Office, Republic of Korea, dated Dec. 23, 2013, 3 pages.
International Bureau of WIPO, International Preliminary Report on Patentability for International Patent Application No. PCT/KR2013/008438, The International Bureau of WIPO, Switzerland, dated Mar. 24, 2015, 6 pages.
International Searching Authority, Written Opinion for International Patent Application No. PCT/KR2013/008438, Korean Intellectual Property Office, Republic of Korea, dated Dec. 23, 2013, 5 pages.
International Searching Authority, International Search Report for International Patent Application No. PCT/KR2013/008445, Korean Intellectual Property Office, Republic of Korea, dated Dec. 23, 2013, 4 pages.

(56) References Cited

OTHER PUBLICATIONS

International Bureau of WIPO, International Preliminary Report on Patentability for International Patent Application No. PCT/KR2013/008445, The International Bureau of WIPO, Switzerland, dated Mar. 24, 2015, 7 pages.
International Searching Authority, Written Opinion of the International Searching Authority for International Patent Application No. PCT/KR2013/08445, Korean Intellectual Property Office, Republic of Korea, dated Dec. 23, 2013, 6 pages.
Co-pending U.S. Appl. No. 14/429,637; inventor Sang Jae Kim; filed Sep. 17, 2013 (Not Published).
Co-pending U.S. Appl. No. 14/429,641; inventor Sang Jae Kim; filed Sep. 17, 2013 (Not Published).
Co-pending U.S. Appl. No. 14/429,644; inventor Sang Jae Kim; filed Sep. 17, 2013 (Not Published).
Beer, T.M., et al., "Phase II Study of Weekly Docetaxel in Symptomatic Androgen-independent Prostate Cancer," Annals of Oncology 12(9):1273-1279, Oxford University Press, England (2001).
Bohonowych, J.E., et al., "Comparative Analysis of Novel and Conventional HSP90 Inhibitors on HIF Activity and Angiogenic Potential in Clear Cell Renal Cell Carcinoma: Implications for Clinical Evaluation," BMC Cancer 11:520, BioMed Central, England (2011).
Bruns, A.F., et al., "A Heat-shock Protein Axis Regulates VEGFR2 Proteolysis, Blood Vessel Development and Repair," PloS One 7(11):e48539, Public Library of Science, United States (2012).
Calderwood, S.K., et al., "Heat Shock Proteins in Cancer: Chaperones of Tumorigenesis," Trends in Biochemical Sciences 31(3):164-172, Elsevier Trends Journals, England (2006).
Dempsey, N.C., et al., "Differential Heat Shock Protein Localization in Chronic Lymphocytic Leukemia," Journal of Leukocyte Biology 87(3):467-476, Society for Leukocyte Biology, United States (2010).
Du, R., et al., "HIF1 alpha Induces the Recruitment of Bone Marrow-derived Vascular Modulatory Cells to Regulate Tumor Angiogenesis and Invasion," Cancer Cell 13(3):206-220, Cell Press, United States (2008).
Eustace, B.K. and Jay, D.G., "Extracellular Roles for the Molecular Chaperone, Hsp90," Cell Cycle 3(9):1098-1100, Taylor & Francis, United States (2004).
Eustace, B.K. and Jay, D.G., "Functional Proteomic Screens Reveal an Essential Extracellular Role for Hsp90 Alpha in Cancer Cell Invasiveness," Nature Cell Biology 6(6):507-514, Macmillan Magazines Ltd., England (2004).
Evans, C.G., et al., "Heat Shock Protein 70 (Hsp70) as an Emerging Drug Target," Journal of Medicinal Chemistry 53(12):4585-4602, American Chemical Society, United States (2010).
Ferrarini, M., et al., "Unusual Expression and Localization of Heat-shock Proteins in Human Tumor Cells," International Journal of Cancer 51(4):613-619, Wiley-Liss, United States (1992).
Garcia-Carbonero, R., et al., "Inhibition of HSP90 Molecular Chaperones: Moving Into the Clinic," The Lancet Oncology 14(9):e358-e369, Lancet Publishing Group, England (2013).
Henry, J.Y., et al., "Lenalidomide Enhances the Anti-prostate Cancer Activity of Docetaxel in vitro and in vivo," The Prostate 72(8):856-867, Wiley-Liss, United States (2012).
International Preliminary Report on Patentability for International Application No. PCT/KR2014/011280, The International Bureau of WIPO, Geneva, Switzerland, dated May 24, 2016, 15 pages.
International Search Report for International Application No. PCT/KR2014/011280, Korean Intellectual Property Office, Republic of Korea, dated Feb. 11, 2015, 12 pages.
International Search Report for International Application No. PCT/KR2014/012502, Korean Intellectual Property Office, Republic of Korea, dated Mar. 11, 2015, 10 pages.
International Preliminary Report on Patentability for International Application No. PCT/KR2014/012502, The International Bureau of WIPO, Geneva, Switzerland, dated Jun. 21, 2016, 22 pages.
Jaattela, M., "Over-expression of Hsp70 Confers Tumorigenicity to Mouse Fibrosarcoma Cells," International Journal of Cancer 60(5):689-693, Wiley-Liss, United States (1995).
Jemal, A., et al., "Cancer Statistics, 2008," CA: A Cancer Journal for Clinicians 58(2):71-96, Wiley, United States (2008).
Kim, B.K., et al., "Tumor-suppressive Effect of a Telomerase-derived Peptide by Inhibiting Hypoxia-induced HIF-1α-VEGF Signaling Axis," Biomaterials 35(9):2924-2933, Elsevier Science, Netherlands (2014).
Kocsis, J., et al., "Serum Level of Soluble 70-kD Heat Shock Protein Is Associated With High Mortality in Patients With Colorectal Cancer Without Distant Metastasis," Cell Stress & Chaperones 15(2):143-151, Springer, Netherlands (2010).
Liu, Q.J., et al., "Rapamycin Enhances the Susceptibility of Both Androgen-dependent and -independent Prostate Carcinoma Cells to Docetaxel," Chinese Medical Journal 123(3):356-360, Chinese Medical Association, China (2010).
Morano, K.A., "New Tricks for an Old Dog: the Evolving World of Hsp70," Annals of the New York Academy of Sciences 1113:1-14, Blackwell, United States (2007).
Murphy, M.E., "The Hsp70 Family and Cancer," Carcinogenesis 34(6):1181-1188, Irl Press, England (2013).
Nagaraju, G.P., et al., "Antiangiogenic Effects of Ganetespib in Colorectal Cancer Mediated Through Inhibition of HIF-1α and STAT-3," Angiogenesis 16(4):903-917, Springer, Germany (2013).
Pfosser, A., et al., "Liposomal HSP90 Cdna Induces Neovascularization via Nitric Oxide in Chronic Ischemia," Cardiovascular Research 65(3):728-736, Oxford Journals, England (2005).
Powers, M.V., et al., "Targeting HSP70: the Second Potentially Druggable Heat Shock Protein and Molecular Chaperone?," Cell Cycle 9(8):1542-1550, Taylor & Francis, United States (2010).
Sayers, S., et al., "Vaxjo: A Web-based Vaccine Adjuvant Database and its Application for Analysis of Vaccine Adjuvants and their Uses in Vaccine Development," Journal of Biomedicine and Biotechnology 2012:1-13, Article ID 831486, Hindawi Publishing Corporation, United States (2012).
Seo, J.S., et al., "T Cell Lymphoma in Transgenic Mice Expressing the Human Hsp70 Gene," Biochemical and Biophysical Research Communications 218(2):582-587, Elsevier, United States (1996).
Sun, J., et al., "Induction of Angiogenesis by Heat Shock Protein 90 Mediated by Protein Kinase Akt and Endothelial Nitric Oxide Synthase," Arteriosclerosis, Thrombosis, and Vascular biology 24(12):2238-2244, Lippincott Williams & Wilkins, United States (2004).
Uehara, Y., "Natural Product Origins of Hsp90 Inhibitors," Current Cancer Drug Targets 3(5):325-330, Bentham Science Publishers, Netherlands (2003).
Vanbuskirk, A., et al., "A Peptide Binding Protein Having a Role in Antigen Presentation Is a Member of the HSP70 Heat Shock Family," The Journal of Experimental Medicine 170(6):1799-1809, Rockefeller University Press, United States (1989).
Volloch, V.Z. and Sherman, M.Y., "Oncogenic Potential of Hsp72," Oncogene 18(24):3648-3651, Nature Publishing Group, England (1999).
Written Opinion for International Application No. PCT/KR2014/011280, Korean Intellectual Property Office, Republic of Korea, dated Feb. 11, 2015, 14 pages.
Written Opinion for International Application No. PCT/KR2014/012502, Korean Intellectual Property Office, Republic of Korea, dated Mar. 11, 2015, 20 pages.
Yeh, C.H., et al., "Clinical Correlation of Circulating Heat Shock Protein 70 in Acute Leukemia," Leukemia Research 34(5):605-609, Pergamon Press, England (2010).
Zhou, J., et al., "PI3K/Akt Is Required for Heat Shock Proteins to Protect Hypoxia-inducible Factor 1alpha From pVHL-independent Degradation," The Journal of Biological Chemistry 279(14):13596-13513, American Society for Biochemistry and Molecular Biology, United States (2004).
Auerbach, R., et al., "Angiogenesis Assays: Problems and Pitfalls," Cancer Metastasis Reviews 19(1-2):167-172, Kluwer Academic, Netherlands (2000).
Delves, P.J., "Allergic Rhinitis," Merck manual, accessed at http://www.merckmanuals.com/professional/immunology-allergic-disorders/allergic,-autoimmune,-and-other-hypersensitivity-disorders/allergic-rhinitis, accessed on Nov. 2, 2017, pp. 1-6.

(56) References Cited

OTHER PUBLICATIONS

Fauce, S.R., et al., "Telomerase-Based Pharmacologic Enhancement of Antiviral function of Human CD8+ T Lymphocytes," Immunology 181(10):7400-7406, American Association of Immunologists, United States (Nov. 2008).
Fontanes, V., et al., "A cell permeable peptide inhibits Hepatitis C Virus Replication by Sequestering IRES Transacting Factors," Virology 394(1):82-90, Academic Press, United States (Nov. 2009).
Fried, M.P., "Nonallergic Rhinitis," Merck manual, accessed at http://www.msdmanuals.com/professional/ear,-nose,-and-throat-disorders/nose-and-paranasal-sinus-disorders/nonallergic-rhinitis, accessed on Nov. 2, 2017, pp. 1-3.
International Search Report for Application No. PCT/KR2016/007192, dated Sep. 12, 2016, 12 pages.
Jain, R.K., "Barriers to Drug Delivery in Solid Tumors," Scientific American 271(1):58-65, Scientific American, Inc., United States (Jul. 1994).
Kim, H., et al., "Inhibition of HIV-1 Reactivation by a Telomerase-Derived Peptide in a HSP90-Dependent Manner," Scientific Reports 6: 28896, Nature Publishing Group, England (Jul. 2016).
Lee, S.A., et al., "A Telomerase-Derived Peptide Regulates Reactive Oxygen Species and Hepatitis C Virus RNA Replication in HCV-Infected Cells Via Heat Shock Protein 90, "Biochemical and Biophysical Research Communications 471(1):156-162, Elsevier, United States (Feb. 2016).
Leem G., et al., Immunotherapy in Pancreatic Cancer; the Road Less Traveled Immunol Disord Immunotherapy, Jun. 26, 2016 (Jun. 26, 2016), p. 1000106, XP055328627, Retrieved from the Internet: (URL:http://www.omicsgroup.orgjjournalsjimmunotherapy-in-pancreatic-cancer-the-road-less-traveled-IDIT-1000104.pdf).
Merck Manual: Respiratory Diseases, Medical Topics, accessed on Nov. 2, 2017, pp. 1-4.
Middleton, G.W., "A Phase III Randomized Trial of Chemoimmunotherapy Comprising Gemcitabine and Capecitabine with or Without Telomerase Vaccine GV1001 in Patients with Locally Advanced or Metastatic Pancreatic Cancer," Presented at conference ASCO, (Jun. 4, 2013), XP054977010. Retrieved from the Internet: (URL: http://meetinglibrary.asco.orgjcontent/82894?media=vm).
Middleton, G.W., et al., Phase III Randomized Trial of Chemoimmunotherapy Comprising Gemcitabine and Capecitabine with or without Telomerase Vaccine GV1001 in Patients with Locally Advanced or Metastatic Pancreatic Cancer, ASCO Annual Meeting, 31:1-3, (May 31, 2013)-(Jun. 4, 2013), XP055328310.
Middleton, G.W., et al., Poster: Predictive Cytokine Biomarkers for Survival in Patients with Advanced Pancreatic Cancer Randomized to Sequential Chemoimmunotherapy Comprising Gemcitabine and Capecitabine (GemCap) Followed by the Telomerase Vaccine GV1001 Compared to Concurrent Chemoimmunotherapy in the Telovac Phase III tr, ASCO 2014, May 30, 2014 (May 30, 2014)-Jun. 3, 2014 (Jun. 3, 2014), pp. 1-1. XP055328448. Retrieved from the Internet: (URL:http://media4.asco.org/144/8599/93976/93976_poster_pvhr.jpg).
Neoptolemos J.P., et al., "Predictive 1-20 Cytokine Biomarkers for Survival in Patients With Advanced Pancreatic Cancer Randomized to Sequential Chemoimmunotherapy Comprising Gemcitabine and Capecitabine (Gemcap) Followed by the Telomerase Vaccine GV1001 Compared to Concurrent Chemoimmunotherapy in the Telovac Phase III trial," 2014 ASCO Annual Meeting, May 30, 2014 (May 30, 2014)-Jun. 3, 2014 (Jun. 3, 2014), pp. 1-3.
Ortega, V.E., "Asthma," Merck manual, accessed at http://www.merckmanuals.com/professional/pulmonary-disorders/asthma-and-related-disorders/asthma, accessed on Nov. 2, 2017, pp. 1-19.
Albini, A., et al., "Cancer Prevention by Targeting Angiogenesis," Nature reviews Clinical oncology 9(9):498-509, Nature Pub Group (2012).
Extended European Search Report for Application No. EP14808179, dated May 24, 2017, 24 pages.
O'Beirne, J., et al., "Generation of Functional CD8+ T Cells by Human Dendritic Cells Expressing Glypican-3 Epitopes," in: Journal of Experimental and Clinical Cancer Research 29:48, BioMed Central, London (May 2010).
Priya, S.G., et al., "Skin Tissue Engineering for Tissue Repair and Regeneration," Tissue Engineering. Part B, Reviews 14(1):105-118, Mary Ann Liebert, Inc., United States (2008).
Supplemental European Search Report for Application No. EP14808179, dated Jan. 10, 2017, 13 pages.
Varma, N., et al., "Role of hTERT and WT1 Gene Expression in Disease Progression and Imatinib Responsiveness of Patients with BCR-ABL Positive Chronic Myeloid Leukemia," in: Leukemia and Lymphoma 52(4):687-693, Informa Healthcare, London (Apr. 2011).
Rosenstein, B.J., "Cystic Fibrosis," Merck manual, accessed at http://www.msdmanuals.com/professional/pediatrics/cystic-fibrosis-cf/cystic-fibrosis, accessed on Nov. 2, 2017, pp. 1-15.
International Preliminary Report on Patentability and Written Opinion for International Application No. PCT/KR2016/001646, Korean Intellectual Property Office, Republic of Korea, dated May 20, 2016, 13 pages.
Westin, E.R., et al., "The p53/p21(WAF/CIP) Pathway Mediates Oxidative Stress and Senescence in Dyskeratosis Congenita Cells With Telomerase Insufficiency," Antioxidants & Redox Signaling 14(6):985-997, Mary Ann Liebert, Inc., United States (2011).
Written opinion for Application No. PCT/KR2016/007192, dated Sep. 12, 2016, 16 pages.
Kirino, T, "Delayed Neuronal Death in the Gerbil Hippocampus Following Ischemia," Brain Research 239(1):57-69, Amsterdam Elsevier/North-Holland Biomedical Press, Netherlands (May 1982).
Olney, J.W., et al., "Pathological Changes Induced in Cerebrocortical Neurons by Phencyclidine and Related Drugs," Science 244(4910):1360-1362, American Association for the Advancement of Science, United States (Jun. 1989).
International Search Report and Written Opinion for Application No. PCT/KR2016/012613, dated May 11, 2017, 14 pages.
Co-pending Application, U.S. Appl. No. 15/772,928, inventors Kim, Sang Jae., et al., filed Nov. 3, 2016.
Godet, Y., et al. "Analysis of spontaneous tumor-specific CD4 T-cell immunity in lung cancer using promiscuous HLA-DR telomerase-derived epitopes: potential synergistic effect with chemotherapy response." Clinical Cancer Research 18(10): 2943-2953, American Association for Cancer Research (2012).

* cited by examiner a) no treat b) FITC c) TAT d) pep 1

Stem cells with pep1-Fe

Stem cells without pep1-Fe a) no treat b) GFP c) TAT d) pep1

| Peptides | Sequences |
|---|---|
| GGG-pK | NH$_2$-GGG-pK-COOH |
| TAT-pK | NH$_2$-YGRKKRRQRRR-GGG-pK-COOH |
| hTERT-pK | NH$_2$-EARPALLTSRLRFIPK-GGG-pK-COOH |

CELL-PENETRATING PEPTIDE, CONJUGATE COMPRISING SAME AND COMPOSITION COMPRISING SAME

REFERENCE TO SEQUENCE LISTING SUBMITTED ELECTRONICALLY

The content of the electronically submitted sequence listing (Name 24730800006 SequenceListing_ST25.txt; Size: 16,271 bytes; and Date of Creation: Oct. 30, 2015) filed with the application is incorporated herein by reference in its entirety.

FIELD OF THE INVENTION

The present invention relates to cell penetrating peptides derived from human telomerase reverse transcriptase (hTERT) enzyme, conjugates of the cell penetrating peptides, active ingredients, and compositions comprising the conjugate.

BACKGROUND

Although Low-molecular weight substances, nucleic acids, proteins, nano-particles, etc, have great potentials as therapeutic substances at a molecular level, their uses are limited due to the incompetence to penetrate into tissues and cell membrane. The development of a system to deliver such substances into the cell has been the active area of research over the last two decades. transport the substances inside the cell has been a conversation topic in a treatment of molecular method. Low-molecular weight substances, nucleic acids or nano-particles were transported inside the cell by several reagents, electroporation or heatshock. However, it was difficult to find an adequate method of delivery of proteins inside the cell without disrupting the activity and integrity of proteins. In 1980s, in the research conducted on studying the cell penetrating capacity of HIV, it was found that HIV-TAT protein consisting of specific 11 amino acids play an important role in a process of transportation inside the cell. Thus, in 1990s, studies on finding the right method of transporting proteins inside the cell has been the intense area of research.

Telomere is known as a repetitive sequence of genetic material found at the ends of chromosomes that prevent chromosomes from damage or merging onto other chromosomes. The length of the telomere is shortened at each cell division, and after a certain number of cell division, the telomere length is extremely shortened to the extent in which the cell stops dividing and dies. On the other hand, the elongation of telomeres is known to extend the life span of a cell. For an example, cancer cells excrete an enzyme called telomerase, which prevents shortening of telomeres, thus resulting in proliferation of cancer cells.

The objective of this invention is to provide a cell penetrating peptide.

Another objective of present invention is to provide a useful peptide as a carrier of the active ingredient in a cell.

Another objective of present invention is to provide a useful peptide as a carrier of the active ingredient in a cell, especially deliver to mitochondria locally.

Another objective of present invention is to provide a useful peptide for delivery of active ingredient to mitochondria for improvement, prophylaxis or treatment of mitochondria related disease or disorder.

Another objective of present invention is to provide a conjugate that an active ingredient and cell penetrating peptide are conjugated.

Another objective of present invention is to provide a composition comprising a conjugate of an active ingredient and cell penetrating peptide.

Another objective of present invention is to provide a pharmaceutical composition comprising a conjugate of an active ingredient and cell penetrating peptide.

Another objective of present invention is to provide a functional cosmetic composition comprising a conjugate of an active ingredient and cell penetrating peptide.

Another objective of present invention is to provide a health food composition comprising a conjugate of an active ingredient and cell penetrating peptide.

Another objective of present invention is to provide a contrast agent comprising a conjugate of an active ingredient and cell penetrating peptide.

SUMMARY OF THE INVENTION

The conjugate according to the one embodiment of the present invention may be a conjugate of cell penetrating carrier peptide and active ingredients, wherein the carrier peptide is the peptide comprising amino acid sequence of SEQ ID NO: 1, the peptide having above 80% homology of amino acid sequence with above-mentioned sequence, or the fragment of the above-mentioned peptides, and wherein the peptide having above 80% homology of amino acid sequence with above-mentioned sequence and the fragment of the same are the peptides that maintain cell penetrating ability of SEQ ID NO: 1.

According to another embodiment of the conjugate in the present invention, the fragment may be made of 3 or more amino acids.

According to another embodiment of the conjugate in the present invention, the carrier peptide may be made of 30 or less amino acids.

According to another embodiment of the conjugate in the present invention, the above-mentioned carrier peptide may be the peptide having amino acid sequence of SEQ ID NO: 1 or the peptide having above 80% homology of amino acid sequence with above-mentioned sequence.

The contrast agent according to the one embodiment of the present invention may comprise any one conjugate above-mentioned.

The contrast agent according to the one embodiment of the present invention may be for contrasting a cell.

According to another embodiment of the contrast agent in the present invention, the cell may be a stem cell.

The composition according to one embodiment of the present invention may comprise any one of conjugates above-mentioned.

According to another embodiment of the composition in the present invention, the active ingredient may be for treatment or prevention of disease, and the composition may be pharmaceutical composition.

According to another embodiment of the composition in the present invention, the active ingredient may be the active ingredient for functional cosmetics, and the composition may be cosmetic composition.

According to another embodiment of the composition in the present invention, the active ingredient may be the active ingredient for functional health food, and the composition may be health food composition.

The cytoplasm targeting delivery system of active ingredient according to the one embodiment of the present invention may comprise any one of conjugates mentioned above, wherein the carrier peptide moves into a cytoplasm locally and performs a role of local cytoplasm delivering the mentioned active ingredients, wherein the peptide having above 80% homology of amino acid sequence with above-mentioned sequence and the fragment of the same are the peptides that maintain cell penetrating ability of SEQ ID NO: 1.

The mitochondria targeting delivery system of active ingredient according to the one one embodiment of the present invention may comprise any one of conjugates mentioned above, wherein the carrier peptide moves into a mitochondria locally and performs a role of local mitochondria delivering the mentioned active ingredients, wherein the peptide having above 80% homology of amino acid sequence with above-mentioned sequence and the fragment of the same are the peptides that maintain cell penetrating ability of SEQ ID NO: 1.

The composition for modulating mitochondria activity according to the one embodiment of the present invention may comprise any one of conjugates mentioned above, wherein the carrier peptide moves into a mitochondria locally and performs a role of local mitochondria delivering the mentioned active ingredients, wherein the peptide having above 80% homology of amino acid sequence with above-mentioned sequence and the fragment of the same are the peptides that maintain cell penetrating ability of SEQ ID NO: 1.

According to another embodiment of the composition for modulating mitochondria activity in the present invention, the composition may be a pharmaceutical composition for treatment, prophylaxis, suppression of progresses or alleviation of symptoms of diseases or disorders related with mitochondria, and the active ingredients are ingredients for treatment, prophylaxis, suppression of progresses or alleviation of symptoms of diseases or disorders related with mitochondria.

The method according to one embodiment of the present invention may be a method of delivering an active ingredient into a cell, wherein the method comprises a step of administering any one of the above-mentioned conjugate to the subject that is required, and wherein the carrier peptide is a cell penetrating peptide that perform delivery of the active ingredient into a cell, and wherein the peptide having above 80% homology of amino acid sequence with the sequence and the fragment of the sequences may be the peptide that maintain cell penetrating ability of the peptide of SEQ ID NO:1.

According to another embodiment of the method in the present invention, the method may be for delivering the active ingredient locally into mitochondria inside a cell.

The peptide according to the present invention may comprise amino acid sequence of SEQ ID NO: 1, or a fragment of the above-mentioned peptide. The fragment of SEQ ID NO: 1 may be made of 3 to 7 amino acids.

The peptide according to the present invention may be a cell penetrating peptide with more than 17 amino acids comprising SEQ ID NO: 1.

The polynucleotide according to the present invention may encode above-mentioned cell penetrating peptide.

The vector according to the present invention may comprise above-mentioned polynucleotide.

The transformed cell according to the present invention may comprise above-mentioned vector.

INDUSTRIAL APPLICABILITY

Active ingredients which are difficult to be transported inside a cell can be easily transported inside a cell by using the peptide, or the conjugate of the peptide and active ingredients, disclosed in the present invention. This means that efficacy of active ingredients can be increased and therefore the dosage can be lowered. As a result, side effects due to a drug administration can be minimized and effectiveness of treatment can be increased. Especially, as delivering drugs locally into mitochondria, mitochondria related diseases or disorders can be improved, and the effectiveness of prophylaxis and treatment of diseases can be increased. In a case of cosmetics, with a small amount of active ingredients, it can create an outstanding effect. By conjugating a peptide with a contrast substance, it can be used as a contrast substance to monitor a process of cell transplantation or transplanted cells in a cell treatment. Especially, it can be effectively used as a contrast substance for stem cells injected within a body.

DETAILED DESCRIPTION OF THE INVENTION

Figure 1:
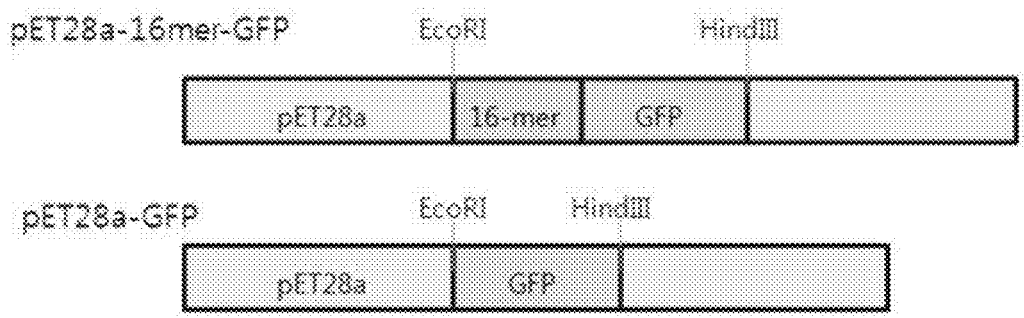
FIG. 1 represents a schematization of green fluorescence protein (GFP) fusion constructs produced in pET28a vector with the restriction enzyme sties (EcoRI & HindIII). 16-mer represents SEQ ID NO: 1 (pep1).
Figure 2:
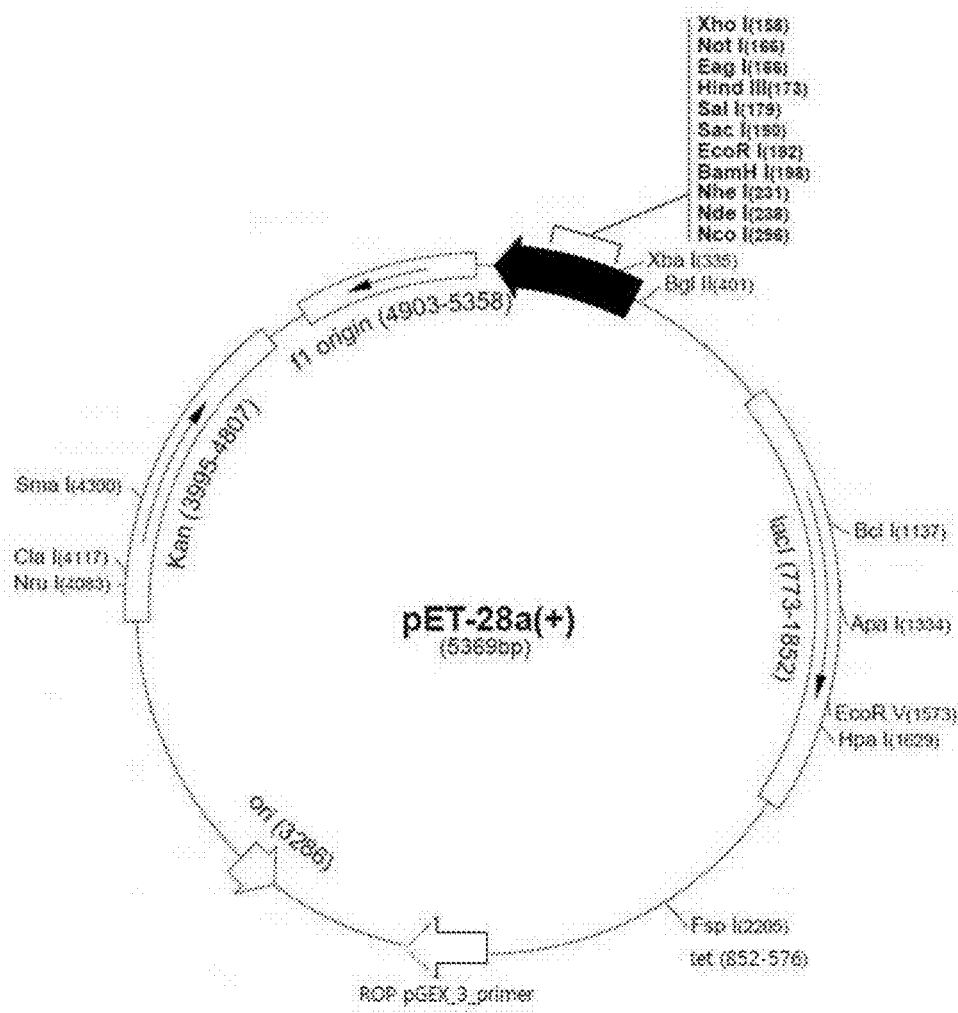
FIG. 2 represents a schematization of pET-28a(+) vector used to generate a fusion construct with SEQ ID NO: 1 (pep1) and Green Fluorescent Protein.
Figure 3:
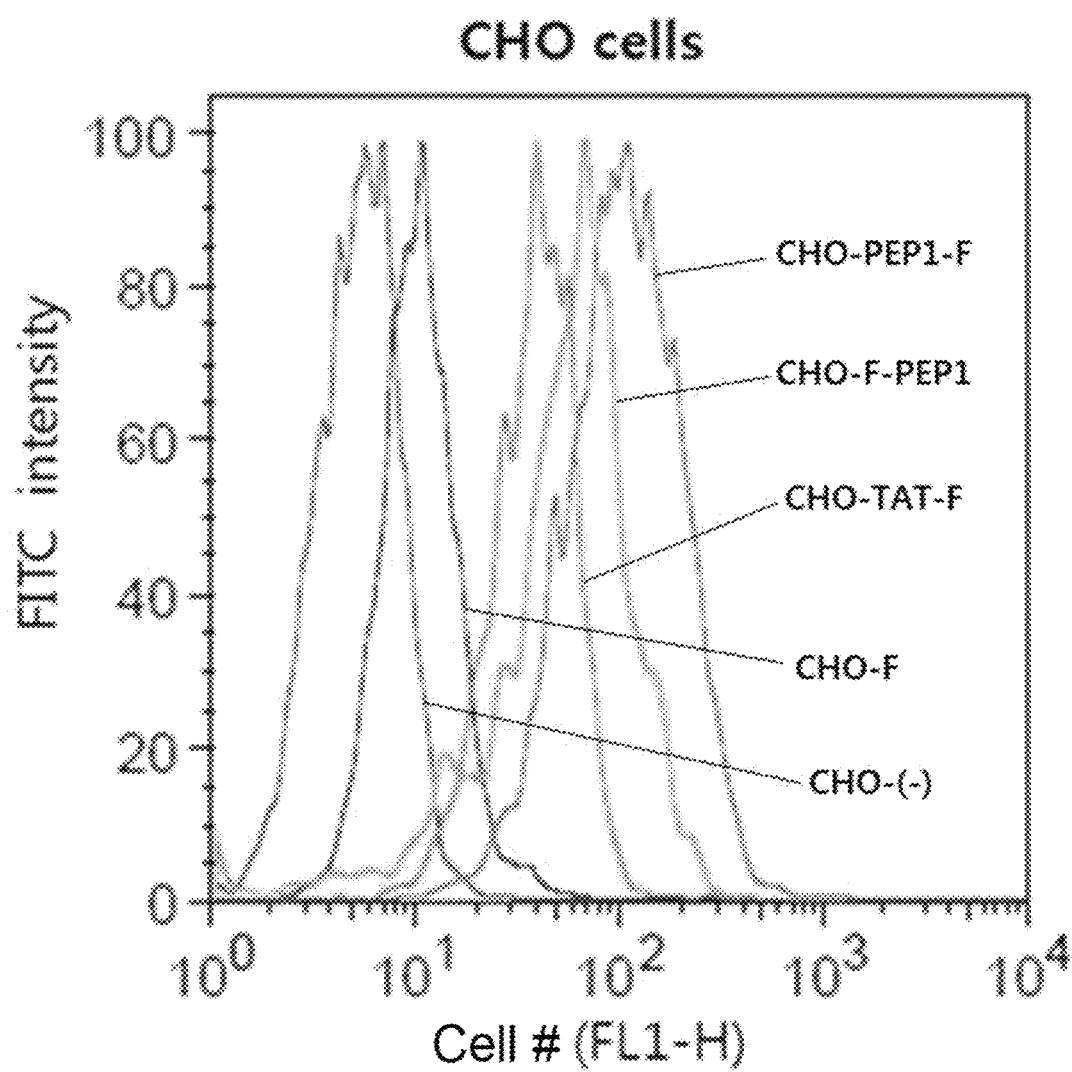
FIG. 3 represents the result of cellular uptake of FITC (CHO-F, control group, blue line), CHO-TAT-F (TAT peptide labeled with FITC, green line), CHO-F-pep-1 (pep1 labeled with FITC at the N-terminal, blue line) and CHO-pep1-F (pep1 labeled with FITC at the C-terminal, pink line) in CHO cells. CHO cells were treated with the peptides as described above for 1 hour, harvested, and analyzed by FACS. The red line represents the background value from CHO cells not treated with any peptide.
Figure 4:
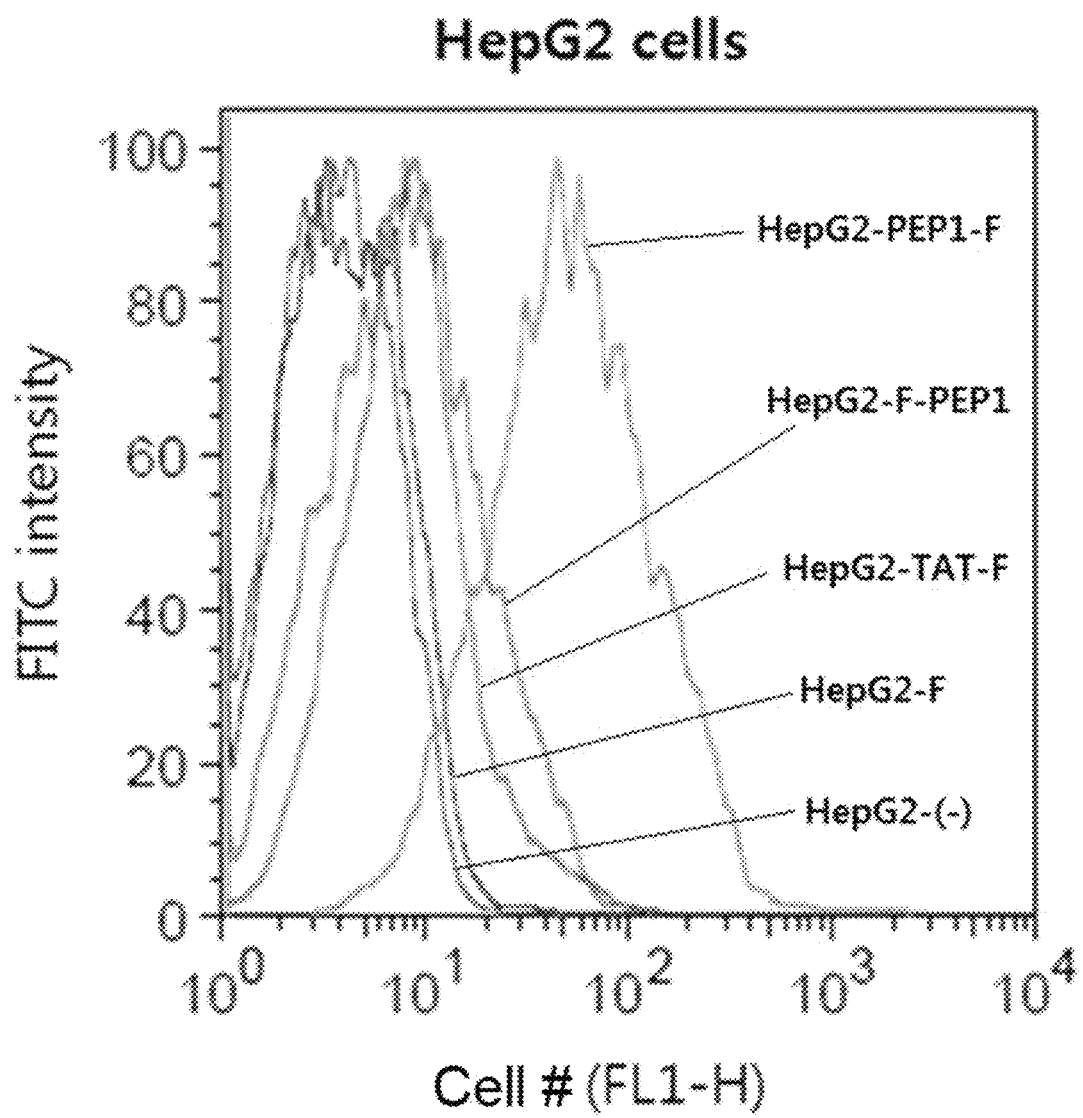
FIG. 4 represents the result of cellular uptake of HepG2 cell line treated with FITC FITC (HepG2-F, control group, blue line), HepG2-TAT-F (TAT peptide labeled with FITC, green line), HepG2-F-pep1 (pep1 labeled with FITC at the N-terminal, orange line), and HepG2-pep1-F (pep1 labeled with FITC at the C-terminal, blue line) in HepG2 cells. Cells were treated with the peptides as described above for 1 hour, harvested, and analyzed by FACS. The red line represents the background value from HepG cells not treated with any peptide.
Figure 5:
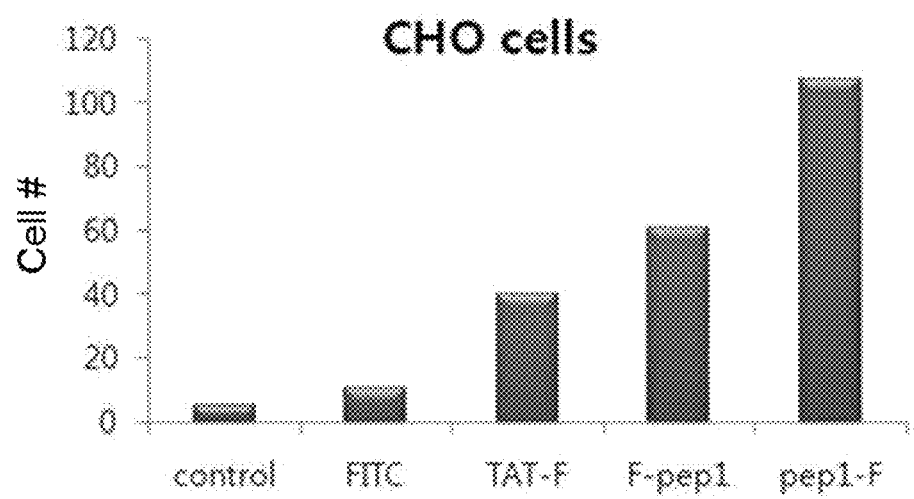
FIG. 5 represents the cellular uptake of TAT-F (TAT labeled with FITC), F-pep1 (pep1 labeled with FITC at the N-terminal), and pep1-F (pep1 labeled with FITC at the C-terminal) in CHO cells by FACS. Cells were treated with the peptides for 1 hour prior to FACS analysis (Control group corresponds to CHO cell line background value).
Figure 6:
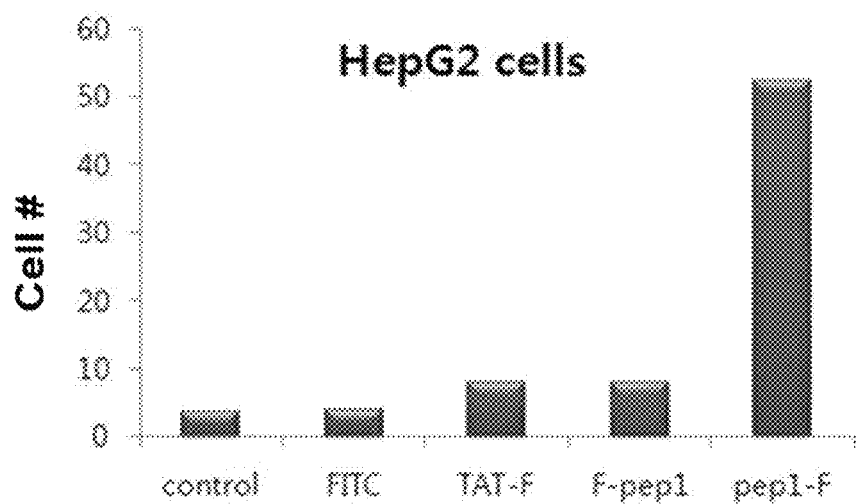
FIG. 6 represents the cellular uptake of TAT-F (TAT labeled with FITC), F-pep1 (pep1 labeled with FITC at the N-terminal), and pep1-F (pep1 labeled with FITC at the C-terminal) in HepG2 cells by FACS. Cells were treated with the peptides for 1 hour prior to FACS analysis (Control group corresponds to HepG2 cell line background value).

The preferred examples of the present invention are as follows.

1. A conjugate of a cell penetrating carrier peptide and an active ingredient, wherein the wherein the carrier peptide is the peptide comprising amino acid sequence of SEQ ID NO: 1, the peptide having above 80% homology with the above-mentioned peptide sequences, or the fragment of the above mentioned peptides,
   wherein the peptide having above 80% homology with the sequence, and the fragment are the peptides that maintain cell penetrating ability of SEQ ID NO: 1.
2. The conjugate according to claim 1, wherein the fragment is made of at least 3 amino acids.
3. The conjugate according to claim 1, wherein the carrier peptide is made of 30 or less amino acids.
4. The conjugate according to claim 1, wherein the carrier peptide is the peptide having amino acid sequence of SEQ ID NO: 1 or the peptide having above 80% homology of amino acid sequence with the above-mentioned sequence.
5. The conjugate according to claim 1, wherein the active ingredient is at least one selected from protein, nucleic acid, peptide, lipid, glycol-lipid, mineral, sugar, nano-particle, biological products, contrast agent, drugs and chemical compounds.
6. The conjugate according to claim 5, wherein the active ingredient is DNA or RNA, and
   wherein the carrier peptide is conjugated with DNA via polylysine when the active ingredient is DNA.

7. The conjugate according to claim 1, wherein the carrier peptide and the active ingredient are combined via a covalent bond, selectively mediated by a linker.

8. The conjugate according to claim 1, wherein the carrier peptide and the active ingredient are combined via non-covalent bond.

9. The conjugate according to claim 5, wherein the active ingredient is a protein or a peptide.

10. The conjugate according to claim 9, wherein the active ingredient is a cytokine, antibody, fragment of antibody, therapeutic enzyme, soluble receptor or ligand.

11. The conjugate according to claim 1, wherein the carrier peptide is combined with fluorescein isothiocyanate.

12. The conjugate according to claim 1, wherein the carrier peptide is combined with Green Fluorescent Protein (GFP).

13. The conjugate according to claim 1, wherein the active ingredient is combined with a C-terminus of the above mentioned carrier peptide.

14. The conjugate according to claim 1, wherein the efficacy target of the active ingredient is cancer cell, immune cell or fibroblast.

15. The conjugate according to claim 14,
wherein the cancer cell is at least one cancer cell selected from the group consisting of liver cancer cell, breast cancer cell and leukemia cell,
wherein the immune cell is at least one immune cell selected from the group consisting of T lymphocytes, B cell and monocyte.

16. The conjugate according to claim 1,
wherein the active ingredient is a substance necessary for localization into cytoplasm, and the carrier peptide performs local delivery of the active ingredient into cytoplasm.

17. The conjugate according to claim 16, wherein the active ingredient is a substance necessary for localization into mitochondria, and the carrier peptide performs local delivery of the active ingredient into mitochondria.

18. The conjugate according to claim 5, wherein the contrast agent is selected from a group consisting of radiopaque contrast agent, paramagnetic contrast agent, superparamagnetic contrast agent and CT contrast agent.

19. The conjugate according to claim 5, wherein the contrast agent is based on iron.

20. The conjugate according to claim 19, wherein the contrast agent is a ferrocene carboxylate.

21. A contrast agent comprising a conjugate of any one of claim 1 to claim 20.

22. The contrast agent according to claim 21, wherein the contrast agent is for contrasting a cell.

23. The contrast agent according to claim 22, wherein the cell is a stem cell.

24. A composition comprising the conjugate according to any one of claim 1 to claim 20 as an active ingredient.

25. The composition according to claim 24, wherein the active ingredient is for treatment or prevention of disease, and the composition is a pharmaceutical composition.

26. The composition according to claim 24, wherein the active ingredient is an active ingredient of functional cosmetics, and the composition is a cosmetic composition.

27. The composition according to claim 24, wherein the active ingredient is an active ingredient of health functional food, and the composition is a health food composition.

28. A cytoplasm targeting delivery system of active ingredient, wherein the delivery system of active ingredient comprises any one conjugate according to claim 1 to claim 20, wherein the carrier peptide is a peptide that moves into a cytoplasm locally and performs a role of local cytoplasm delivering the active ingredient, wherein the peptide having above 80% homology of amino acid sequence with the sequence and the fragment are the peptides that maintain cell penetrating ability of a peptide of SEQ ID NO: 1.

29. A mitochondria targeting delivery system of active ingredient, wherein the delivery system of active ingredient comprises any one conjugate according to claim 1 to claim 20,
wherein the carrier peptide is a peptide that moves into a mitochondria locally and performs a role of local mitochondria delivering the active ingredient, wherein the peptide having above 80% homology of amino acid sequence with the sequence and the fragment are the peptides that maintain cell penetrating ability of a peptide of SEQ ID NO: 1.

30. A composition for modulating mitochondria activity, wherein the composition comprises any one conjugate according to claim 1 to claim 20, wherein the carrier peptide is a peptide that moves into a mitochondria locally and performs a role of local mitochondria delivering the active ingredient, wherein the peptide having above 80% homology of amino acid sequence with the sequence and the fragment are the peptides that maintain cell penetrating ability of a peptide of SEQ ID NO: 1.

31. The composition according to claim 30, wherein the composition is a pharmaceutical composition for treatment, prophylaxis, suppression of progresses or alleviation of symptoms of diseases or disorders related with mitochondria, and wherein the active ingredients are ingredients for treatment, prophylaxis, suppression of progresses or alleviation of symptoms of diseases or disorders related with mitochondria.

32. A method of delivering an active ingredient into a cell, wherein the method comprises a step of administering any one of the above-mentioned conjugate to the subject that is required, wherein the carrier peptide is a cell penetrating peptide that perform delivery of the active ingredient into a cell, and wherein the peptide having above 80% homology of amino acid sequence with the sequence and the fragment of the sequence are the peptides that maintain cell penetrating ability of the peptide of SEQ ID NO:1.

33. The method according to claim 32, wherein the method is for delivering the active active ingredient locally into mitochondria inside a cell.

34. A cell penetrating peptide, wherein the peptide is made of at least 17 amino acid comprising SEQ ID NO: 1.

35. A cell penetrating peptide, wherein the peptide is the fragment of SEQ ID and is made of 3 to 7 amino acids.

36. A polynucleotide that encodes the peptide according to claim 34 or claim 35.

37. A vector that comprises the polynucleotide according to claim 36.

38. A transformed cell that comprises the vector according to claim 37.

Proteins, Nucleic acids, Peptides or virus etc. have big potentials to be used as therapeutic substances. However, their uses are limited because they cannot penetrate tissues and cell membrane due to molecular level sizes. Although, the size of molecules is small, they cannot penetrate lipid-bilayer due to structure or characteristics of the molecules. Thus, through the use of electroporation, heat shock, etc., there were attempts to transport proteins, nucleic acids, peptides or viruses inside the cell; it was difficult to transfer those without neither damaging cell membrane nor keeping the active states of above molecules. There have been many studies conducted since TAT (Trans-Activating Transcriptional activator) protein derived from HIV (Human Immuno-deficiency Virus) has shown to work as cell penetrating peptide which can transport huge active substances inside the cell. Specifically, there have been studies conducted about substances that can transport huge molecules such as proteins, nucleic acids, peptides or virus inside the cell without causing any toxicity, unlike TAT protein which causes toxicity inside the cell. Therefore, the present invention was completed as present inventors have found that peptides derived from telomerase have outstanding efficacy as cell penetrating peptide without a noticeable toxicity.

The peptide described in SEQ ID NO: 1 is same as the following table 1. SEQ ID NO: 2 ID NO: 2 lists the order of full length of human telomerase protein. SEQ ID NO: 1 lists the telomerase-derived peptide that consists of 16 amino acid sequences. The "name" in Table 1 below was used for distinction of peptides. In a different specific embodiment of the present invention, more than one peptide of the mentioned peptides in SEQ ID NO: 1 include "synthetic peptides", the synthesized peptides of selected areas of the telomerase. In the present specification, the term "pep" herein relates to peptides that have SEQ ID NO: 1 or, peptides comprising of amino acid sequence above 80% homology with above-mentioned sequence, or fragments of above-mentioned peptide.

TABLE 1

| SEQ ID No. | Name | PROSITION IN TELOMERASE | SEQUENCE | LENGTH |
|---|---|---|---|---|
| 1. | pep1 | [611-626] | EARPALLTSRLRFIPK | 16 aa |
| 2. | Telomerase | [1-1132] | MPRAPRCRAVRSLLRSHYREVLPLATF VRRLGPQGWRLVQRGDPAAFRALVAQC LVCVPWDARPPPAAPSFRQVSCLKELV ARVLQRLCERGAKNVLAFGFALLDGAR GGPPEAFTTSVRSYLPNTVTDALRGSG AWGLLLRRVGDDVLVHLLARCALFVLV APSCAYQVCGPPLYQLGAATQARPPPH ASGPRRRLGCERAWNHSVREAGVPLGL PAPGARRRGGSASRSLPLPKRPRRGAA PEPERTPVGQGSWAHPGRTRGPSDRGF CVVSPARPAEEATSLEGALSGTRHSHP SVGRQHHAGPPSTSRPPRPWDTPCPPV YAETKHFLYSSGDKEQLRPSFLLSSLR PSLTGARRLVETIFLGSRPWMPGTPRR LPRLPQRYWQMRPLFLELLGNHAQCPY GVLLKTHCPLRAAVTPAAGVCAREKPQ GSVAAPEEEDTDPRRLVQLLRQHSSPW QVYGFVRACLRRLVPPGLWGSRHNERR FLRNTKKFISLGKHAKLSLQELTW KMSVRDCAWLRRSPGVGCVPAAEHRLR EEILAKFLHWLMSVYVVELLRSFFYVT ETTFQKNRLFFYRKSVWSKLQSIGIRQ HLKRVQLRELSEAEVRQHREARPALLT SRLRFIPKPDGLRPIVNMDYVVGARTF RREKRAERLTSRVKALFSVLNYERARR PGLLGASVLGLDDIHRAWRTFVLRVRA QDPPPELYFVKVDVTGAYDTIPQDRLT EVIASIIKPQNTYCVRRYAVVQKAAHG HVRKAFKSHVSTLTDLQPYMRQFVAHL QETSPLRDAVVIEQSSSLNEASSGLFD VFLRFMCHHAVRIRGKSYVQCQGIPQG SILSTLLCSLCYGDMENKLFAGIRRDG LLLRLVDDFLLVTPHLTHAKTFLRTLV RGVPEYGCVVNLRKTVVNFPVEDEALG GTAFVQMPAHGLFPWCGLLLDTRTLEV QSDYSSYARTSIRASLTFNRGFKAGRN MRRKLFGVLRLKCHSLFLDLQ VNSLQTVCTNIYKILLLQAYRFHACVL QLPFHQQVWKNPTFFLRVISDTASLCY SILKAKNAGMSLGAKGAAGPLPSEAVQ WLCHQAFLLKLTRHRVTYVPLLGSLRT AQTQLSRKLPGTTLTALEAAANPALPS DFKTILD | 1132 aa |

The substantial transformation of the biological properties of peptides are performed by selecting significantly different substitution in the following efficacies: (a) the efficacy in maintaining the structure of the polypeptide backbone in the area of substitution, such as sheet or helical three-dimensional structures, (b) the efficacy in maintaining electrical charge or hydrophobicity of the molecule in the target area, or (c) the efficacy of maintaining the bulk of the side chain. Natural residues are divided into groups by general side chain properties as the following:
 (1) hydrophobicity: Norleucine, met, ala, val, leu, ile;
 (2) neutral hydrophilicity: cys, ser, thr;
 (3) acidity: asp, glu;
 (4) basicity: asn, gln, his, lys arg;
 (5) residue that affects chain orientation: gly, pro; and
 (6) aromaticity: trp, tyr, phe.

Non-conservative substitutions may be performed by exchanging a member of the above classes to different classes. Any cystein residues that are not related in maintaining the proper three-dimensional structure of the peptide can typically be substituted into serine, thus increasing the oxidative stability of the molecule and preventing improper crosslinkage. Conversely, improvement of stability can be achieved by adding cysteine bond(s) to the peptide.

Altered types of amino acids variants of peptides are those that antibody glycosylation pattern changed. The term "change" herein relates to deletion of at least one carbohydrate residues that are found in a peptide and/or addition of at least one glycosylated residues that do not exist within a peptide Glycosylation in peptides are typically N-connected or O-connected. The term "N-connected" herein relates to that carbohydrate residues are attached to the side chain of asparagine residues. As tripeptide sequences, asparagine-X-serine and asparagine-X-threonine (where the X is any amino acid except proline) are the recognition sequence for attaching carbohydrate residue enzymatically to the side chain of asparagine. Therefore, with the presence of one of these tripeptide sequences in a polypeptide, the potential glycosylation sites are created. "O-connected glycosylation" means attaching one of sugar N-acetylgalactosamine, galactose, or xylose to hydroxyl amino acids. The hydroxyl amino acids are most typically serine or threonine, but 5-hydroxyproline or 5-hydroxylysine can be used.

Addition of glycosylation site to a peptide is conveniently performed by changing amino acid sequence to contain tripeptide sequence mentioned above (for N-linked glycosylation sites). These changes may be made by addition of at least one serine or threonine residues to the first antibody sequence, or by substitution with those residues (for O-linked glycosylation sites).

In one embodiment of the present invention, cell penetrating peptide comprising a peptide, wherein the peptide comprises amino acid sequence of SEQ ID NO: 1, the peptide has above 80% homology for amino acid sequence with above-mentioned sequence, or peptide is a fragment of above-mentioned peptide, is provided. In one embodiment of the present invention, a pharmaceutical composition comprising peptide as a drug delivery system to transport more than one active ingredient is provided, wherein the peptide comprises amino acid sequence of SEQ ID NO: 1, the peptide has above 80% homology with above-mentioned sequence, or the peptide is a fragment of above-mentioned peptide. A peptide comprising amino acid sequence of SEQ ID NO: 1, a fragment of above-mentioned peptide, or a peptide having above 80% homology with above-mentioned sequence, is safe and has outstanding efficacy as cell penetrating peptide. Therefore, the peptide can be conjugated with a drug to transport the drug inside the cell.

In one embodiment of the present invention, a conjugate of a peptide and an active active ingredient to be transported is provided, wherein the peptide comprises amino acid sequence of SEQ ID NO: 1, the peptide is a fragment of above-mentioned peptide, or the peptide has above 80% homology with above-mentioned peptide. In one embodiment of the present invention, an active ingredient may be at least one selected from proteins, nucleic acids, peptides, lipids, glycolipids, minerals, sugars, contrast substances, drugs and chemical compounds. In one embodiment of the present invention, the active ingredients may be peptides. In one embodiment of the present invention, the active ingredients may be cytokines, antibody, antibody fragments, therapeutic enzymes, soluble receptors, or ligands.

A cell penetrating peptide disclosed herein means a peptide which can transport cargo from in vitro and/or in vivo to inside the cell. A "cargo" disclosed herein comprises all the substances that can be transported inside the cell via conjugation with a cell penetrating peptide, For example, all the substances which want to increase cell penetrating efficacy, specifically drugs, cosmetics, or active ingredients of health food, more specifically substances which cannot be transported inside the cell via general route, more specifically, sugars, nano-particles, biological formulation, viruses, contrast substances or other chemical compounds which can have proteins, nucleic acids, peptide, minerals, glucose as an example, but not limited to those. A "drug" disclosed herein is a broad concept including a substance to be transported for alleviation, prophylaxis, treatment or diagnosis of diseases, wounds, or specific symptom.

A "carrier peptide" disclosed herein is a peptide which can transport active ingredients to a targeted site via conjugation with active ingredients.

In one embodiment of the present invention, protein or peptide as a cargo comprises one or more of hormone, hormone analogue, enzyme, enzyme inhibitors, signal transfer proteins(or peptides), antibody and vaccine, but not limited to those. In one embodiment of the present invention, a nucleic acid is a molecule that can be spontaneous or artificial DNA or RNA molecules, either single-stranded or double-stranded. The nucleic acid molecule can be one or more nucleic acids of same type (for example, having a same nucleotide sequence) or nucleic acids of different types. The nucleic acid molecules comprise one or more DNA, cDNA, decoy DNA, RNA, siRNA, miRNA shRNA, stRNA, snoRNA, snRNA PNA, antisense oligomer, plasmid and other modified nucleic acids, but not limited to those. In one embodiment of the present invention, virus comprises the whole virus or the core of virus which includes nucleic acids of the virus. In one embodiment of the present invention, a chemical substance is a broad indication comprising a natural or synthetic substance which can act as a drug.

A phenomenon where specific DNA expression is controlled by double stranded RNA RNA (dsRNA) in a process of DNA expression is called RNA interference; RNAi. Since the phenomenon was first discovered in *C. elegans* in 1998, it was found that the phenomenon is common in plants, fruit flies and mammals (Fire et al., Nature, 391:806-811, 1998; Novina & Sharp, Nature, 430:161-164, 2004).

RNA interference is mediated by dsRNA having 19-25 bps that enters the cells, upon which it combines with RISC (RNA-induced silencing complex). The binding of the antisense strand of dsRNA to the complementary mRNA sequence triggers degradation of the target mRNA by the endonuclease enzyme found in RISC complex. (Rana, T. M., Nat. Rev. Mol. Cell Biol., 8:23-36, 2007; Tomari, Y. and Zamore, P. D., Genes Dev., 19: 517-529, 2005). In other words, siRNA is involved in RNA interference by suppressing production of specific protein and thereby interfering with DNA expression. siRNA consisting of 19~23 nucleotides, forms a base pair according to complementary order of mRNA for specific messenger RNA (mRNA) to form double-stranded RNA. After then, the double-stranded RNA is specially disintegrated at the same time messenger RNA is removed from the cells. siRNA has been spotlighted as a substance for gene therapy because it showed an outstanding effect in suppressing expression of specific DNA in recent animal studies. siRNA with higher activation and precise selection of DNA, has been studied for last 20 years and it is expected to replace the antisense oligonucleotides which is currently being used as a remedy. Therefore, many pharmaceutical companies are now developing a siRNA based remedy. Compared to the existing anti-sense oligonucleotides, siRNA is known to inhibit gene expression with 10 times less amount and inhibit target genes only with an outstanding selectivity of genes. siRNA technique, especially for the treatment purpose, has a great advantage as it can be easily designed compared to other drugs and has characteristics such as high target selectivity and inhibition of specific gene expression. Also, since suppression of gene expression by RNA interference utilizes the mechanism naturally present in vivo, toxicity is low. However, siRNA has a disadvantage that it cannot be easily transported into a cell as it cannot penetrate the cell membrane as it is anionic and easily broken down in a short period of time due to low stability in vivo. This disadvantage of siRNA can be solved by conjugating with a carrier peptide disclosed herein.

In one embodiment of the present invention, the efficacy of active ingredients, the cargo, the cargo, are cancer cells, immune cells or fibroblast cells. Specifically, above cancer cells comprise any one cancer cell selected from the group consisting of: liver cancer cells, breast cancer cells and leukemia cells, above immune cells comprise any one immune cell selected from the group consisting of: T lymphocyte, B cells and monocytes.

In one embodiment of the present invention, above active ingredients are to be localized in the cytoplasm, and the carrier peptide transports above active ingredients to cytoplasm locally.

In one embodiment of the present invention, above active ingredients are to be localized in mitochondria, and the carrier peptide transports above active ingredients to mitochondria locally.

In one embodiment of the present invention, drugs transported inside the cell by cell penetrating peptide can comprise one or more drug transporters such as liposome, micelle, nano-particles, magnetic-particles or Quantum Dot.

The term "contrast substance" disclosed herein is a broad indication comprising all the all the substances used to contrast structures or fluids within the body in medical imaging. An appropriate contrast substance comprises radiopaque contrast agent, paramagnetic contrast agent, superparamagnetic contrast agent, CT (computed tomography) and other contrast substances, but not limited to those. For example, a radiopaque contrast agent (for x-ray imaging) will comprise inorganic iodine compound and organic iodine compound (for example, diatrizoate), radiopaque metals and their salts (for example, silver, gold, platinum, etc.) and other radiopaque compounds (for example, calcium salts, barium salt such as barium sulfate, tantalum and oxidized tantalum). An appropriate paramagnetic contrast substance (for MR imaging) comprises gadolinium diethylene triaminepentaacetic acid (Gd-DTPA) and its derivatives, other gadolinium, manganese, iron, dysprosium, copper, europium, erbium, chrome, nickel and cobalt complex, for example, 1,4,7,10-tetraazacyclododecan-N,N',N'',N'''-tetraacetic acid (DOTA), ethylenediaminetetraacetic acid (EDTA), 1,4,7,10-tetraazacyclododecan-N,-N', N''-triacetic acid (DO3A), 1,4,7-triazacyclononane-N,N',N''-TRI-ACETIC ACID (NOTA), 1,4,8,10-tetraazacyclotetradecane-N,N',N'',N'''-tetraacetic acid (TETA), hydroxybenzylethylene-diamine diacetic acid (HBED). An appropriate superparamagnetic contrast substance (for MR imaging) comprises magnetite, super-paramagnetic iron oxide(SPIO), ultrasmall superparamagnetic iron oxide(USPIO) and monocrystailine iron oxide. Other appropriate contrast substances are iodinated, non-iodinated, ionic and non-ionic CT contrast agents, a contrast substance like spin-label or diagnostically effective agent.

Other examples of contrast substances comprise β-galactosidase, Green Fluorescent Protein, Cyan Fluorescent Protein, luciferase, but not limited to those, and a marker gene which codes for protein which can be easily detected when expressed within cells. Various labels such as radionuclide, flour, enzyme, enzyme-substrate, enzyme cofactor, enzyme inhibitor, ligands (especially hapten) can be used.

In one example of the present invention, a contrast substance is ferrocenecarboxylic acid of the below chemical formula 2. The structure of ferrocene is shown in the chemical formula 1.

[Chemical Formula 1]

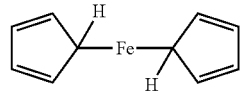

[Chemical formula 2]

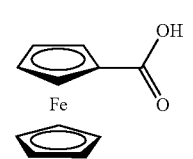

In one example of the present invention, a conjugate of cell penetrating peptide and a contrast substance is Ferrocenecarboxylic-pep1 shown in the below chemical formula 3.

[Chemical formula 3]

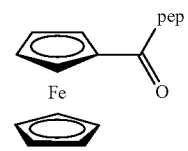

In one embodiment of the present invention, a peptide or composition can be fused with fused with one or more detectable labels. Labels may be compounds which can be detected in chemical, physical or enzymatic responses, or compounds which generate signals directly or indirectly in the responses. Labeling and detecting after then can be performed according to the known method in the art (For example, Sambrook, J., and Russel, D. W. (2001); and Lottspeich, F., and Zorbas H. (1998) Bioanalytik, Spektrum Akademischer Verlag, Heidelberg/Berlin, Germany). Labels comprise fluorescent label, enzyme label, chromogenic label, luminescence label, radiation label, hapten, biotin, metal complex, metal and colloidal gold, but not limited to those. All forms of these labels are well known in this field of work, they can be commercially obtained from various suppliers.

In one embodiment of the present invention, a cargo can be directly combined with the peptide. In another embodiment of the present invention, a cargo can be combined to the peptide via various types of bonds such as covalent or non-covalent bonds. A cargo, for example, can be combined to the N-terminal or C-terminal of the peptide in one embodiment of the present invention. For example, a cargo can be bonded to the peptide by disulfide bonds or covalent bonds. The covalent bonds are the bonds that a cargo can be bonded to α-amine of N-terminal glutamate, or amine of C-terminal Lysine residues. Also, a peptide and a cargo can be combined via a non-covalent bond, which can have either a peptide or a cargo can encapsulate the other as a capsule form.

In another embodiment of the present invention, a peptide can be combined with a cargo via a linker. For example, a peptide can be combined with a cargo by binding a cargo to a linker after introducing a linker such as Hynic(6-hydrazinopyridine-3-carboxylic acid) linker, to the α-amine of N-terminal glutamate, or amine of C-terminal Lysine residues.

In another embodiment of the present invention, when a cargo is DNA or RNA, SH group (thiol group) is introduced to the peptide, and maleimide group is introduced to DNA or RNA, then, SH group of the peptide and maleimide group of DNA or RNA are combined, thus creating a bond between the cargo and the peptide.

In another embodiment of the present invention, when a cargo is a peptide or protein, protein, DNA which expresses a cargo is combined with DNA which expresses a carrier peptide, and by expressing this, a cargo and a peptide can be combined as a form of fusion protein. Specific examples of combination by a fusion protein are as follows: when manufacturing primer for production of fusion protein, a nucleotide coding a carrier peptide is attached in front of a nucleotide expressing a cargo, and the obtained nucleotide is inserted to a vector such as pET vector using a restriction enzyme, and the nucleotide is expressed by transformation into a cell such as BL-21(DE3). At this time, a fusion protein is to be effectively expressed by treating it with an expression inducing agent like IPTG (isopropyl-1-thio-β-D-galactopyranoside). Then, the expressed fusion protein is purified by His tag purification, and is dialyzed with PBS, and is added to a kit to be concentrated by centrifugation under such condition for 5 to 20 mins at 2,000 to 4,000 rpm.

In one embodiment of the present invention, a carrier peptide is combined with dying substances, fluorescent substances, specifically FITC (fluorescein isothiocyanate) or GFP (Green Fluorescent Protein). In one embodiment of the present invention, FITC is combined with amino group ($NH^{3'}$) of lysine at N-terminal or C-terminal of a carrier peptide. In the case of a peptide, where lysine does not exist at its terminal, the peptide can be combined with FITC via a linker including Lysine.

The carrier peptide disclosed herein which is the peptide comprising amino acid sequence of SEQ ID NO: 1, or the peptide having above 80% homology of amino acid sequence with above-mentioned peptides, or a fragment of above-mentioned peptide, can be combined with a cargo at a mole fraction of 1:1, but it can be combined at mole fraction other than 1:1. For example, a mole fraction of CPP and a cargo may be more than 2:1, specifically, more than 2:1, more than 3:1, more than 4:1, more than 5:1, more than 6:1, more than 7:1, more than 8:1, more than 9:1 or more than 10:1. This means that numerous carrier peptide molecules can be combined with a cargo molecule. The numerous carrier peptide molecules can be combined in series or in parallel. "Combined in series" means that a carrier peptide and a cargo molecule are to be combined at terminal amino acids. "Combined in parallel" means that they are to be combined at a site other than terminal amino acids. On the other hand, the mole fraction of a carrier peptide and a cargo may be more than 1:2. This means that a carrier peptide molecule can be combined with numerous number of a cargo molecule. For example, a mole fraction of a carrier peptide and a cargo may be 1:2, specifically, more than 1:2, more than 1:3, more than 1:4, more than 1:5, more than 1:6, more than 1:7, more than 1:8, more than 1:9 or more than 1:10.

A movement pathway of the peptide combined with Fluorescein isothiocyanate can be can be easily found. Therefore, a carrier peptide in one embodiment of the present invention is to be used for cell imaging or detecting a pathway of drug delivery inside a cell.

In one embodiment of the present invention, a use of the peptide as a drug delivery carrier to transport more than one active ingredient is provided, wherein the peptide comprises amino acid sequence of SEQ ID NO: 1, or the peptide is a fragment of above-mentioned peptide, or the peptide has above 80% homology of amino acid sequence with above-mentioned peptide. The use may indicate therapeutic or non-therapeutic use.

In one embodiment of the present invention, a method of delivering drugs inside a cell of a subject comprising a step of administering a composition comprising a drug; and the peptide is provided; wherein the peptide comprises amino acid sequence of SEQ ID NO: 1, or the peptide is a fragment of above-mentioned peptide, or the peptide has above 80% homology of amino acid sequence with above-mentioned peptide.

In one embodiment of the present invention, a method of detecting drug delivery pathway comprising a step of applying the peptide and a contrast substance to a subject is provided; wherein the peptide comprises amino acid sequence of SEQ ID NO: 1, or the peptide is a fragment of above-mentioned peptide, or the peptide has above 80% homology of amino acid sequence with above-mentioned peptide.

In one embodiment of the present invention, a method of detecting drug delivery pathway comprising a step of applying of the conjugate of the peptide and a contrast substance to a subject is provided; wherein the peptide comprises amino acid sequence of SEQ ID NO: 1, or the peptide is a fragment of above-mentioned peptide, or the peptide has above 80% homology of amino acid sequence with above-mentioned peptide.

In one embodiment of the present invention, a kit for drug delivery into a cell of a subject containing the composition and an instruction is provided, wherein the composition comprises a conjugate of a peptide of the invention and a drug for delivery, wherein the peptide comprises amino acid sequence of SEQ ID NO: 1 or the peptide is a fragment of above-mentioned peptide, or the peptide has above 80% homology of amino acid sequence with above-mentioned peptide, wherein the instruction includes at least one of administration dose, administration route, administration frequency, and indication of the composition.

In one embodiment of the present invention, cosmetic or food composition comprising comprising an active ingredient; and the peptide is provided; wherein the peptide comprises amino acid sequence of SEQ ID NO: 1, the peptide has above 80% homology of amino acid sequence with above-mentioned sequence, or the peptide is a fragment of the above-mentioned peptides. In another embodiment of the present invention, cosmetic or food composition comprising a conjugate of the peptide and active ingredients is provided; wherein the peptide comprises amino acid sequence of SEQ ID NO: 1, the peptide has above 80% homology of amino acid sequence with above-mentioned sequence, or the peptide is a fragment of the above-mentioned peptides.

In one embodiment of the present invention, pharmaceutical, cosmetic or food composition with an outstanding ability to transport active ingredients inside a cell, comprising a conjugate of the peptide and an active ingredient, is provided; wherein the peptide comprises amino acid sequence of SEQ ID NO: 1, the peptide has above 80% homology of amino acid sequence with above-mentioned sequence, or the peptide is a fragment of the above-mentioned peptides.

Mitochondria, as a central organelle in energy metabolism of a eukaryotic cell, is a first known intracellular organelle to be related to human diseases (Luft R, Ikkos D, Palmieri G, Ernster L, Afzelius B: A case of severe hypermetabolism of non thyroid origin with a defect in the maintenance of mitochondrial respiratory control: a correlated clinical, biochemical, and morphological study, J. Clin. Invest. 41: 1776-804, 1962).

Since the mitochondria play an important role in control of energy metabolism of cell and apoptosis, they act as a major target for various therapeutic drugs. Also, this organelle is involved in control of the calcium concentration inside the cell, the mitochondrial respiratory chain acts as an electron transport system which is important in energy production, and it causes production of reactive oxygen species. As a result, the abnormal mitochondrial function has a close relationship with adult diseases such as diabetes, cardiomyopathy, infertility, blindness, renal/liver diseases, and stroke (Modica-Napolitano K S, Singh K K: April mitochondria as targets for detection and treatment of cancer. Expert Rev Mol Med 11:1-19, 2002). Also, it is being suggested that Mitochondrial genetic mutations to be involved in the outbreak of aging, degenerative neuronal disease and cancer etc.

The "Mitochondrial related diseases" disclosed herein comprise Huntington's disease, amyotriophic lateral sclerosis, MELAS (Mitochondrial Encephalomyopathy with Lactic Acidemia and Stroke-like episodes); MERRF (Myoclonus, epilepsy, and myopathy with ragged red fibers; NARP/MILS (Neurogenic muscular weakness, ataxia, retinitis pigmentosa/Maternally inherited leigh syndrome); LHON (Lebers hereditary optic neuropathy); KSS (Kearns-Sayre Syndrome); PMPS (Pearson Marrow-Pancreas Syndrome); CPEO (Chronic progressive external opthalnoplegia); Reye's syndrome; Alper's syndrome; Multiple mtDNA deletion syndrome; mtDNA depletion syndrome; Complex I deficiency; Complex II (SDH) deficiency; Complex III deficiency; Cytochrome c oxidase (COX, Complex IV) deficiency; Complex V deficiency; Adenine nucleotide translocator (ANT) deficiency; Pyruvate dehydrogenase (PDH) deficiency; Ethyl malonic acid aciduria having lactic acid acidemia; 3-methyl glutaconic acid aciduria having lactic acid acidemia; refractoriness epilepsy representing a decline during infection; Asperger's syndrome representing a decline during infection; Autism representing a decline during infection; Attention deficit hyperactivity disorder (ADHD); Cerebral palsy representing a decline during infection; Alexia representing a decline during infection; Maternal hereditary thrombocytopenia; Leukemia; MNGIE (Mitochondrial myopathy, peripheral and autonomic neuropathy, gastrointestinal dysfunction, and epilepsy); MARIAHS syndrome (Mitochondrial ataxia, recrudescent infection, aphasia, hypouricemia/hypomyelination, seizure and dicarboxylic acid aciduria); ND6 dystonia; Cyclic vomiting syndrome representing a decline during infection; 3-hydroxyisobutyric acid aciduria having lactic acid acidemia; Diabetes having lactic acid acidemia; Uridine reactive neural syndrome (URNS); Familial bilateral striatum necrosis (FBSN); Hearing loss related with aminoglycoside; Relaxed myocardiopathy; Spleen lymphoma; Wolframs syndrome; Multiple mitochondria DNA deletions syndrome; and Renal tubular acidosis/diabetes/ataxia syndrome, but not limited to those.

In another embodiment of the present invention, nucleic acid molecules encoding above-encoding above-mentioned polypeptides are provided. The nucleic acid molecules, for example, have base sequences of GAA GCG CGC CCG GCG CTG CTG ACC AGC CGC CTG CGC TTT ATT CCG AAA. The nucleic acids can be introduced into the host cell according to a known method to those skilled in the art. For example, the known methods may be transformation method by calcium phosphate method, liposome, electroporation, contacting a virus and a cell, or micro injection directly into the cell, etc. The host cell is higher eukaryotic cell, for example, mammalian cells, or lower eukaryotic cells, such as a yeast cell, or prokaryotic cells, such as a bacterial cell. The prokaryotic host cells appropriate for transformation may be the species which belong to *E. coli, Bacillus subtillis, Salmonella typhimurium, Pseudomonas, Streptomyces,* and Micro bacteria species, as examples.

The vector including above-mentioned nucleic acid molecules is generally recombinant recombinant expression vector and it comprises, origin of replication enabling a host cell transformation, and a selectable marker (for example, dihydrofolate reductase for eukaryotic cell culture, or tolerance of neomycin, tolerance of tetra-cycline or ampicillin in *E. coli*, or *S. cerevisiae* TRP1 gene), and the promoter for controlling transcription of protein coating sequences. Available expression vectors are, for example, known bacterial plasmids such as SV40, derivatives of pcDNA, and known bacterial plasmids such as colE1, pCR1, pBR322, pMal-C2, pET, pGEX (Smith, et al., Gene 67:31-40(1988)), plasmids such as pMB9 and its derivative RP4, phage DNA which is the same as numerous derivatives of phage I such as NM989, phage DNA such as M13 and single-stranded phage DNA of filament type; yeast plasmid, for example, phage DNA or vector induced from a combination of modified plasmid for using expression suppression sequences and phage DNA. The mammalian expression vectors comprise origin of replication, an appropriate promoter and an enhancer. Also, they can comprise compulsory ribosome binding sites, polyadenylation sites, splice donor, and receptor part, transcription termination sequences, and 5' planking non-transcriptional sequences. The mammalian expression vectors can comprise an inducible promoter, for example, a vector containing dihydrofolate reductase promoter, any expression vectors containing DHFR expression cassette or DHFR/methotrexate co-amplification vector such as pED. (Randal J. Kaufman, 1991, Randal J. Kaufman, Current Protocols in Molycular Biology, 16, 12(1991)). Or, glutamine synthetase/methionine sulfoximine co-amplification vector, for example, pEE14(Celltech), Epstein-Barr-Virus (EBV), or a vector directing episomal expression under the control of nuclear antigen (EBNA), for example, pREP4 (Invitrogen), pCEP4(Invitrogen), pMEP4(Invitrogen), pREP8(Invitrogen), pREP9(Invitrogen) and pEBVHis(Invitrogen) can be used. Selectable mammalian expression vectors are Rc/CMV(Invitrogen) and pRc/RSV(Invitrogen) etc. Vaccinia virus mammalian expression vectors which can be used in the present invention are pSC11, pMJ601, pTKgptF1S, etc.

Yeast expression vector system to be used in the present invention is non-fusion pYES2 vector(Invitrogen), fusion pYESHisA, B, C(Invitrogen), pRS vector, etc.

The above-mentioned vectors can be introduced to various cells, such as mammalian cells which is especially the human derived cells, or bacteria, yeast, fungi, insects, nematodes, and plant cells. The examples of appropriate cells are VERO cell, HELA cell, for example, ATCC No. CCL2, CHO cell line, for example, ATCC No. CCL61, COS cell, for example COS-7 cell and ATCC No. CRL 1650 cell, W138, BHK, HepG2, 3T3, for example, ATCC No. CRL6361, A549, PC12, K562 cell, 293 cell, Sf9 cell, for example, ATCC No. CRL1711 and Cvl cell, such as ATCC No. CCL70, etc.

Other appropriate cells to be used in the present invention are prokaryotic host cell strain, for example, the strains belonging to *E. coli* (e.g. DH5-α strain), *Bacillus subtilis, Salmonella typhimurium, Pseudomonas, Streptomyces* and *Staphylococcus*.

In one embodiment of the present invention, the composition may contain 0.1 μg/mg to 1 mg/mg, specifically 1 μg/mg to 0.5 mg/mg, more specifically 10 μg/mg to 0.1 mg/mg of a peptide comprising amino acid sequence of at least one of SEQ ID NO: 1, a peptide comprising amino acid sequence above 80% homology with above-mentioned sequence, or a fragment of above-mentioned peptide. When the peptide is contained in the above-mentioned range, all the safety and stability of the composition can be satisfied and appropriate in terms of cost-effectiveness.

In one embodiment of the present invention, the composition may have application with all animals including human, dog, chicken, pig, cow, sheep, guinea pig, and monkey.

In one embodiment of the present invention, the pharmaceutical composition may be administered through oral, rectal, transdermal, intravenous, intramuscular, intraperitoneal, in the bone marrow, epidural or subcutaneous means.

Forms of oral administration may be, but not limited to, tablets, pills, soft or hard capsules, granules, powders, solution, or emulsion. Forms of non-oral administration can be, but not limited to, injections, drips, lotions, ointments, gels, creams, suspensions, emulsions, suppository, patch, or spray.

In one embodiment of the present invention, the pharmaceutical composition, if necessary, may contain additives, such as diluents, excipients, lubricants, binders, disintegrants, buffers, dispersants, surfactants, coloring agents, aromatics or sweeteners. In one embodiment of the present invention, the pharmaceutical composition may be manufactured by conventional methods of the industry in the art.

In one embodiment of the present invention, the active ingredient of the medical composition may vary according to the patient's age, sex, weight, pathology and state, administration route, or prescriber's judgment. Dosage based on these factors is determined within levels of those skilled in the art, and the daily dose for example may be, but not limited to, 0.1 μg/kg/day to 1 g/kg/day, specifically 1 μg/kg/day to 10 mg/kg/day, more specifically the 10 μg/kg/day to 1 mg/kg/day, more specifically the 50 μg/kg/day to 100 μg/kg/day. In one embodiment of the present invention, the pharmaceutical composition may be administered, but not limited to, 1 to 3 times a day.

In one embodiment of the present invention, cosmetic composition may be provided in all forms appropriate for topical applications. For example, forms may be provided as solutions, emulsions obtained by dispersion of oil phase in water, emulsion obtained by dispersion of water in oil phase, suspension, solid, gel, powder, paste, foam or aerosol. These forms may be manufactured by conventional methods of the industry in the art.

In one embodiment of the present invention, the cosmetic composition may include, within levels that won't harm the main effect, other ingredients that may desirably increase the main effect. In one embodiment of the present invention, the cosmetic composition may additionally include moisturizer, emollient agents, surfactants, UV absorbers, preservatives, fungicides, antioxidants, pH adjusting agent, organic or inorganic pigments, aromatics, cooling agent or antiperspirant. The formulation ratio of the above-mentioned ingredients may be decided by those skilled in the art within levels that won't harm the purpose and the effects of the present invention, and the formulation ratio based on total weight of the cosmetic composition may be 0.01 to 5% by weight, specifically 0.01 to 3% by weight.

In one embodiment of the present invention, food composition is not limited to forms, but for example may be granules, powder, liquid, and solid forms. Each form may be formed with ingredients commonly used in the industry appropriately chosen by those skilled in the art, in addition to the active ingredient, and may increase the effect with other ingredients.

Decision for dosage on the above-mentioned active ingredient is within the level of those of those skilled in the art, and daily dosage for example may be 1 μg/kg/day to 10 mg/kg/day, more specifically the 10 μg/kg/day to 1 mg/kg/day, more specifically the 50 μg/kg/day to 100 μg/kg/day, but not limited to these numbers and can vary according to age, health status, complications and other various factors.

The terms used herein is intended to be used to describe the embodiments, not to limit limit the present invention. Terms without numbers in front are not to limit the quantity but to show that there may be more than one thing of the term used. The term "including", "having", "consisting", and "comprising" shall be interpreted openly (i.e. "including but not limited to").

Mention of range of numbers is used instead of stating separate numbers within the range, so unless it is explicitly stated, each number can be read as separate numbers integrated herein. The end values of all ranges are included in the range and can be combined independently.

Unless otherwise noted or clearly contradicting in context, all methods mentioned herein can be performed in the proper order. The use of any one embodiment and all embodiment, or exemplary language (e.g., that use "like ~"), unless included in the claims, is used to more clearly describe the present invention, not to limit the scope of the present invention. Any language herein outside of the claims should not be interpreted as a necessity of the present invention. Unless defined otherwise, technical and scientific terms used herein have meaning normally understood by a person skilled in the art that the present invention belongs to.

The preferred embodiments of the present invention are the best mode known to the inventors to perform the present invention. It can become clear to those skilled in the art after reading the statements ahead of the variations in the preferred embodiments. The present inventors hope that those skilled in the art can use the variations adequately and present invention be conducted in other ways than listed herein. Thus, the present invention, as allowed by the patent law, includes equivalents, and variations thereof, of the key points of the invention stated in the appended claims. In addition, all possible variations within any combination of the above-mentioned components are included in the present invention, unless explicitly stated otherwise or contradicting in context. Although the present invention is described and shown by exemplary embodiments, those skilled in the art will understand well that there can be various changes in the form and details without departing from the spirit of the invention and range, defined by the claims below.

Example 1: Synthesis of Peptide

The peptide with SEQ ID NO: 1 was synthesized according to the existing method of method of solid phase peptide synthesis. In detail, the peptides were synthesized by coupling each amino acid from C-terminus through Fmoc solid phase peptide synthesis, SPPS, using ASP48S (Peptron, Inc., Daejeon ROK). Those peptides with their first amino acid at the C-terminus being attached to resin were used as follows:

NH$_2$-Lys(Boc)-2-chloro-Trityl Resin
NH$_2$-Ala-2-chloro-Trityl Resin
NH$_2$-Arg(Pbf)-2-chloro-Trityl Resin All the amino acid materials to synthesize the peptide were protected by Fmoc at the N-terminus, and the amino acid residues were protected by Trt, Boc, t-Bu (t-butylester), Pbf (2,2,4,6,7-pentamethyl dihydro-benzofuran-5-sulfonyl) that can be dissolved in acid. Such as:

Fmoc-Ala-OH, Fmoc-Arg(Pbf)-OH, Fmoc-Glu(OtBu)-OH, Fmoc-Pro-OH, Fmoc-Leu-OH, Fmoc-Ile-OH, Fmoc-Phe-OH, Fmoc-Ser(tBu)-OH, Fmoc-Thr(tBu)-OH, Fmoc-Lys(Boc)-OH, Fmoc-Gln(Trt)-OH, Fmoc-Trp(Boc)-OH, Fmoc-Met-OH, Fmoc-Asn(Trt)-OH, Fmoc-Tyr(tBu)-OH, Fmoc-Ahx-OH, Trt-Mercaptoacetic acid.

HBTU[2-(1H-Benzotriazole-1-yl)-1,1,3,3-tetramethylaminium hexafluorophosphate]/HOBt [N-Hydroxybenzotriazole]/NMM [4-Methylmorpholine] were used as the coupling reagents. In 20% of DMF, piperidine was used to remove Fmoc. In order to remove the protection from residue or to separate the synthesized peptide from Resin, cleavage cocktail [TFA (trifluoroacetic acid)/TIS (triisopropylsilane)/EDT (ethanedithiol)/H$_2$O=92.5/2.5/2.5/2.5] was used.

Peptides were synthesized by using the solid phase scaffold by adding each amino acid with the sequential proesses as follow; amino acid protection, coupling reaction, washing, and deprotection. After cutting off the synthesized peptide from the resin, it was purified by HPLC and verified for synthesis by MS, and then freeze-dried.

Specific peptide synthesis process is described by the following with the example of pep1 of SEQ ID NO: 1.

1) Coupling

The amino acid (8 equivalent) protected with NH$_2$-Lys (Boc)-2-chloro-Trityl Resin was melted in coupling agent HBTU(8 equiv.)/HOBt(8equiv.)/NMM(16 equiv.), and upon addition of DMF, the reaction mixture was incubated at room temperature for 2 hours, then washed sequentially with DMF, MeOH, and DMF.

2) Fmoc Deprotection

Following the addition of 20% piperidine in DMF, the reaction mixture was incubated at room temperature for 5 minutes 2 times, then washed sequentially with DMF, MeOH, and DMF.

3) Make the basic framework of peptide by repeating reactions 1 and 2 repeatedly.

4) Cleavage: Add Cleavage Cocktail to the completely synthesized peptide and separate the peptide from the resin.

5) Add pre-chilled diethyl ether into the mixture, and then centrifuge the reaction mixture to precipitate out the peptides.

6) After purification by Prep-HPLC, check the molecular weight by LC/MS and lyophilize to obtain the peptides in a powder form.

Example 2: Cell Penetrating Property of a CPP-FITC Conjugate

1. Synthesis of a Conjugate
(1) Synthesis of a FITC-CPP Conjugate

A conjugate of the peptide with SEQ ID NO: 1 combined with FITC was manufactured as follows, for example, a conjugate of pep1 with SEQ ID NO: 1 and FITC, in other words, FITC-linker-pep1 was manufactured as follows.

The basic framework of peptide, NH$_2$-linker-E(OtBu)-A-R(Pb0-P-A-L-L-T(tBu)-T(tBu)-S(tBu)-R(PbOL-R(Pbf)-F-I-P-K(Boc)-2-chloro-Trityl Resin) which was obtained according to the manufacturing methods described in Example 1, was reacted with FITC. Specifically, FITC (fluorescein-5isothiocyanate) (8 equivalent) and DIPEA (N,N-Diisopropylethylamine) (16 equivalent) were melted in DMF. The DMF solution was added, and reacted at room temperature for 2 hours, then washed sequentially with DMF, MeOH and DMF. As a result, FITC-linker-E(OtBu)-A-R(Pbf)-P-A-L-L-T(tBu)-S(tBu)-R(Pbf)L-R(Pbf)-F-I-P-K (Boc)-2-chloro-Trityl Resin was obtained. The linker herein is 6-aminohexanoic acid, Ahx. TFA/TIS/H$_2$O=95/2.5/2.5 was added to the peptide made on the resin, and the conjugate was separated from the resin. A pre-chilled diethyl ether was added to the obtained mixture, and centrifugation was used to precipitate the peptide conjugates. After purification by Prep-HPLC, purity was confirmed with the analytical HPLC and the molecular weight was determined by LC/MS. The peptide synthesized as described above was verified as FITC-pep1 by confirmation of the molecular weight by LC/MS. Then the conjugates were lyophilized.

(2) Synthesis of a CPP-FITC Conjugate

The basic framework of the peptide, (NH$_2$-E(OtBu)-A-R (Pbf)-P-A-L-L-T(tBu)-S(tBu)-R(Pbf)L-R(Pbf)-F-I-P-K (Dde)-2-chloro-Trityl Resin) was generated according to the manufacturing methods described in the Example 2 1. (1). To selectively introduce FITC to the C-term of the peptide, the N-term of the peptide was protected from Boc. Then, Di-tert-butyl dicarbonate (30 equivalent) and DIPEA (30 equivalent) were melted in DMF. The DMF solution was added to the peptide and incubated at room temperature for 2 hours, and the peptide was washed sequentially with DMF, MeOH, and DMF. As a result, Boc-E(OtBu)-A-R(Pbf)-P-A-L-L-T(tBu)-S(tBu)-R(Pbf)L-R(Pbf)-F-I-P-K(Dde)-2-chloro-Trityl Resin was obtained. Hydrazine in 2% of DMF was used to remove Dde which is the protecting group of the C-terminal residueLys in order to add FITC to the C-terminal of Lys. Then, FITC(8 equivalent) and DIPEA(16 equivalent) were melted in DMF which was added to the peptide reaction mixture, and the mixture was incubated at room temperature for 2 hours, then washed sequentially with DMF, MeOH, DMF. As a result, Boc-E(OtBu)-A-R(Pbf)-P-A-L-L-T(tBu)-S(tBu)-R(Pbf)L-R(Pbf)-F-I-P-K(FITC)-2-chloro-Trityl Resin was obtained. TFA/TIS/H$_2$O=95/2.5/2.5 was added to separate the peptide from resin. Pre-chilled diethyl ether was added to the the mixture, and centrifugation was used to precipitate the peptides. After purification by Prep-HPLC, purity was confirmed with the analytical HPLC and the molecular weight was confirmed with LC/MS. The obtained substances were verified as pep1-FITC by confirmation of the molecular weight by LC/MS. Then the conjugates were lyophilized.

2. Primary Experiment
(1) Cell Culture

The following cells and cell lines were used: CHO (Chinese hamster ovary cell line), line), Huh7 (human hepatocellular carcinoma cell line), HepG2 (human hepatocellular carcinoma cell line), MCF7 (Human breast adenocarcinoma cell line), COS7 (monkey kidney fibroblast cell line), Jurkat (human T lymphocyte cell line), Raji (human B cell line), THP1 (human monocyte cell line), and K562 (human leukemia cell line), bmDCs (bone marrow derived dendritic cells), and primary cells derived from human synovial fluid and synovial tissues.

Huh7, MCF7, Jukat, Raji, THP1, K562 were cultured in RPMI 1640 medium, CHO cells in medium, and HepG2 cells in MEM media. Growth media for all cells were supplemented with 10% fetal bovine serum (Invitrogen, USA), 100 ug/ml penicillin, 100 units/ml streptomycin, and cells were cultured at 37° C., 5% $CO_2$.

bmDCs were differentiated into dendritic cells in RPMI 1640 medium containing cells obtained from mouse bone marrow, GM-CS(20 ng/ml) and IL4(20 ng/ml). $1 \times 10^6$ of the cells were seeded onto a 24-well plate, the medium was replaced once every 2 days, and the mature dendritic cells obtained on day 7 were used for experiment.

PBMC (peripheral blood mononuclear cell) and lymphocytes were prepared from the human blood samples (50 ml) collected from healthy subjects using Biocoll Separating Solution (Biochrom AG, Berlin, Germany).

HeLa were culture in Minimum Essential medium (MEM) containing 10% fetal bovine serum (Invitrogen, USA), Earle's salts, non-essential amino acids, sodium pyruvate and 100 μg/ml penicillin and 10 units/ml streptomycin and cultured at 37° C., 5% $CO_2$ incubator.

All of above mentioned cell lines were purchased from ATCC (American Type Cell Culture).

(2) Uptake Analysis of pep1-FITC In Vitro

Flow cytometry and Confocal microscopy analysis were performed to compare the degree of cellular uptake among differentcell lines treated with pep1 (SEQ ID NO: 1) and the previously known PTD, TAT (YGRKKRRQRRR) (SEQ ID NO: 10) of HIV.

Flow Cytometry

Cells were cultured at 37° C., 5% $CO_2$ incubator and grown to 90~100% confluence. The confluence. The medium was removed and washed with PBS, 1 mL of OPTI-MEM was added to each well and cultured at 37° C., 5% $CO_2$ incubator for an hour for cell starvation. After washing with OPTI-MEM once, cells were treated with peptide in OPTI-MEM (concentration of 100 μl) and FITC (concentration of 10 μM), cultured at 37° C., 5% $CO_2$ incubator. After removing the medium, cells were washed with 1×PBS three times and harvested using Trysin/EDTA. The cellular uptake of FITC and the rest of FITC-conjugated peptide was compared and analyzed with untreated cell cells as a control.

As a result, pep1 was confirmed that it has better cell penetrating ability than TAT which is known as cell penetrating peptide. Especially, the cell penetrating ability was best when FITC was conjugated with lysine residue in C terminal.

Confocal Microscopy Analysis

Cells were seeded onto 2 chambered-well slide (NUNC, Lab-Tek), grown to reach 50% confluence in a medium containing 10% fetal bovine serum (Invitrogen, USA), 100 ug/ml penicillin, 100 units/ml streptomycin, and cultured at 37° C., 5% $CO_2$ incubator for 12 hours.

After removing the medium, cells were washed with PBS and starvedin 1 ml of OPTI-MEM for an hour. Fifty μl of peptide combined with FITC (5 μM) was added in each camber, and cultured at 37° C., 5% $CO_2$ incubator for 2 hours. After removing the medium, cells were washed with PBS three times and were fixed for 20 mins in 0.5 mL 4% Paraformalehyde at room temperature. 4% PFA was quickly washed with PBS twice. The nucleus of cell was stained with 500 nM of TO-PRO®-3 Iodide 642/661 nm (Invitrogen) for 10 min at RT. Then, cells were washed three times with 1×PBS, plastic camber was removed, No. 1.5 thickness cover slip was placed on a slide after dropping VECTASHIELDFX mounting medium (Vector laboratories) without any bubbles. A sample was made by applying transparent nail polisher to the edge of cover slip. The sample was stored at 4° C. in a dark before observing with fluorescence microscope, and analyzed by confocal laser scanning system. FV1000 larger scanning confocal microscope (Olympus) was used in the analysis.

(i) ELISA (Enzyme-Linked Immunosorbent Assay)

Cells were treated with pep1, washed 2× with 1×PBS, and re-suspended with the lysis lysis buffer containing 50 mm Tris pH7.5, 10 mM EDTA pH8.0, 1 mM PMSF, 2 mM NaF, 2 mM $Na_3VO_4$, 0.1% NP 40, 100 g/μl Aprotinin. The suspended cells were then sonicated twice for 15 seconds using Sonicator Ultrasonic processor, Misonix, N.Y., USA) and, supernatant (cell lysate) was obtained by centrifugation at 4° C., 13,000 rmp for 10 minutes. Protein concentration was determined using Bradford Protein Assay (Bio-Rad, USA), and Fluorescence ELISA was performed.

3. Secondary Experiment (1) Cell Penetrating Property in HeLa Cell Line

Flow cytometry and Confocal microscope analysis were performed to compare the degree of cellular uptake of previously known protein transduction domain, TAT (YGRKKRQRRR) of HIV; wherein the cells were treated with a conjugate of pep1 and FITC prepared from the Example 2.1.

The cell line was divided in a 6-well plate and cultured in a medium containing 10% fetal bovine serum (Invitrogen, USA), 100 μg/ml penicillin, 100 units/ml streptomycin at 37° C., 5% $CO_2$ incubator for 12 hours. After washing the cell line with PBS, starvation was induced in a Minimum Essential Medium for an hour. 20 uM of each carrier peptide was treated and cultured at 37° C. for an hour. After repeating the step of washing the cells with PBS for three times, Trypsin-EDTA was treated form 10 mins at 37° C. to separate the carrier peptide on the outside of the cell. cells were collected with refrigerated PBS and centrifugation was performed to repeat the step of washing the cells for three times. After then, the cells were suspended in 0.5 ml of PBS containing 4% Paraformaldehyde and fluorescence of the cells was analyzed using FACS Calibur (Becton Dickinson). The cellular uptake aspect of control and various peptides combined with FITC was compared and analyzed by MFI (Mean Fluorescence Intensity).

Figure 7:
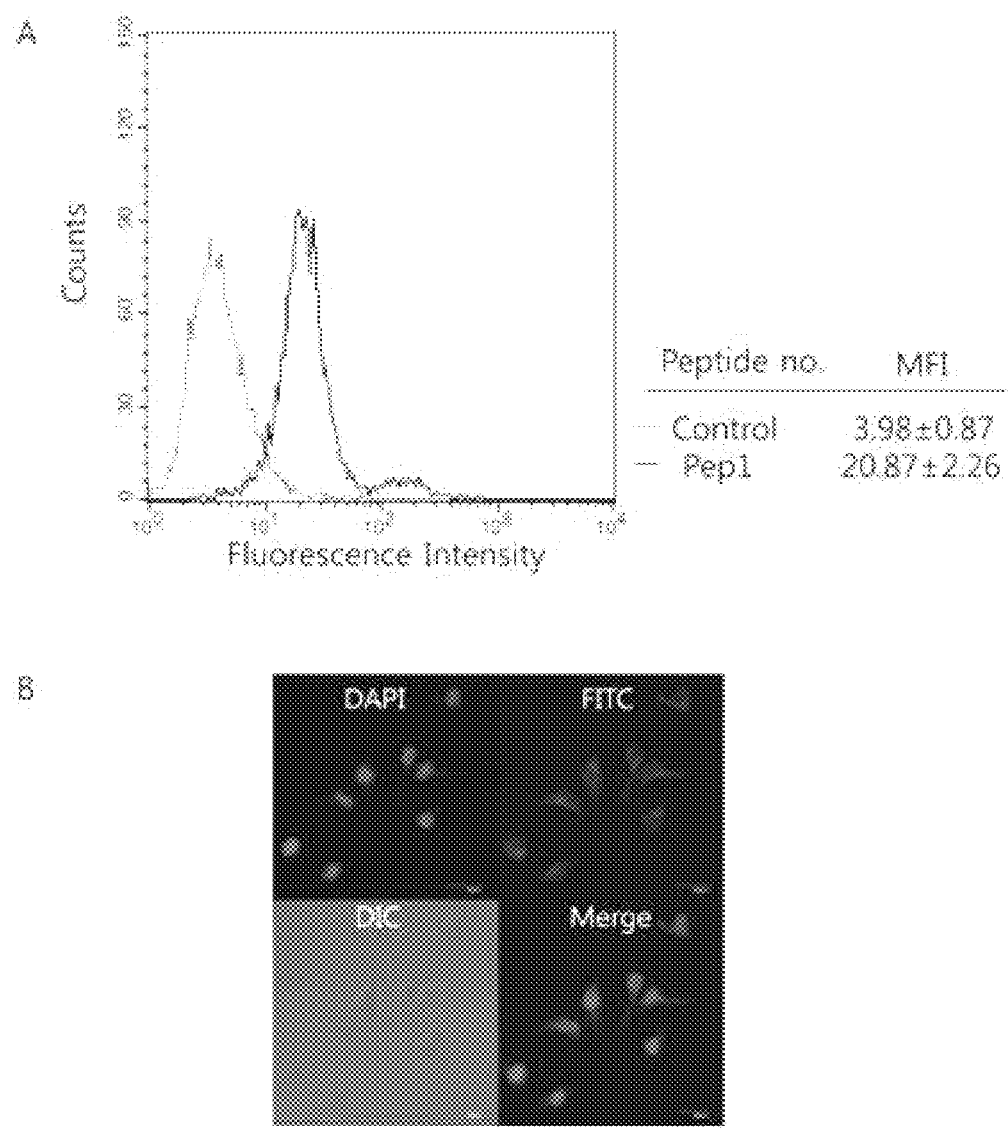
FIG. 7 represents the cellular uptake of peptide with SEQ ID NO: 1 labeled with FITC in HeLa cells. Cells were treated with the peptide for 1 hour and analyzed by FACS (Control groups were those only treated with FITC).

The cultured cell line was divided in chamber well and cultured in a medium containing 10% fetal bovine serum (Invitrogen, USA), 100 μg/ml penicillin and 100 units/ml streptomycin at 37° C., 5% $CO_2$ incubator for 12 hours. After washing the cells with PBS, starvation was induced in Minimum Essential Medium for an hour. 10 μM of each peptide was treated and cultured at 37° C. for an hour. After repeating the step of washing the cells with PBS for 3 times, cells were fixed in room temperature for 15 mins by 2% (v/v) Paraformaldehyde. The nucleus was dyed with DAPI (4',6-diamidino-2-phenylindole) in room temperature, and cells were compared and analyzed by Confocal microscope analysis. The result is same as shown in FIG. 7.

Figure 8:
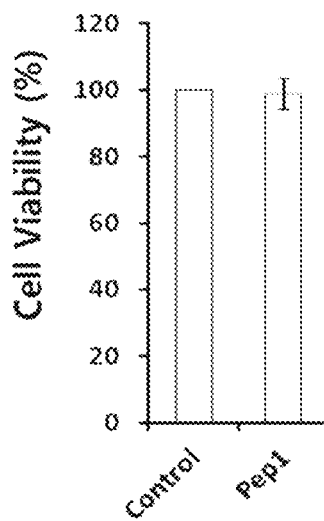
FIG. 8 represents the result of toxicity and cell viability assay of the peptide with SEQ ID NO: 1 combined with FITC and each of which was used to treat HeLa cells.

On the other hand, to analyze cell viability and toxicity, above cultured cell line was divided in a 96-well plate and cultured in a medium containing 10% fetal bovine serum (Invitrogen, USA), 100 μg/ml penicillin and 100 units/ml streptomycin at 37° C., 5% $CO_2$ incubator for 12 hours. After washing the cells with PBS, starvation was induced in Minimum Essential Medium for an hour. 20 μM of each carrier peptide was treated and cultured for 24 hours at 37° C. The cell viability and toxicity were analyzed by MTT assay method. The result is same as shown in FIG. 8.

(2) Flow Cytometry Analysis of Cell Penetrating Property in Huh7 Cell Line

Figure 9:
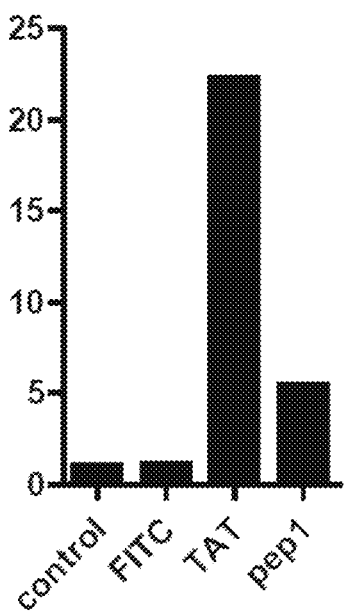
FIG. 9 and FIG. 10 represent the result of flow cytometry on cell penetrating property of pep1 in Huh7 cell line.
Figure 10:
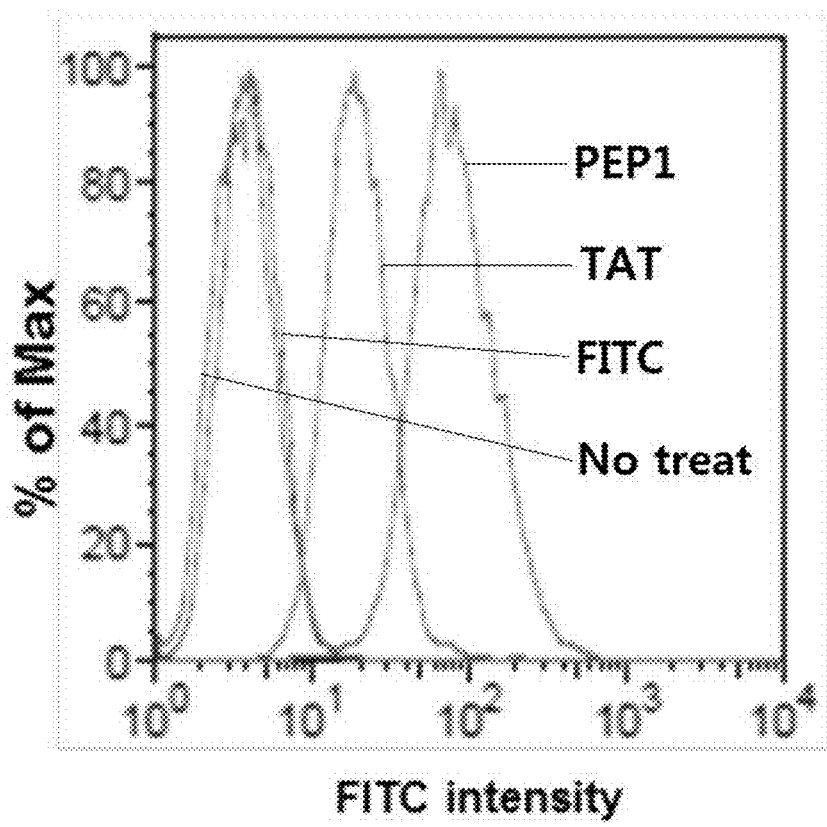

To investigate cell penetrating property of PEP1, flow cytometry was performed in Huh7 cell line treated with PEP1. The analytical methods used were same as described in above (1) HeLa cell line analysis. The result showed that cell penetrating property of PEP 1 was lower than that of TAT but higher than that of control. (FIG. 9 and FIG. 10)

(3) Cell Penetrating Property of pep1 in Human T Lymphocyte

Figure 11:
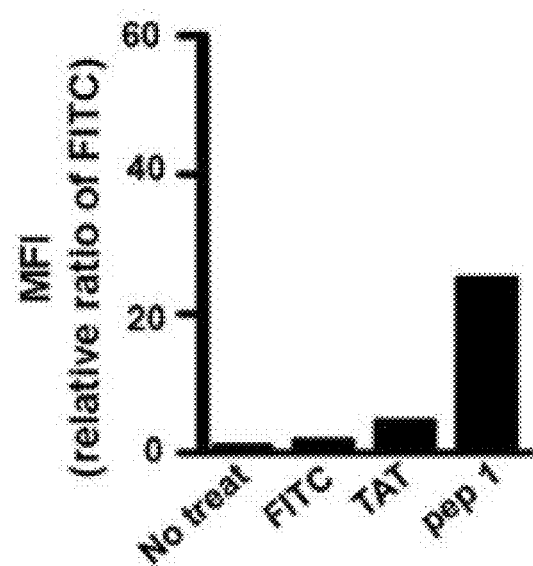
FIG. 11 and FIG. 12 represent the result of flow cytometry on cell penetrating property of pep1 in human T lymphocyte cell line.
Figure 12:
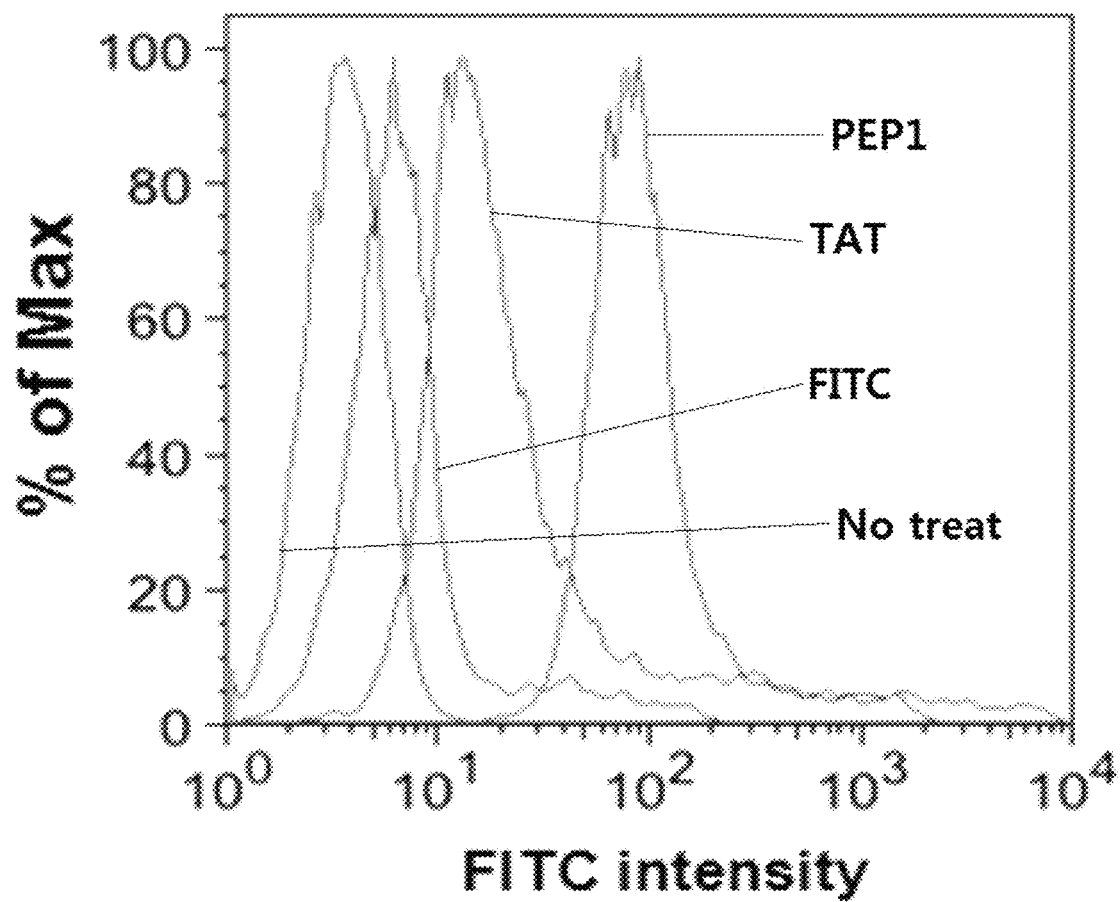
Figure 13:
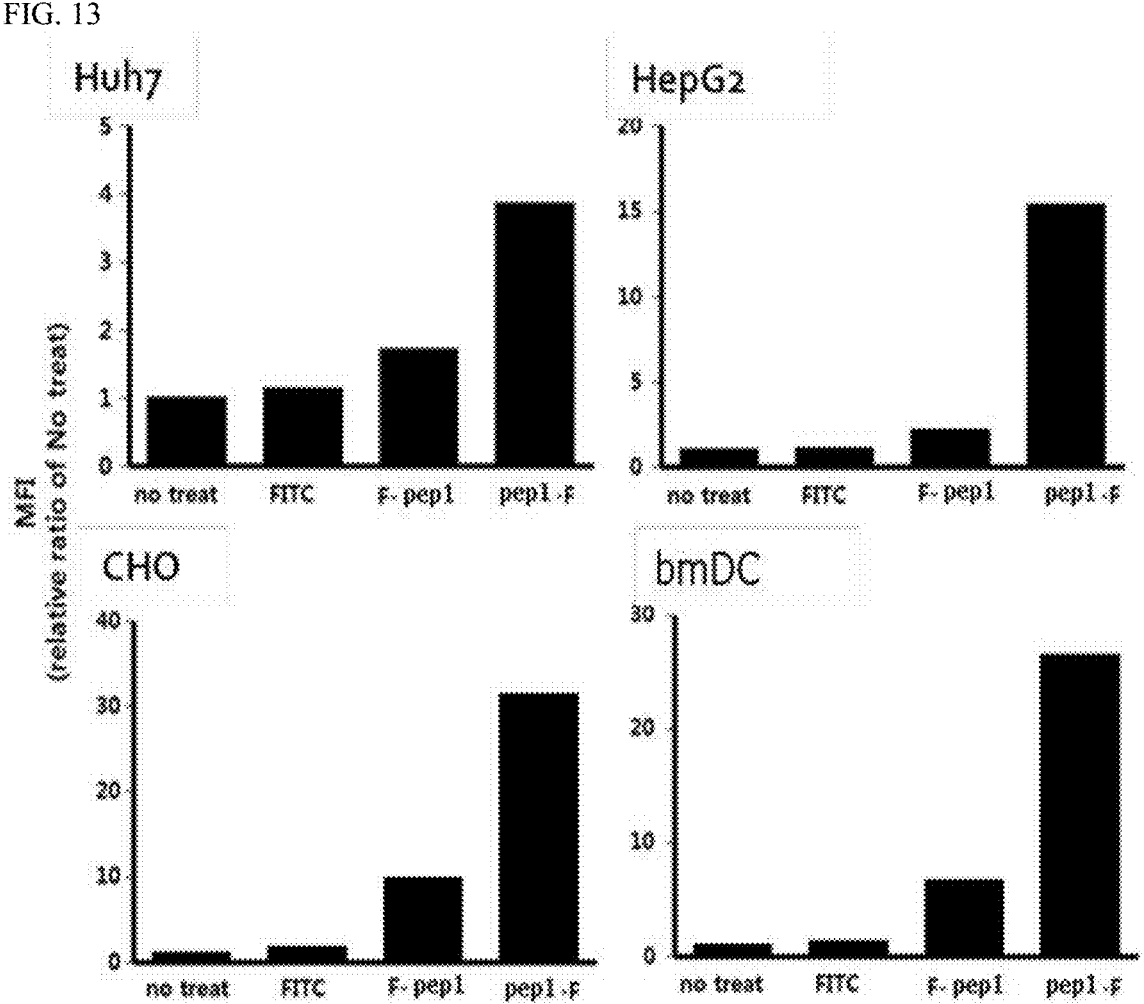
FIG. 13 and FIG. 14 represent the result of flow cytometry and confocal microscopic analysis on cell penetrating property of pep1 based on the position of FITC conjugation.

To investigate cell penetrating property of PEP1, the peptide was treated in human T lymphocyte, and FACS (Fluorescence-activated sell sorting) was performed as flow cytometry analysis. The analytical method used was same as described in above (1) HeLa cell line analysis. The result showed that pep1 has cell penetrating property 25 times higher than that of control FITC and 6 times higher than that of HIV derived TAT. (FIG. 11 and FIG. 12)

Figure 14:
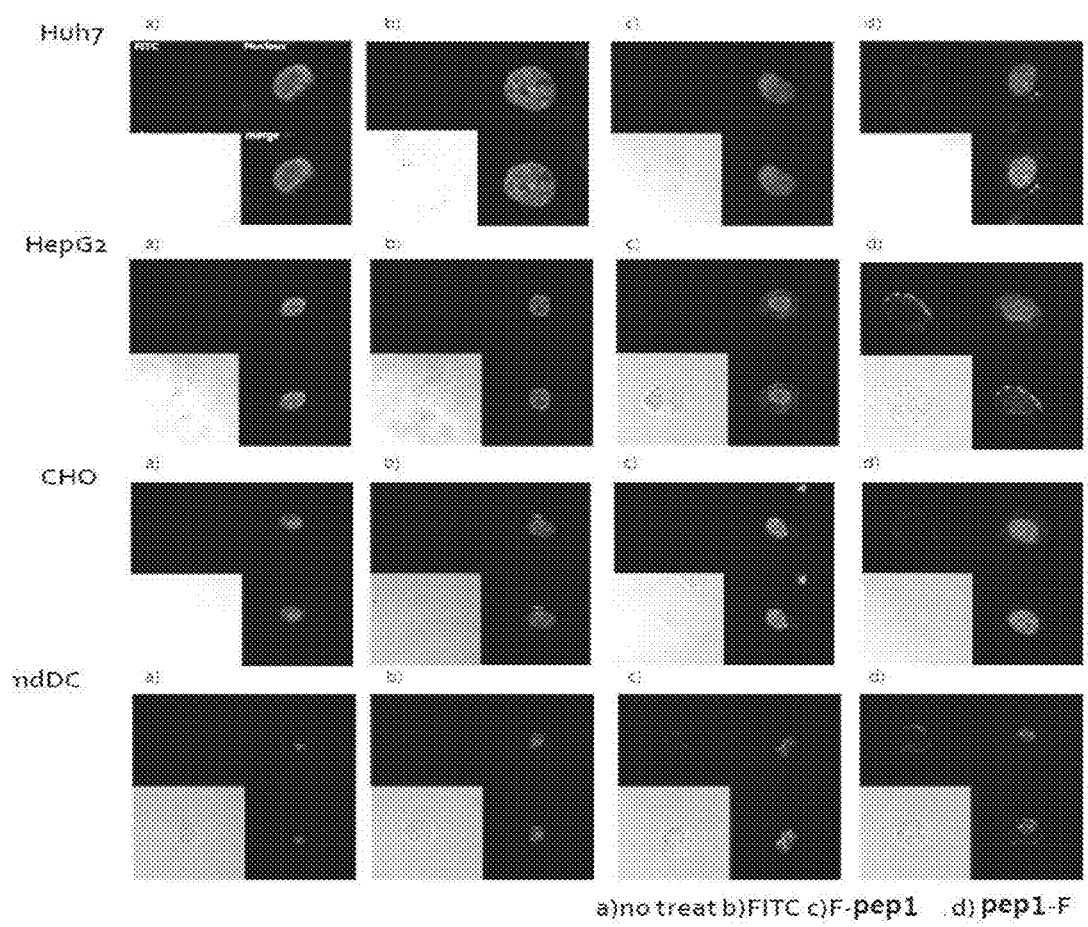

(4) Flow Cytometry and Confocal Microscope Analysis of Cell Penetrating Property of PEP1 Depending on Location of FITC Synthesis To investigate cell penetrating property of PEP1 in various cell lines, flow cytometry and Confocal microscope analysis were performed using a conjugate of PEP1 combined with FITC at N, and C-terminal of the peptide. The analytical method used was same as described in above (1) HeLa cell line analysis. The cell lines used were Huh7, HepG2, CHO, bmDC. The result showed that PEP1 combined with FITC at C-terminal had cell penetrating property approx, 3 to 10 times higher than the other. Also, when observed with fluorescence microscope, PEP1 combined with FITC at C-terminal had higher cell penetrating property to penetrate into the cytoplasm than PEP1 combined with FITC at N-terminal. (FIG. 14)

Figure 15:
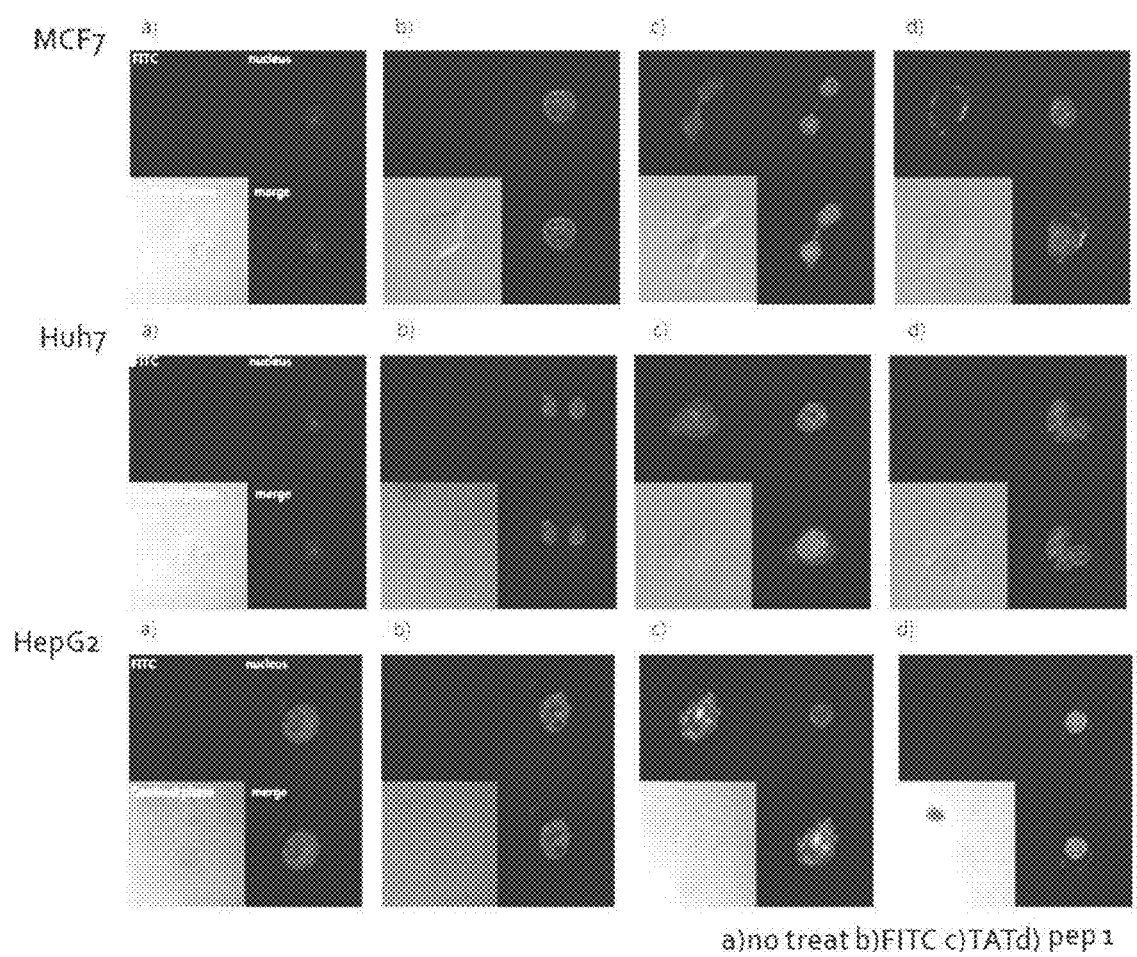
FIG. 15 and FIG. 16 represent the result of confocal microscopic analysis on TAT peptide and PEP 1 in MCF7, Huh7 and HepG2 cell lines to show the difference in level of intracellular fluorescence signals between TAT peptide and pep1.
Figure 16:
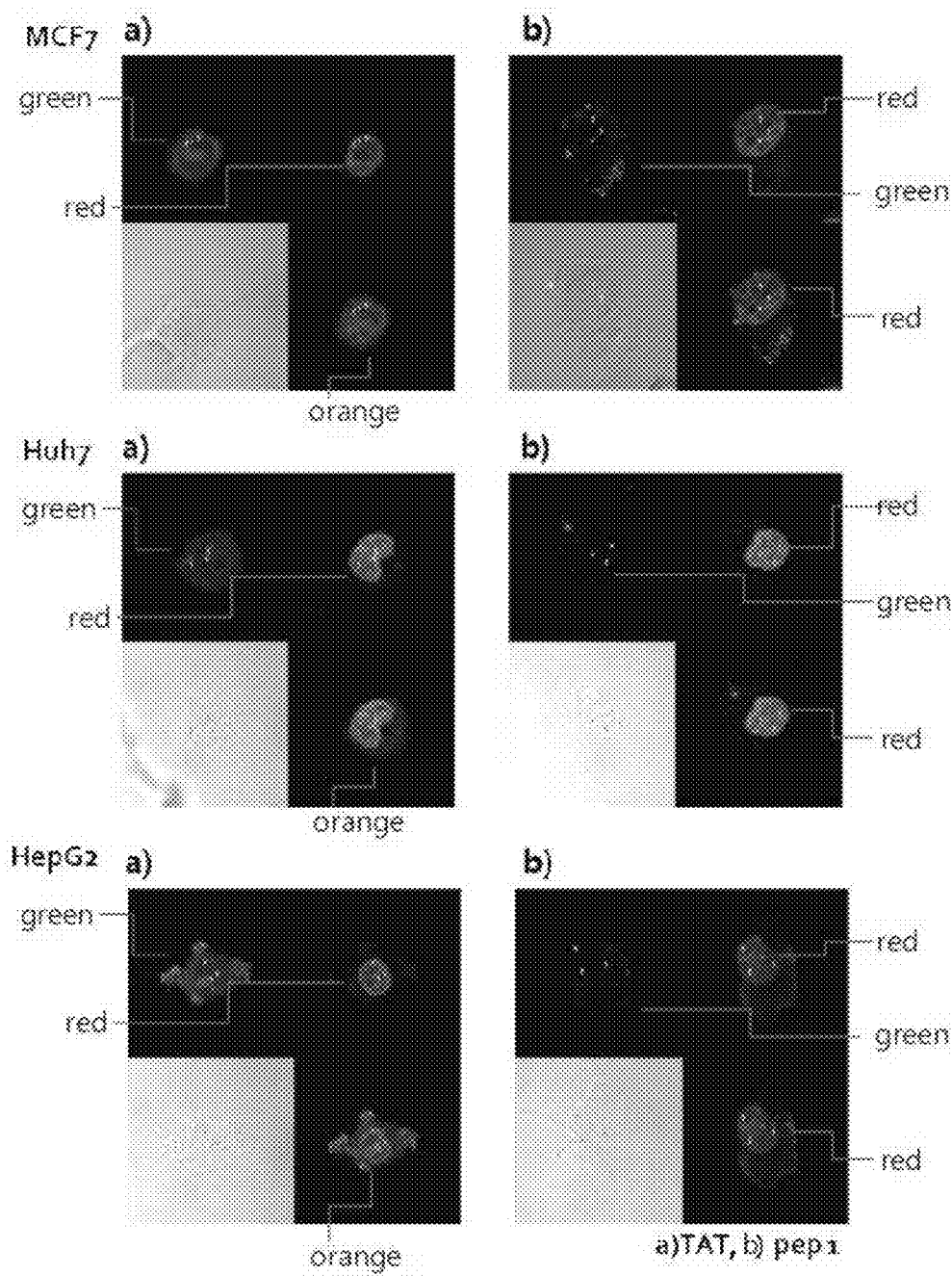

(5) Confocal Microscope Analysis of Cell Penetrating Property of PEP1 and TAT in Various Cell Lines Confocal microscope analysis was performed to show the difference between TAT TAT peptide and PEP1 in terms of absorption inside the cell in each cell line (MCF7, Huh7, HepG2). FIG. 15 and FIG. 16 are diagrams representing analytical results. Green (488 nm) represents FITC; red parts dyed with TOPRO-3 represent the nucleus of a cell. The nucleus was designated as red to show co-localization of nucleus and the peptide. In the diagram, when localization was shown, it was represented as orange combined with green and red. The result showed that the part of nucleus, treated with TAT and represented as orange, was where co-localization of the peptide and the nucleus of cell took place. In contrast to this, there was no part of the cell represented as orange in the nucleus treated with PEP1.

Figure 17:
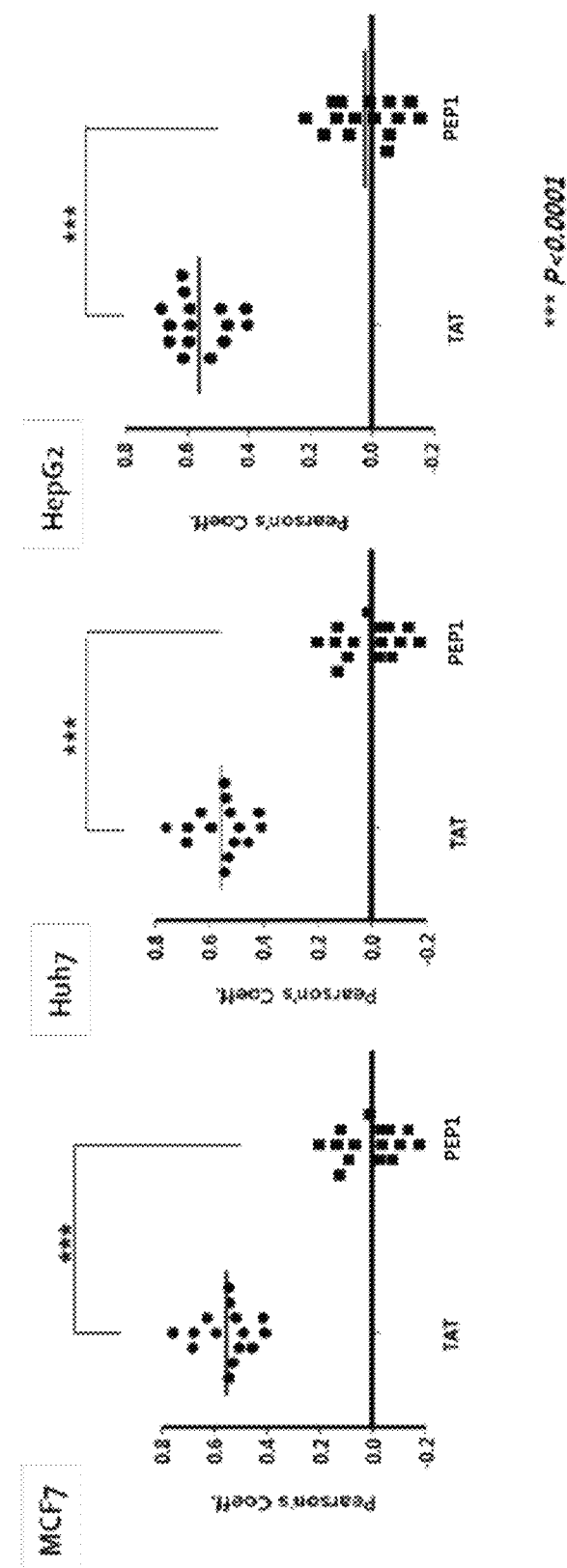
FIG. 17 is a graph which represents a mean dispersion of Pearson's coefficient of intracellular fluorescence signals of TAT peptide and PEP1 in MCF7, Huh7 and HepG2 cell lines.
Figure 18:
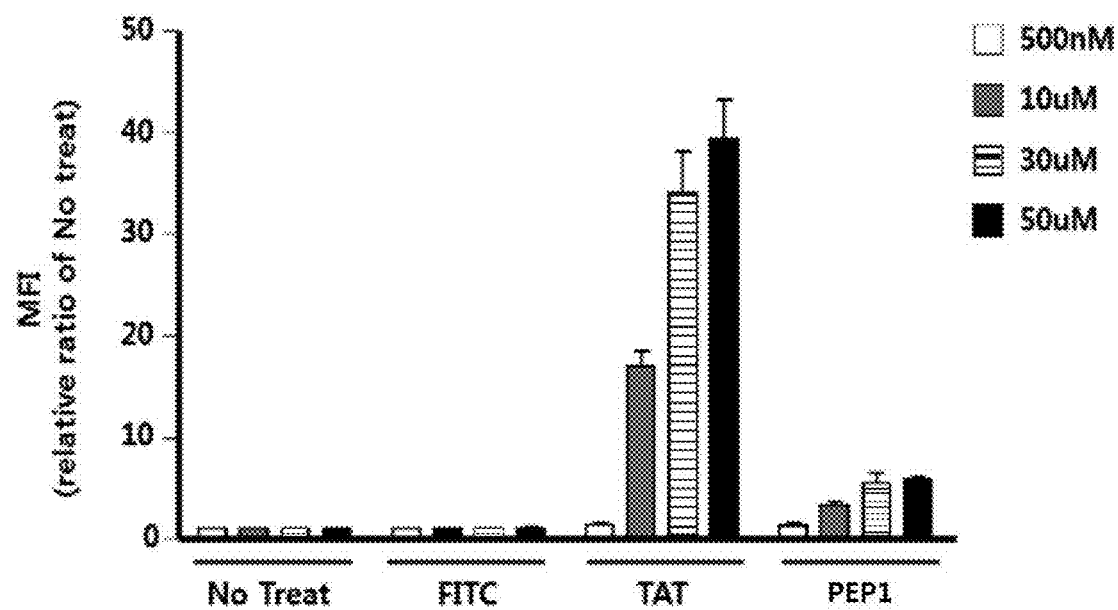
FIG. 18 to FIG. 23 represent the analytical result based on PEP1 concentration in Huh7, Huh7, bmDC (mouse bone marrow-derived dendritic cells), CHO, COS7 cell line.
Figure 19:
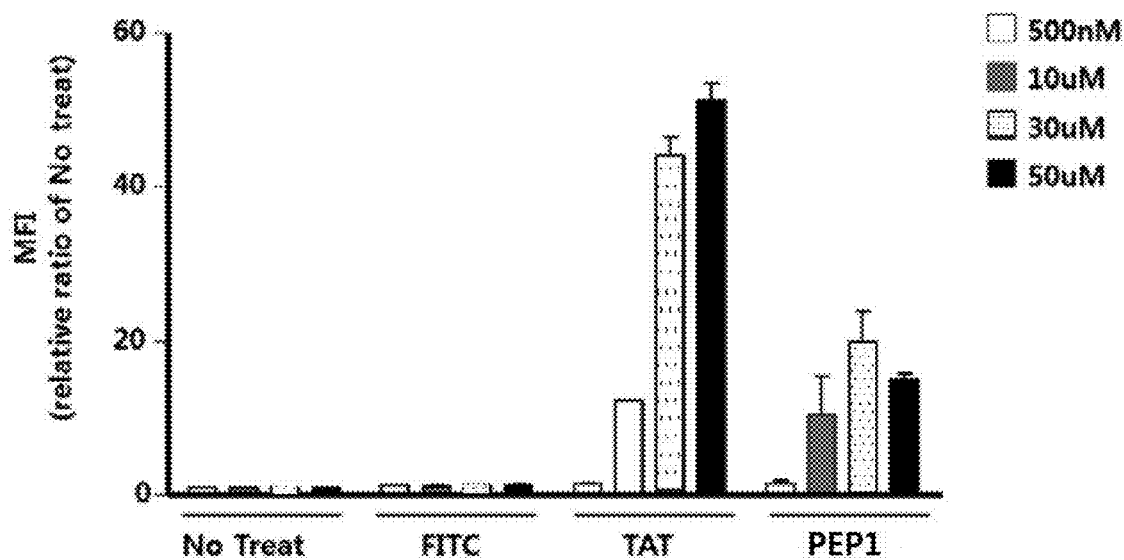
Figure 20:
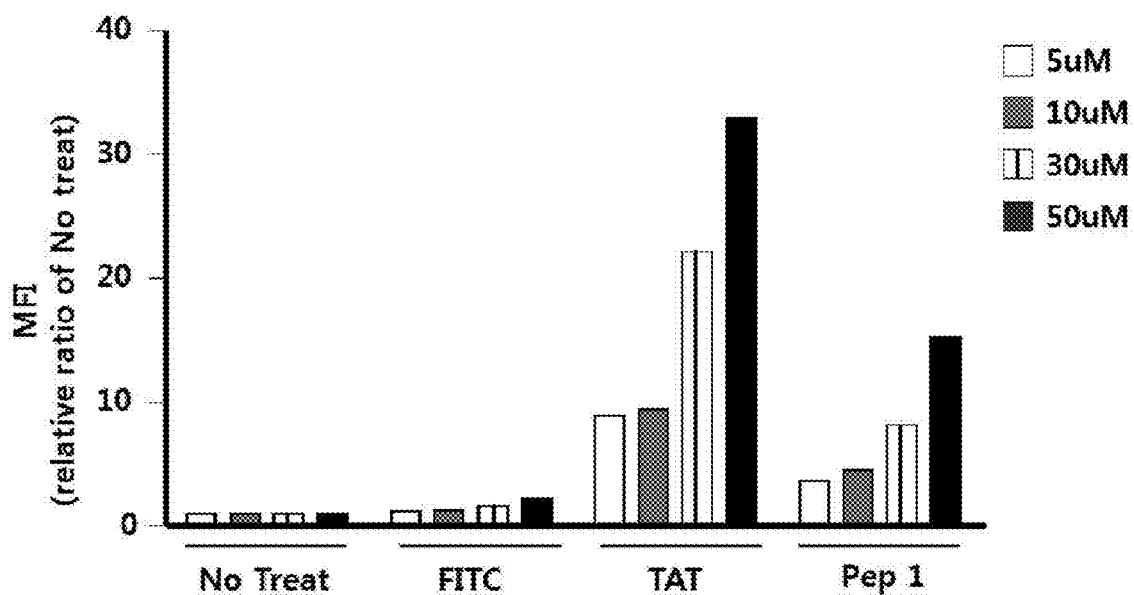
Figure 21:
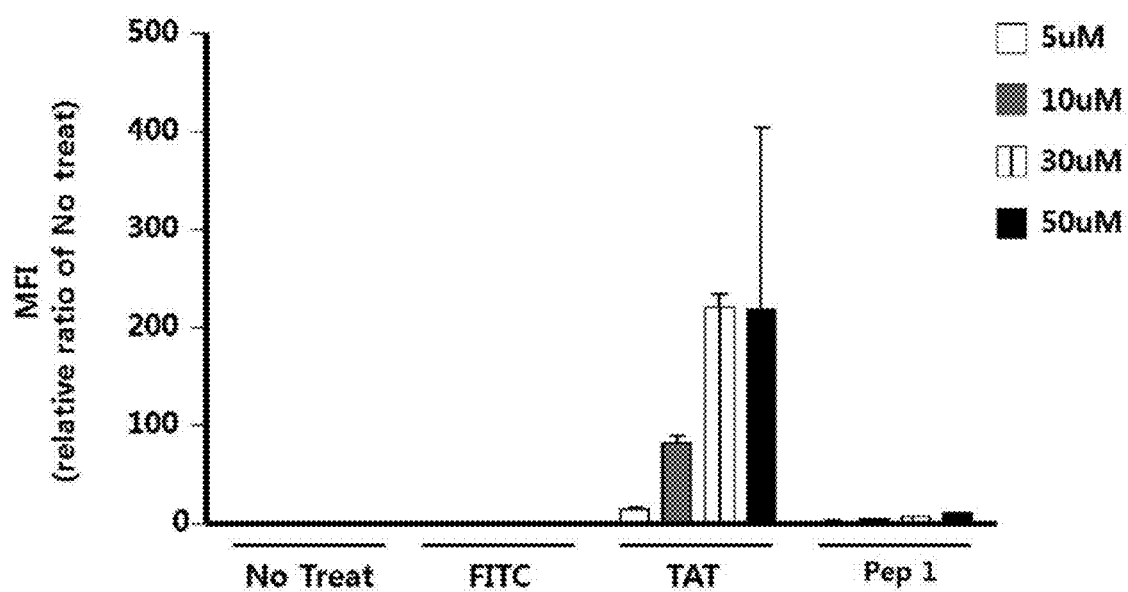
Figure 22:
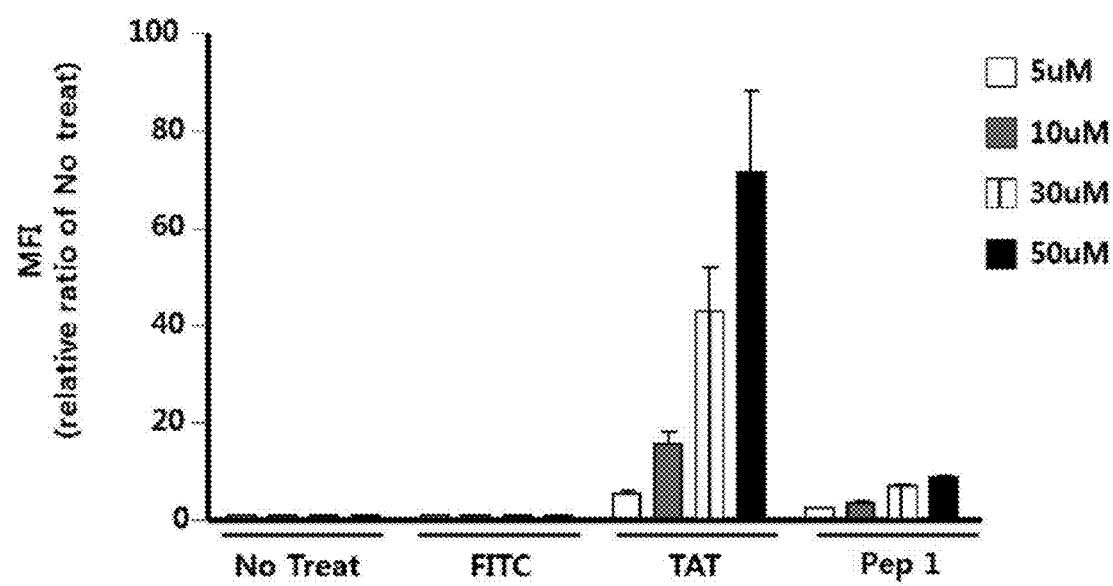
Figure 23:
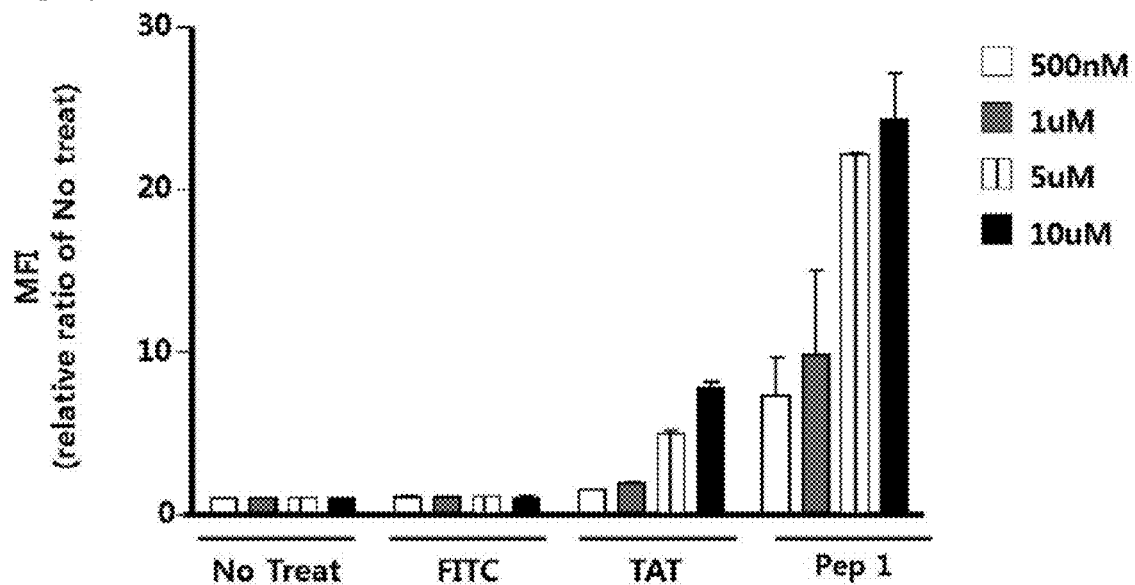

These results mean that PEP1 and TAT are absorbed into the cell at different locations. FIG. 17 is a digitized graph of PEP1 and TAT absorption.

All of the confocal microscope analytical diagrams were produced by FV1000 lager scanning Confocal microscope (Olympus). Pearson's Coeff. meaning co-localization is presented in the diagram. In each cell line MCF7, Huh7, HepG2, region of interest (ROI) was designated to show mean dispersion of Pearson's Coeff. In all of the cell lines, P-value was lower than 0.0001. Through this, it was verified that TAT was localized in the nucleus whereas PEP1 stayed in the cytoplasm without being localized into the nucleus. Like this, the characteristics of PEP1 where it was localized within the cytoplasm, was the most important thing which differentiates PEP 1 from existing cell penetrating peptides including TAT.

Figure 24:
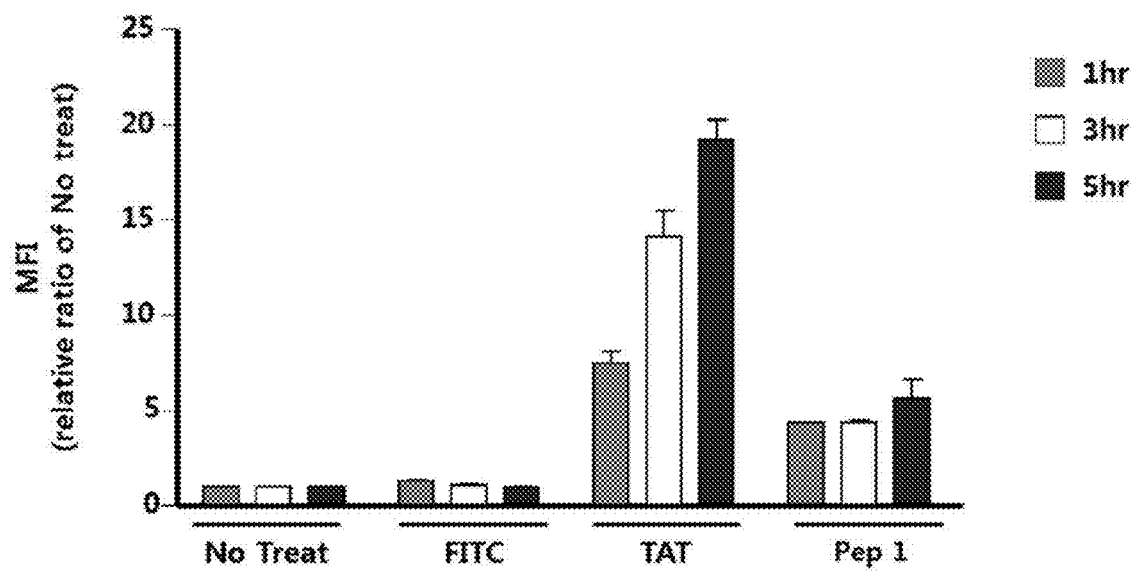
FIG. 24 to FIG. 26 represent the result of pep1 depending on time.
Figure 25:
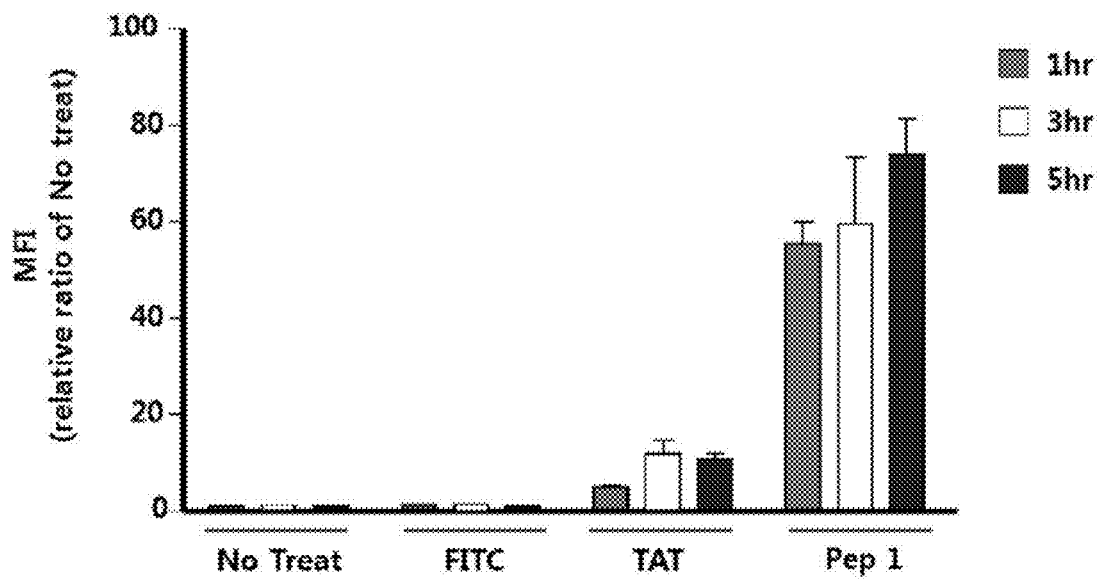
Figure 26:
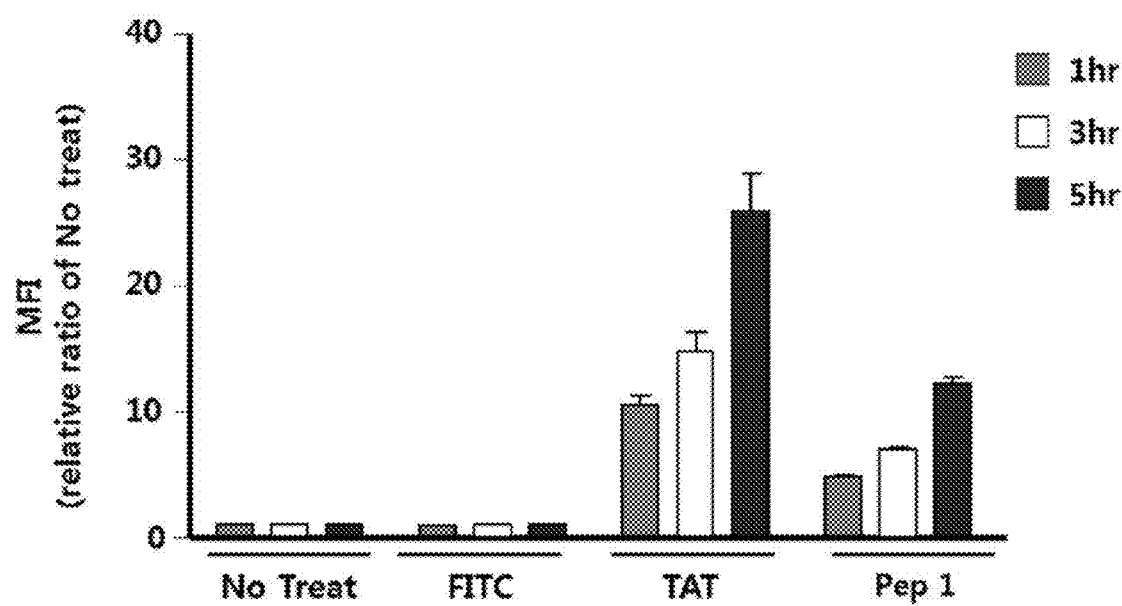
Figure 27:
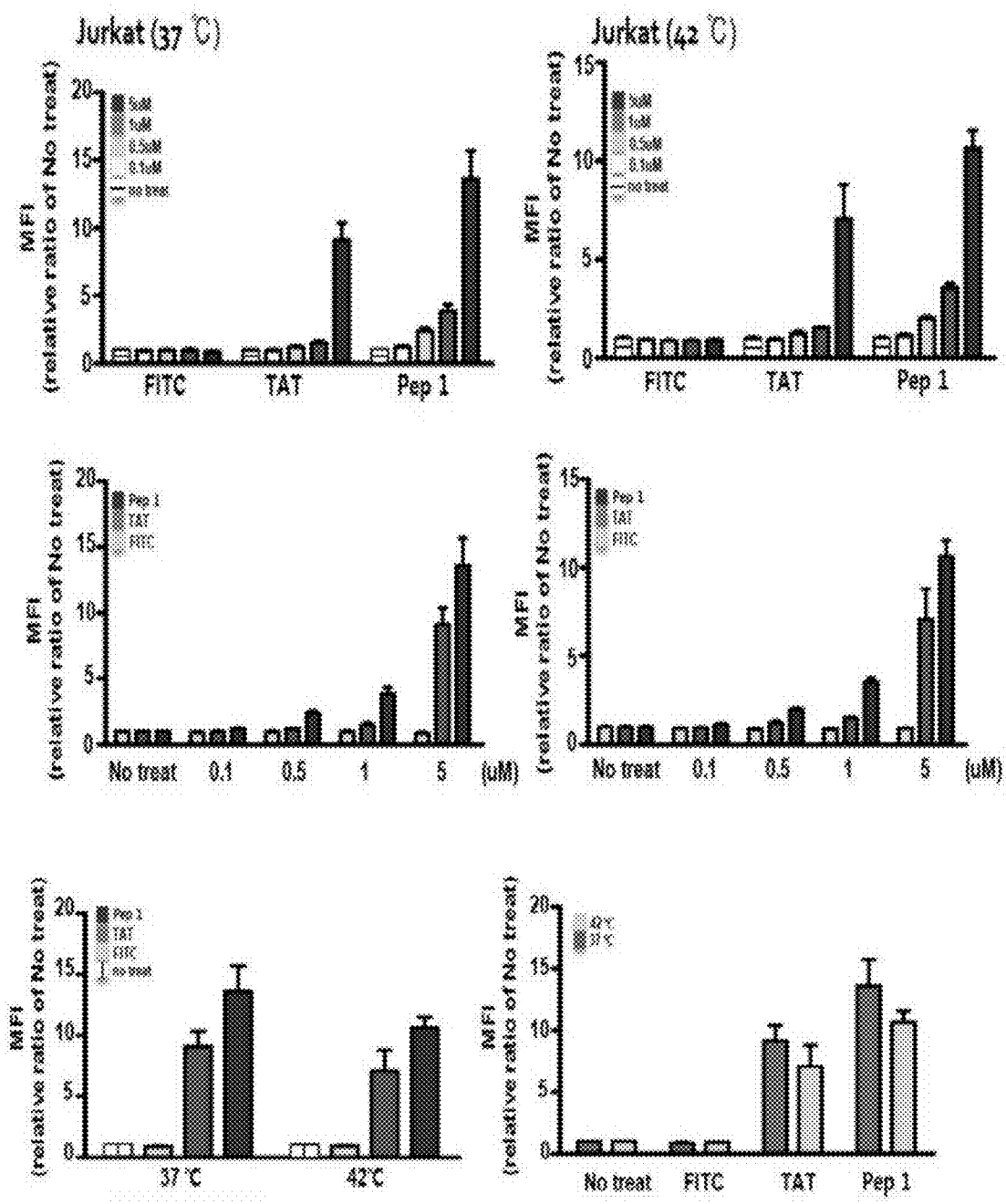
FIG. 27 to FIG. 31 represent the result of cell penetrating property of PEP 1 analyzed by flow cytometry and confocal microscope; wherein different concentrations of pep1, temperature, and incubation time were used to treat Jurkat (Human T cell line), THP1 (Human monocyte cell line), Rail (B cell line), K562 (Human leukemia cell line).
Figure 28:
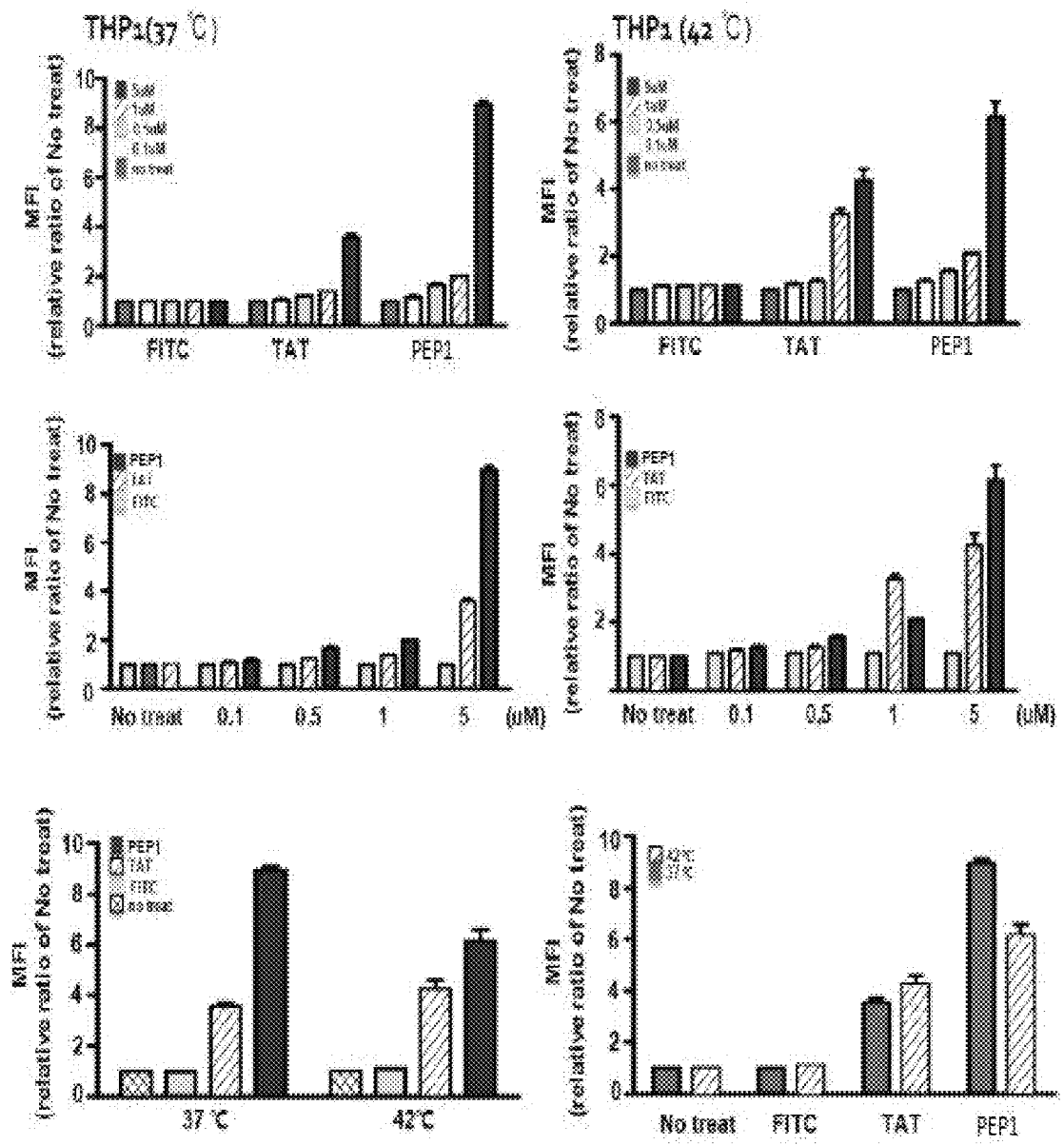
Figure 29:
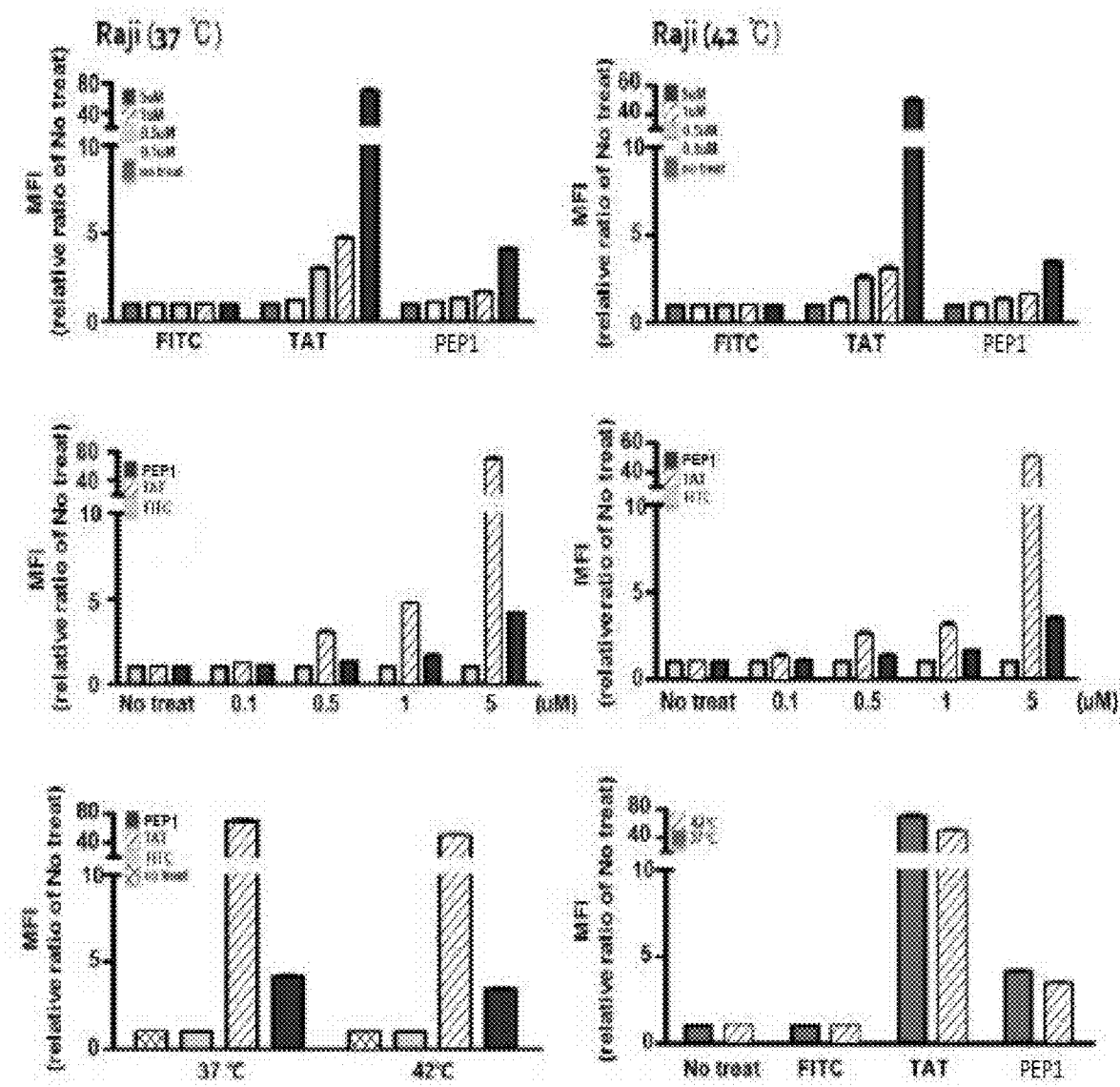
Figure 30:
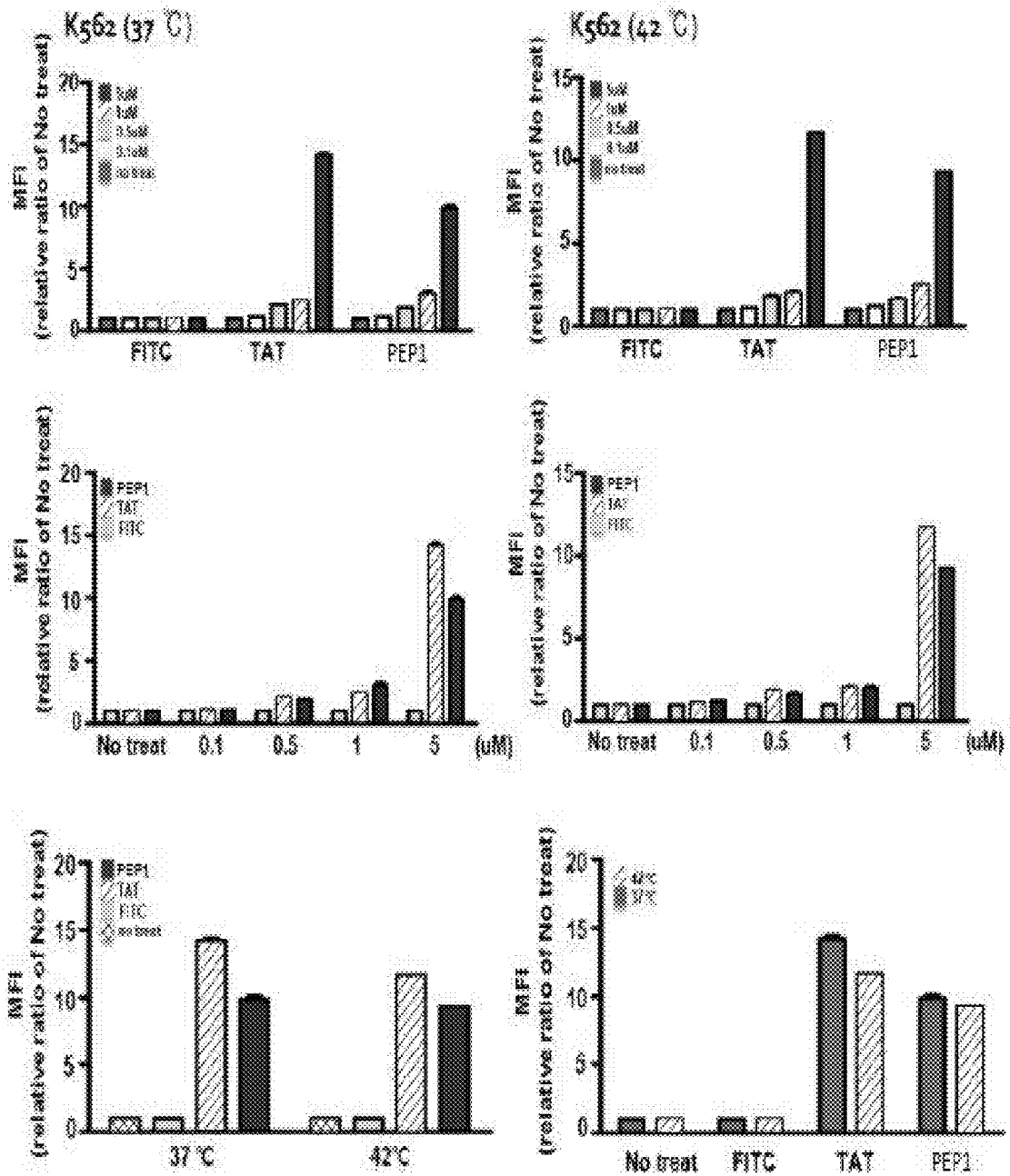
Figure 31:
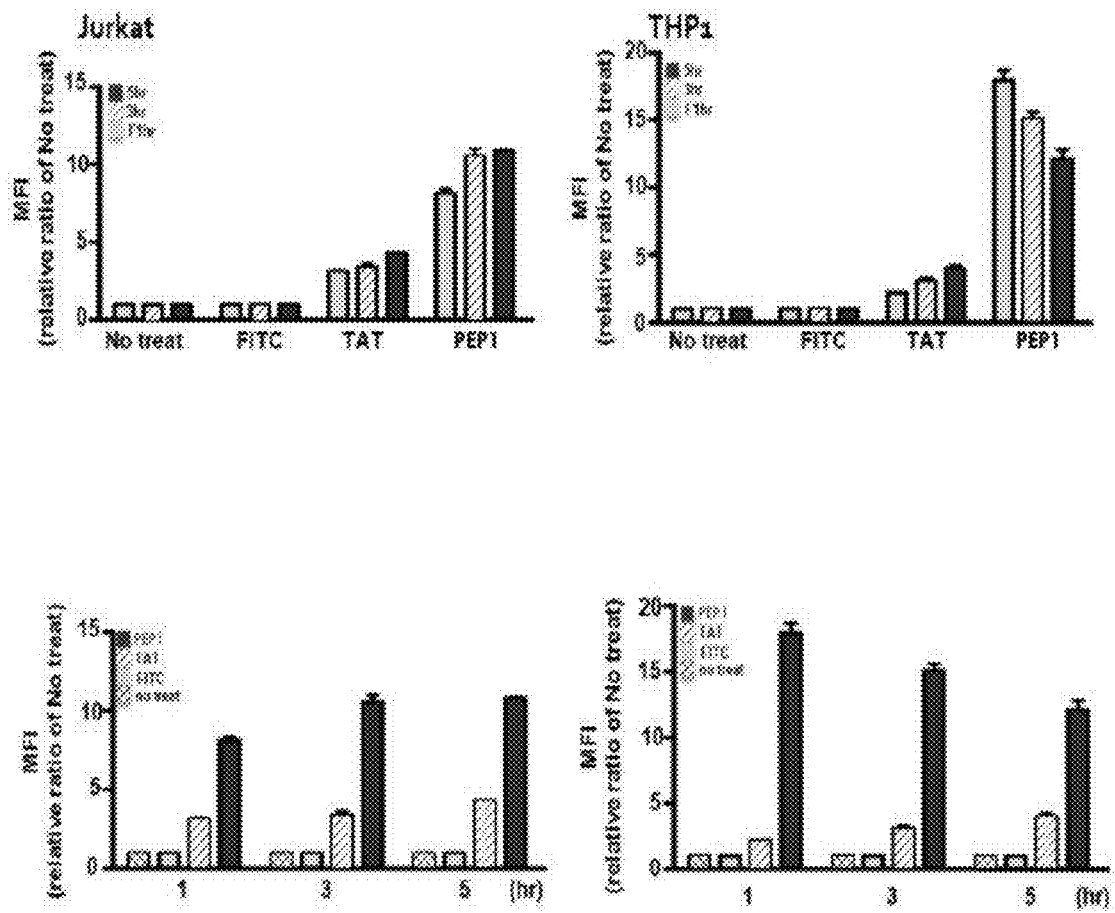

Example 3: Cell Penetrating Property of PEP1 Depending on Different Environmental Conditions (1) Flow Cytometry of Cell Penetrating Property of PEP 1 Depending on Concentration and Time in Various Cell Lines Cell penetrating property of PEP1 was investigated by treating PEP1 with various cell various cell lines depending on concentrations and time. Specific analytical methods followed the methods described in Example 2. The result showed that cell penetrating property of PEP 1 had a tendency to increase in all of the cell lines such as Huh7, bmDC (dendritic cell lines derived from mouse golgi), CHO, COS7 depending on concentrations, like TAT. In the case of HepG2 cell line, cell penetrating property of TAT was increased whereas that of PEP1 was decreased at a concentration of 50 µM. Unlike other cell lines, in MCF cell line, cell penetrating property of PEP 1 increased 4 times higher than that of TAT and they also increased depending on concentrations (FIG. 18 to FIG. 23). When observing cell penetrating property of the peptide depending on time, the cell penetrating property was increased in Huh7, MCF7 and HeLA cell lines. Especially, in MCH7 cell line when 5 µM of the peptide was treated, cell penetrating property was increased 10 times higher in all time (FIG. 24 to FIG. 26)

(2) Flow Cytometry and Confocal Microscope Analysis of Cell Penetrating Property of PEP1 Depending on Concentration, Temperature and Time in an Enriched Cell Line Jurkat (Human T cell line), THP1 (Human mononuclear cell line), Raji (Human B cell line), K562 cell line (Human Leukemia cell line) were used as enriched cell line to treat the peptide depending on concentrations, temperature and time and to analyze the cell penetrating property of the peptide. The result showed that in Jurkat and THP 1 cell line, cell penetrating property of PEP 1 was 1.5 to 2 times higher than TAT, whereas in Raji cell line and K562 cell line, TAT showed higher cell penetrating property than PEP1. Depending on concentrations of the peptide, cell penetrating property showed a tendency to increase in all cell lines. Depending on time, the cell penetrating property was continuously increased more than 3 times, but the cell penetrating property of the peptide was decreased over time in THP1 cell line. There was no difference in cell penetrating property of PEP1 in all cell lines depending on temperature. These results verified that PEP1 had higher cell penetrating property in Jurkat and THP1 cell line.

Figure 32:
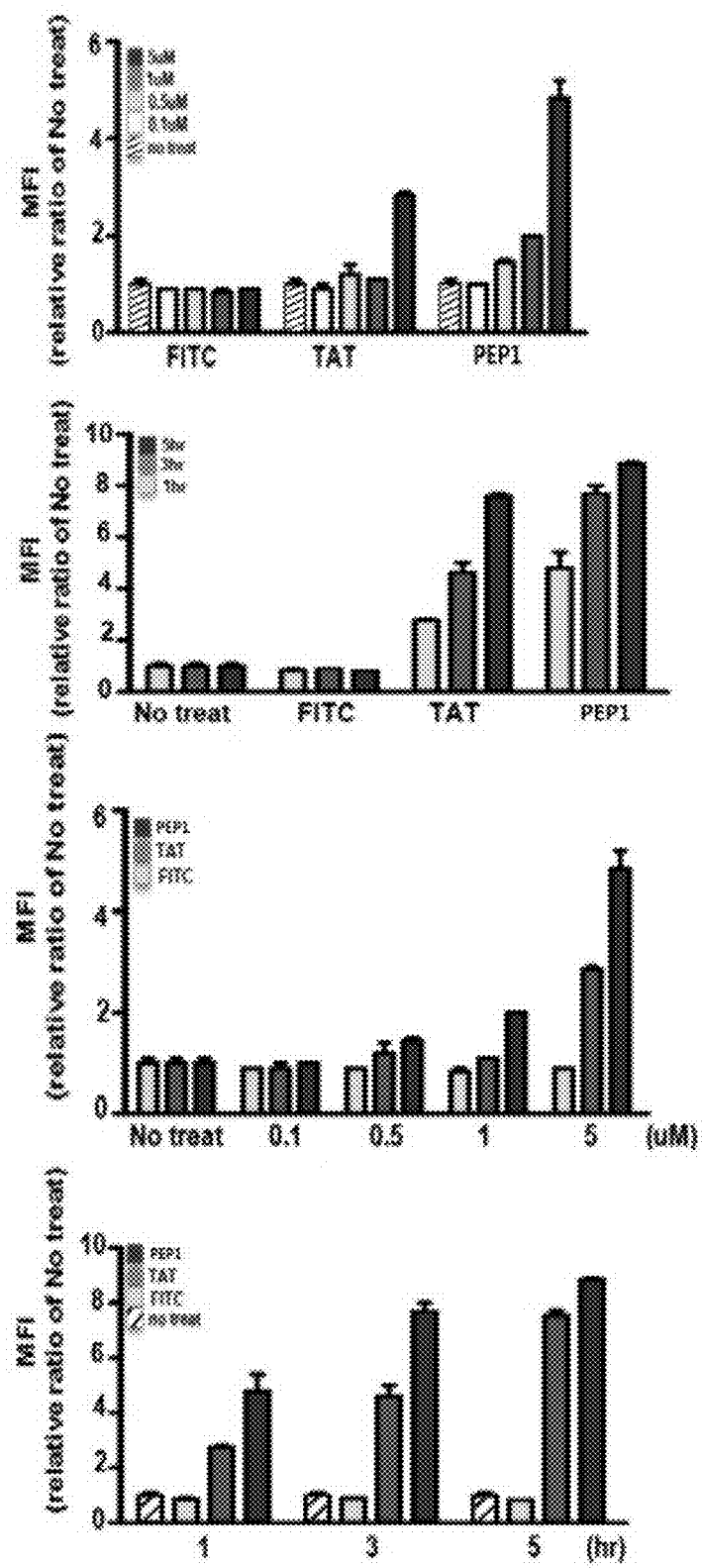
FIG. 32 to FIG. 34 represent the result of flow cytometry analysis of pep1 with different concentration, temperature and treatment time in human PBMC.
Figure 33:
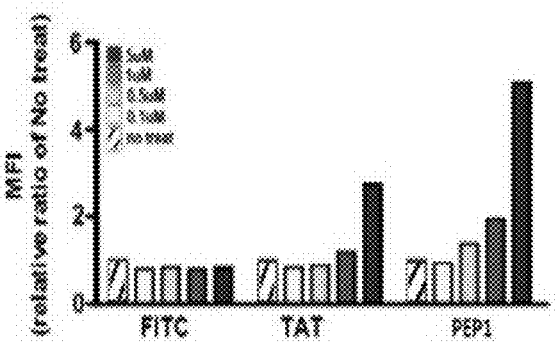
Figure 33:
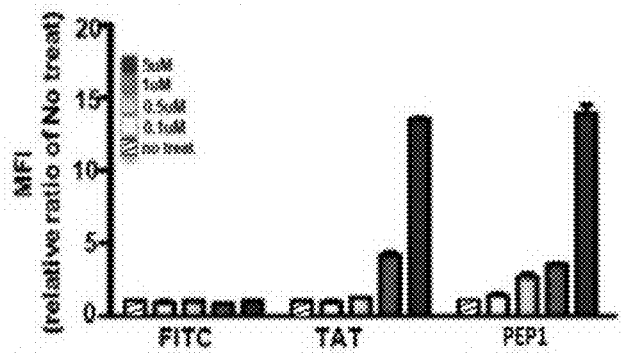
Figure 33:
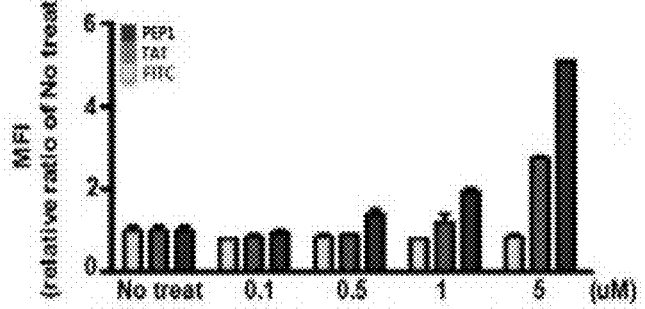
Figure 33:
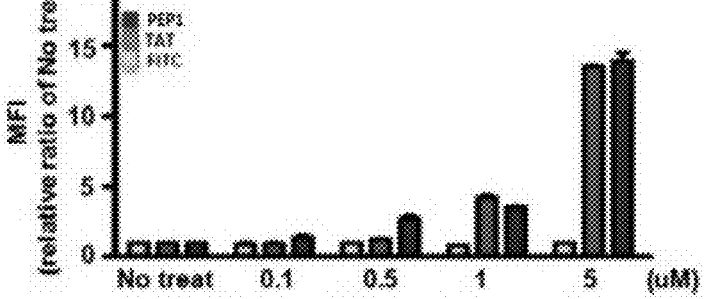
Figure 34:
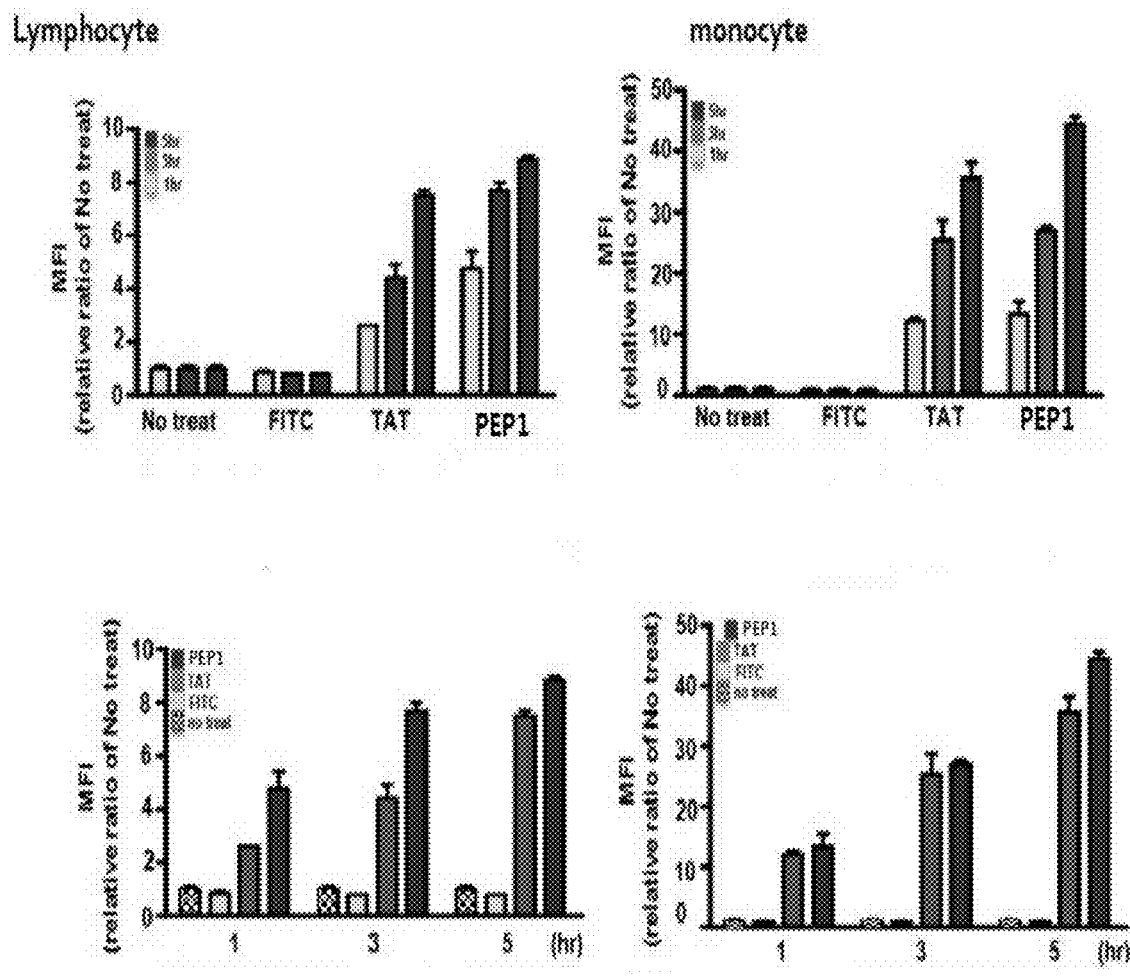

(3) Flow Cytometry Analysis of Cell Penetrating Property of PEP1 Depending on Concentration, Temperature and Time in Human PBMC PBMC separated from human blood was used to treat the peptide depending on concentrations, temperature and time and to analyze the cell penetrating property of the peptide. The result showed that, in the whole PBMC, PEP1 showed cell penetrating property 1.4 times higher than TAT and the cell penetrating properties of both TAT and PEP 1 were increased depending on concentrations and time. In lymphocytes, cell penetrating property of PEP1 was shown to increase by 1.8 times, in monocytes, cell penetrating property of PEP1 was similar to TAT. Depending on concentrations, cell penetrating property of PEP1 was increased in both lymphocytes and the monocytes. Depending on time, cell penetrating property of PEP 1 showed a tendency to increase in both lymphocytes and monocytes, but especially cell penetrating property of monocytes was increased until 3 hours like TAT but by the time of 5 hours, it was increased more than 20% compared to TAT. (FIG. 32 to FIG. 34)

(4) Flow Cytometry of the Peptide by Chemical Treatment in Human PBMC and Jurkat With PBMC separated from human blood, chemical treatment utilization analysis was performed to verify a mechanism of cell penetration. Concentration of chemical treatment was decided based on the data reported in JBC(278 (36), 34141-34149 in 2013. OPTI-MEM was treated with chemical treatment and washed with PBS an hour before PEP1 peptide was treated and flow cytometry analysis was performed.

Figure 35:
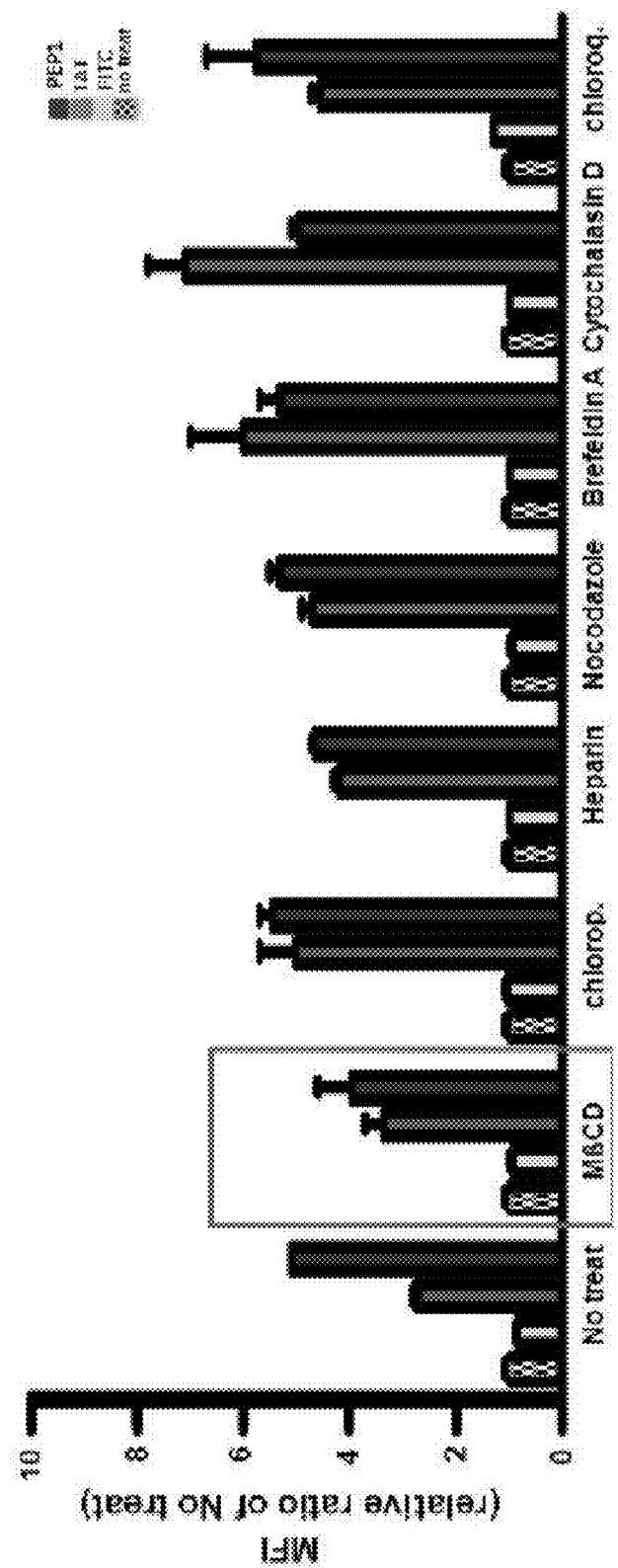
FIG. 35 to FIG. 36 represent the result of flow cytometry analysis of pep1 with chemical treatment in human PBMC and Jurkat.
Figure 36:
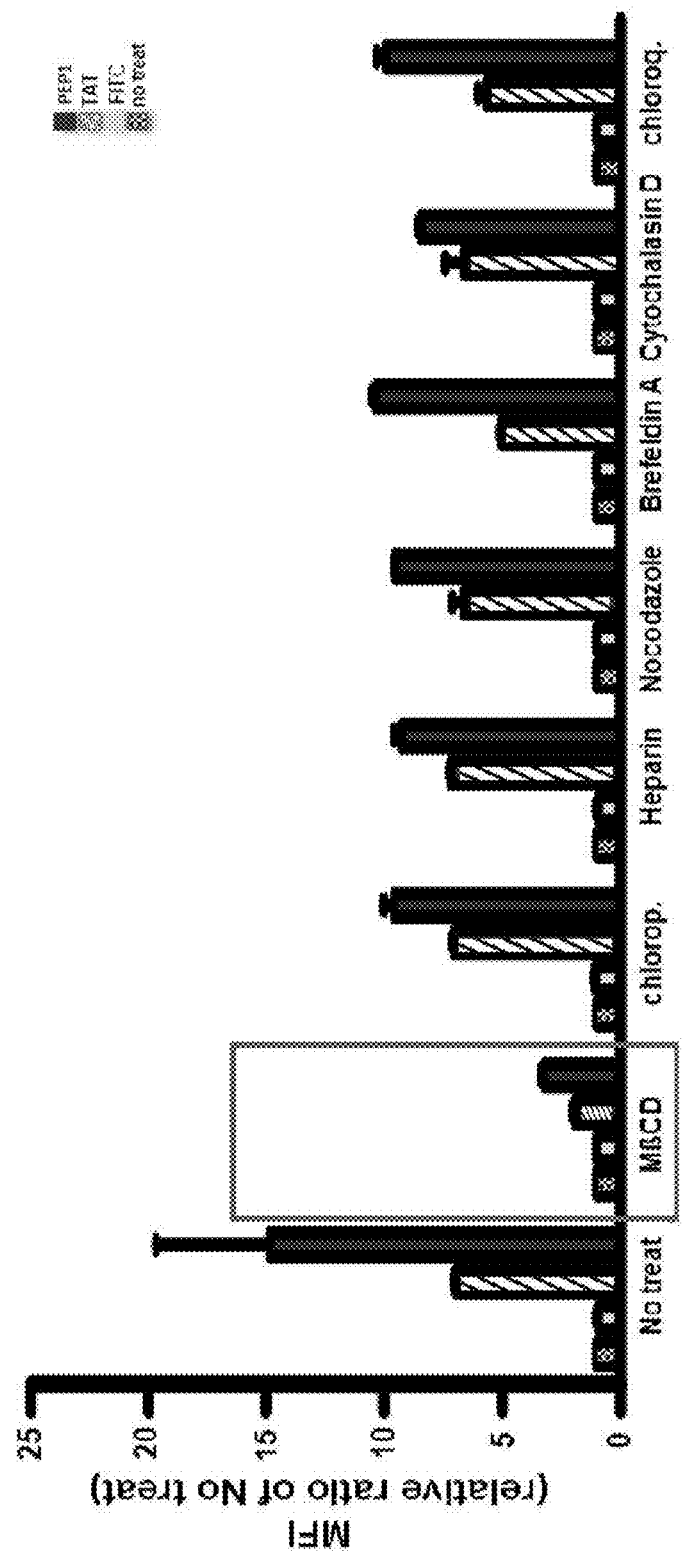

The result showed that in the whole PBMC, When MatCD (plasma membrane cholesterol extraction), treated with PEP1, cell penetrating property was tend to be suppressed and other chemical treatment showed similar tendency. In contrast to this, cell penetrating property of TAT was increased in all cell lines. In Jurkat cell line, MatCD showed a tendency to suppress cell penetrating property. All of the chemical treatment showed a tendency to suppress PEP1 while having no effect on TAT. This verified that PEP 1 was translocated via plasma membrane in PBMC and Jurkat. (FIG. 35 to FIG. 36)

(5) Analysis of Cell Penetrating Property of PEP1 using Various Antibodies

The fact that HSP70/90 plays an important role in cell penetrating property of Pep1 was analyzed using HSP70/90 antibody. Antibodies of GAPDH, HSP70, HSP90 and enolase were treated in PBMC separated from human blood, lymphocyte, and Jurkat to perform flow cytometry. Antibodies of GAPDH and enolase were used as control. When combination and interaction between pep1 and HSP70/90 were suppressed by antibodies, cell penetrating property of the pep1 was remarkably reduced and this supported the fact that HSP70/90 plays an important role in cell penetrating property of PEP1.

To compare and analyze the cell penetrating property of the peptide using various various antibodies, HSP70, enolase, GAPDH (santacruz), HSP90 antibodies were used. Cells were treated with heparin (10 μg/ml), methyl beta cyclodextrin (5 mM), nocodazole (20 μM), Brefeldin A (10 μM), cytochalasin F (5 μM) or choloroqune (100 μM) an hour before cells were cultured by the peptide. After then, cells were washed with PBS, peptide treatment was performed by flow cytometry analysis as the same method described in Example 2. Anti-HSP70, anti-Enolase and anti-GAPDH antibodies were purchased from Santacruz and anti-HSP90 antibody as purchased from Abcam. To analyze the role of each protein in penetration into cells, cells were treated with antibodies corresponding to the proteins with the same method.

Figure 37:
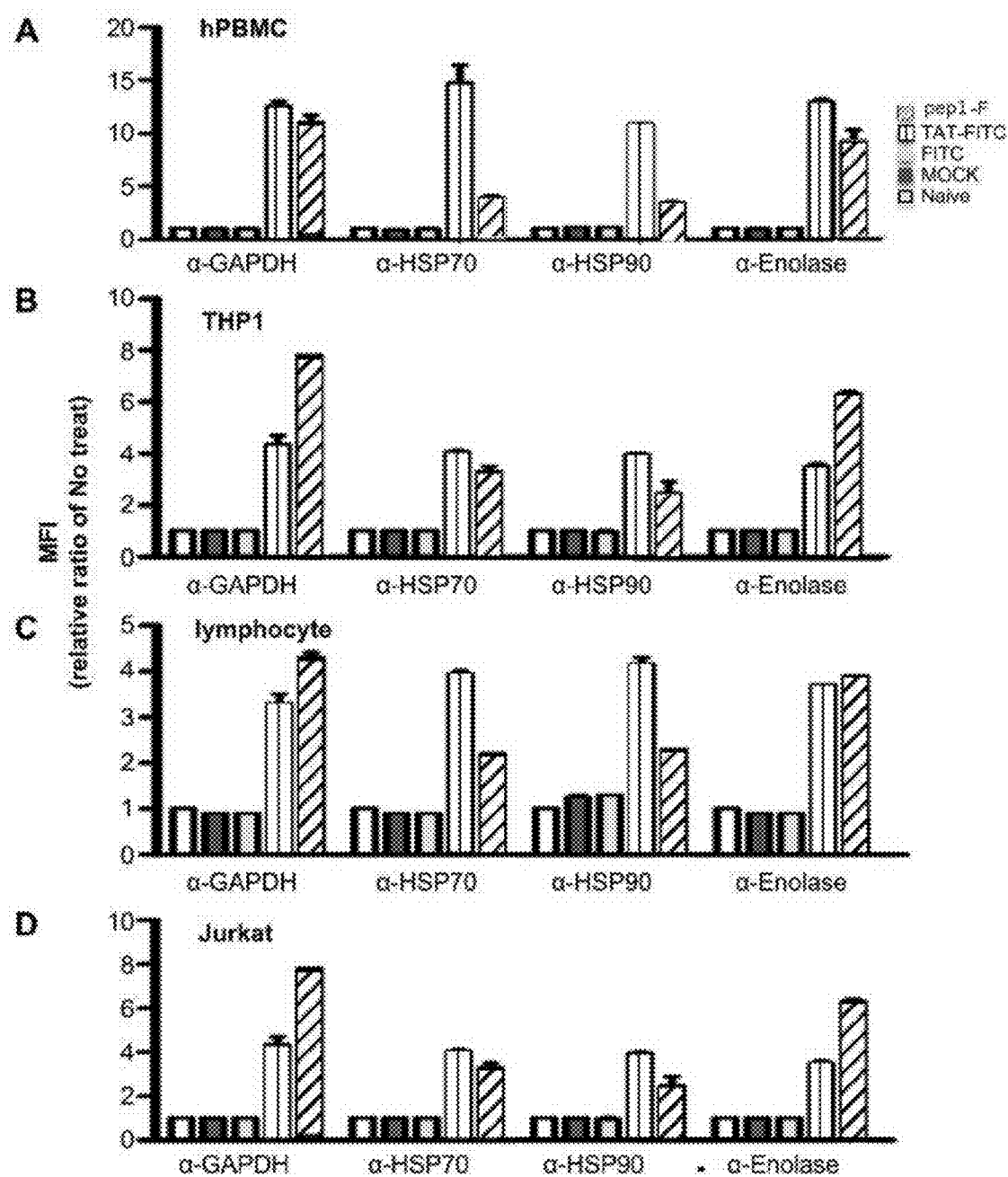
FIG. 37 represents the result of flow cytometry analysis performed to compare cell penetrating property of pep1 by adding various antibodies; wherein the pep1 was treated with antibodies against HSP70, enloase, GAPDH (santacruz), and HSP90.

As shown in FIG. 37, when cells were treated with HSP79 and HSP90 specific antibodies, absorption of GV1001-F into hPBMC was remarkably reduced. On the other hand, it was found that there was no effect on absorption of pep1-F when cells were treated with GAPDA or Enolase specific antibodies, Also, it seemed that cell penetrating property of TAT peptide was not affected when cells were treated with HSP70 and HSP90 specific antibodies and this verified that HSP70 and HSP90 play a specific role in penetration of GV1001 into cytoplasm of a cell. Similar results were shown when experiments were conducted with THP-1, human lymphocytes and Jurkat cells.

Over-expression of HSP90 and HSP70 (DNA and protein expression) has been reported in various cancers. Therefore, pep1 can drag cargoes into the cells more efficiently in cancer cells than in normal cells and thereby it can be suggested that pep1 has the ability to specifically target cancer cells where HSP70 or HSP9 is over-expressed.

Example 4: Cell Penetrating Property of a Conjugate of Ferrocenecarboxylic-CPP

1. Manufacture of a Conjugate of Ferrocenecarboxylic-cpp

The amino acid (8 equivalent) protected with $NH_2$-Lys (Boc)-2-chloro-Trityl Resin and Resin and coupling agent HBTU(8 equivalent)/HoBt(8 equivalent)/NMM(16 equivalent) were melted in DMF for coupling. The DMF solution was added, and reacted in room temperature for 2 hours, then washed with DMF, MeOH, DMF in that order. After then, 20% piperidine in DMF was added for Fmoc deprotection, and reacted in room temperature for 5 minutes, 2 times, then washed with DMF, MeOH, DMF in that order. By repeating above reactions, the basic framework of peptide, ($NH_2$-E(OtBu)-A-R(Pbf)-P-A-L-L-T(tBu)-S(tBu)-R (Pbf)L-R(Pbf)-F-I-P-K(Dde)-2-chloro-Trityl Resin) was made. Hydrazine in 2% of DMF was added to remove Dde which is the protecting group of residues of C-term Lys. After then, Ferrocenecarboxylic acid (Sigma Aldrich cat. #46264, 16 equivalent) and coupling agent HBTU(16 equivalent)/HoBt(16 equivalent)/NMM(32 equivalent) were melted in DMF. The DMF solution was added and reacted in room temperature for 2 hours, then washed with DMF, MeOH, and DMF in that order. TFA/TIS/$H_2O$=95/2.5/2.5 was added to above synthesized peptide resin to separate peptide from resin. Cooling diethyl ether was added to obtained mixture, and centrifugation was used to precipitate gathered peptides. The precipitate was purified by HPLC and confirmed with MS. Then, the peptides were lyophilized.

2. Penetration of Neural Stem Cells

The cortex was removed from the head of an embryonic rat that had been pregnant for 13 days (Sprague-Dawley, SD) (Orient bio, Kyungki, Korea) and cells were divided with $2 \times 10^4$ cells/$cm^2$ in a plate coated with poly-L-ornithine/fibronectin in $Ca^{2-}$/$Mg^{2+}$-free PBS (GIBCO, Grand Island, N.Y., USA). More than 95% of neural stem cells were obtained at 37° C., 5% $CO_2$ environment after 4 to 6 days by treating N2 medium (DMEM/F12, 4.4 IM insulin, 100 mg/l transferring, 30 nM selenite, 0.6 IM putrescine, 20 nM progesterone, 0.2 mM ascorbic acid, 2 nM L-glutamine, 8.6 mM D(+) glucose, 20 nM $NaHCO_3$ (Sigma, St. Louis, Mo.)) daily with 10 ng/ml of BFGF (basic fibroblast growth factor).

Above obtained neural stem cells were divided in a chamber well plate with $1 \times 10^5$. The cells in the plate were treated with 10 μM of Ferrocencarboxylic-pep1 and cultured in 37° C., 5% $CO_2$ incubator. The cells were washed with PBS twice and fixed with 4% Paraformaldehyde in room temperature for 20 mins. The nucleus of cells was dyed with DAPI (4',6-diamidino-2-phenylindole) mount medium (mount medium with DAPI) (Vector Laboratories, CA, USA). After then, cells were compared and analyzed by Confocal laser scanning system at a blue wavelength of 430-500 nm, a red wavelength of 620-700 nm, and a combination wavelength of red and blue.

Figure 38:
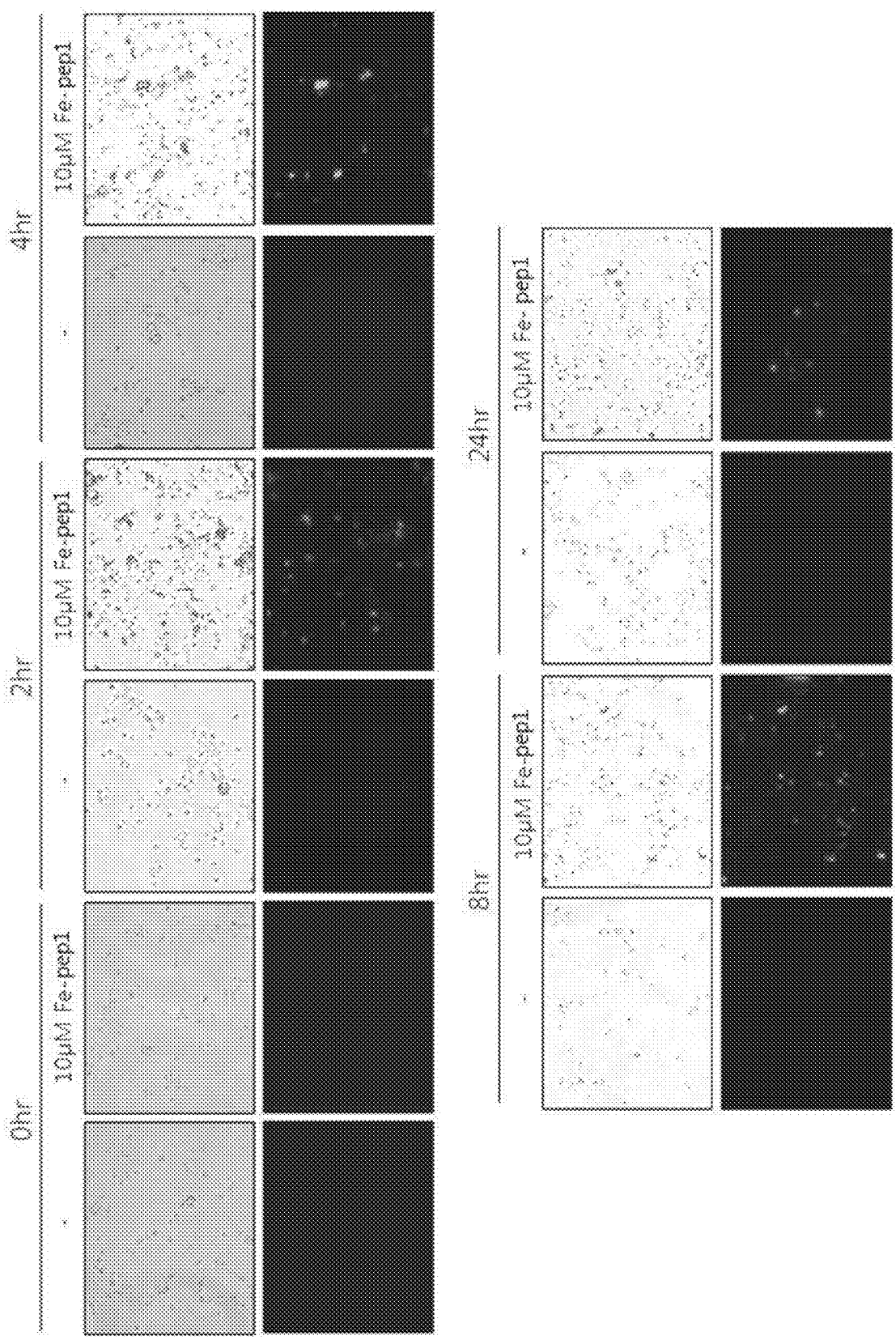
FIG. 38 is a diagram which represents the cellular uptake of Ferrocenecarboxylic-pep1 in rat neural stem cells (NSC) over time.
Figure 39:
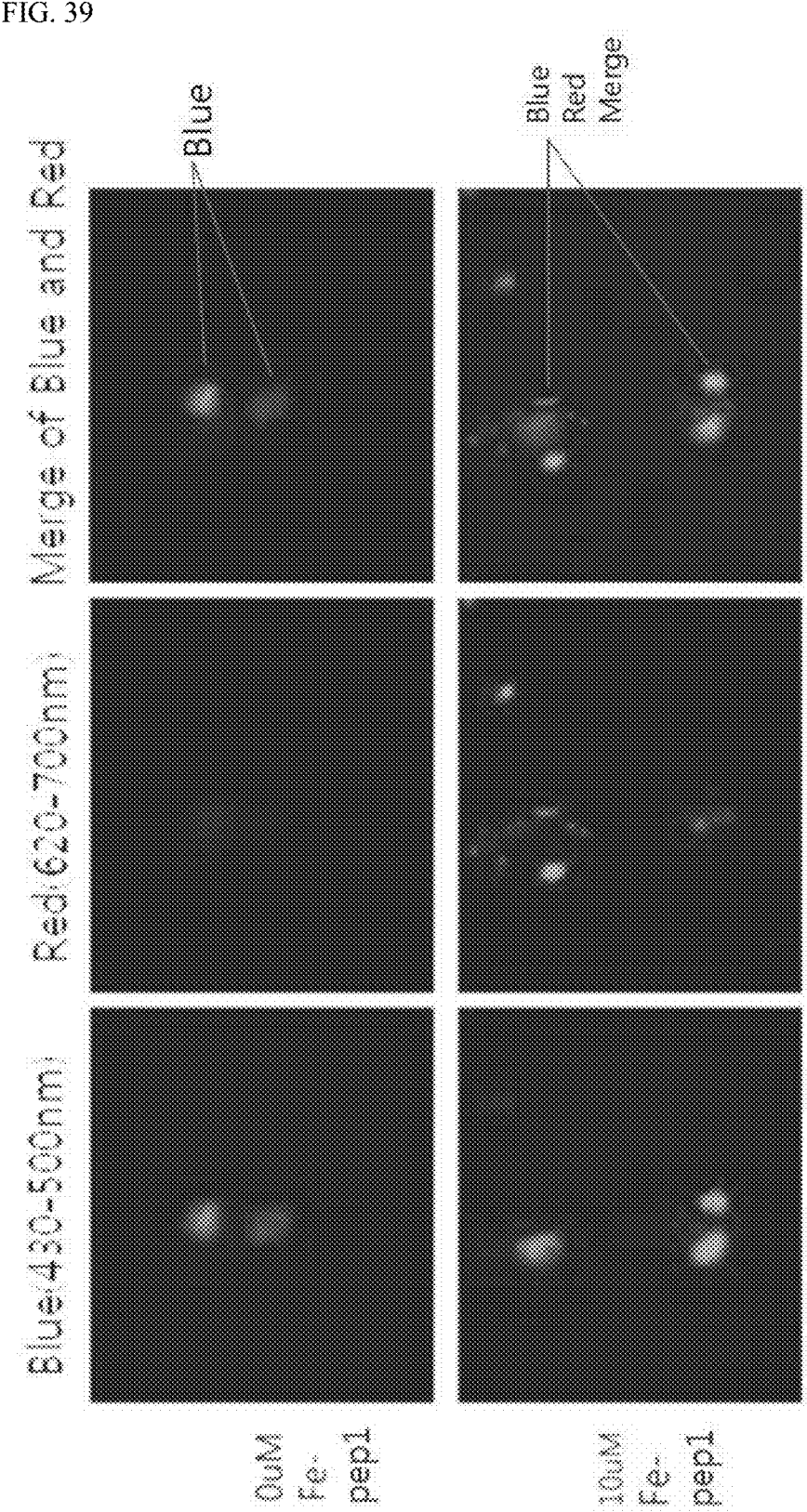
FIG. 39 is a diagram which represents the cellular uptake of Ferrocenecarboxylic-pep1 in rat NSC measured by confocal laser scanning system DAPI was used to stain the nucleus. Ferrocenecarboxylic-pep1 and dying cell nucleus with DAPI.

The results are shown in FIG. 38 and FIG. 39.

FIG. 38 is a diagram representing status of neural stem cells over time after being treated with Feroocenecarboxylic-pep1.

As shown in FIG. 38, the result of the analysis showed that 10 μM of Ferrocenecarboxylic-pep1 penetrated into the cell from 2 hours and large quantities of cells were penetrated into the cell over time.

FIG. 39 is a diagram representing penetration status of neural stem cells taken by Confocal laser scanning system; wherein the neural stem cells were treated with Ferrocenecaroxylic-pep1 and the nucleus of the cells was dyed with DAPI. In FIG. 39, the part represented as blue at a wavelength of 430-550 nm is the nucleus dyed with DAPI and the part represented as red at a wavelength of 700 nm is Ferrocenecarboxylic-pep1. As shown in the diagram of a combination wavelength of the red and blue, Ferrocenecarboxylic-pep1 is clustered around the nucleus and this shows that Ferrocenecarboxylic-pep1 penetrated into the cell and translocated into the cytoplasm.

3. Toxicity Assessment

For toxicity assessment of pep1 itself which was conjugated with Ferrocenecarboxylic acid, neural stem cells were divided with $4 \times 10^4$ and $2.5 \times 10^5$ in a 96 well and a 24 well-plate respectively, and cultured for at least 12 hours at 37° C., 5% $CO_2$ incubator. Different concentrations (0, 0.01, 0.1, 1, 10, 100 μM) of Ferrocenecarboxylic-pep1 were treated and cultured for 24 hours followed by cell viability and toxicity assessments using cell counting kit-8 (CCK-8) assay and lactate dehydrogenase (LDH) activation assays. The result is shown in FIG. 40.

Figure 40:
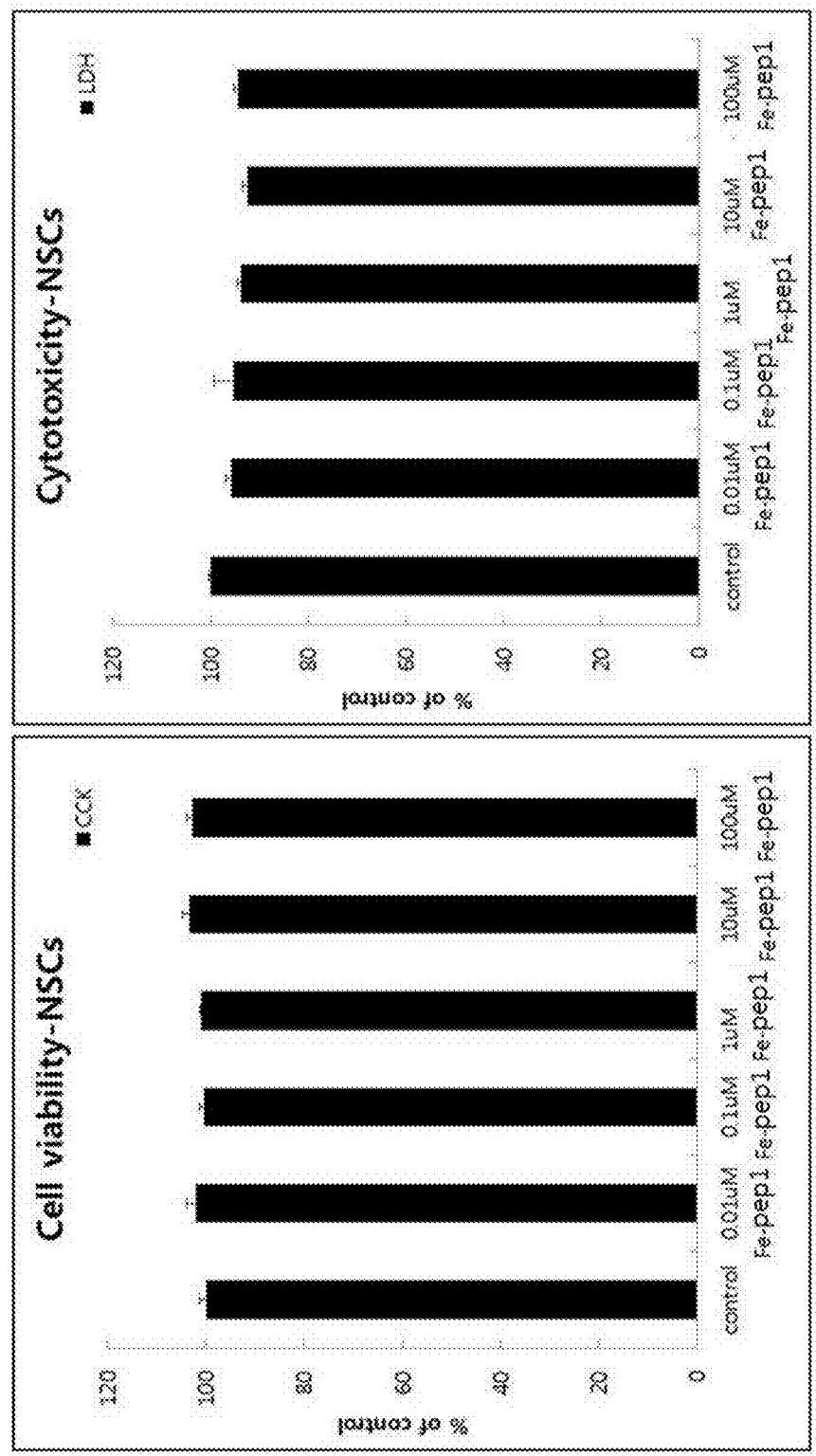
FIG. 40 represents the effects of Ferrocenecarboxylic-pep1 oncell viability and cytotoxicity analyzed by cell counting kit-8 (CCK-8) assays and lactate dehydrogenase (LDH) activation assay.

As shown in FIG. 40, it was verified that there was no effect on cell viability and toxicity of neural stem cells at each concentration (0, 0.01, 0.1, 1, 10, 100 μM).

4. In-Vivo Experiment

A. Preparation of Neural Stem Cells $5 \times 10^6$ of neural stem cells obtained from above Experiment (2), were divided in 100 mm dish. 10 μM of Ferrocenecarboxylic-pep1 was treated and cultured at 37° C., 5% $CO_2$ incubator for 24 hours and cells were separated from TrypLE (GIBCO) plate and washed with free media. 10 μl of $3 \times 10^5$ Ferrocenecarboxylic-pep1 labeled neural stem cells per one head was prepared.

B. Transplantation of Neural Stem Cells Treated with Ferrocenecarboxylic-cpp

All the animal experiments disclosed herein were conducted after receiving approval approval from IACUC of Hanyang University, Korea. SD rats of 8 weeks were purchased and after an adaptation period of one week, rats of 290 g±15 g body weight were used in the experiment. Experiments were conducted with animals of 4 different groups, for example, NSCs with Ferrocenecarboxylic-pep1 group, NSCs without Ferrocenecarboxylic-pep1 group, Ferrocenecarboxylic-pep1 group and Saline group. When transplanting cells, Ferrocenecarboxylic-pep1 or saline to each group, they were transplanted within the brain of SD rats using stereotaxic surgery. Before the transplantation, rats were anesthetized with ketamin and rompun, and the parts of the skull were removed by grinding the scalp after shaving. Ferrocenecarboxylic-pep1 or Saline were stereotaxically transplanted on a coordinate of AP=+0.7, R=+2, V+−5.5.

C. MRI Imaging

MRI imaging was used to observe transplanted NSCs and Ferrocenecarboxylic-pep1 in vivo. MRI imaging was performed 3 days after transplantation and Best 3T MRI of Philips was used. Ketamin and rompun were used to anesthetize rats and MRI imaging was taken using multiplanar gradient-recalled pulse sequence (TR=596 ms, TE=16 ms, section thickness=0.7 mm, in-plane resolution: 292×290 μM (resolution size 0.0593 mm³), and number of acquisitions=1.

Figure 41:
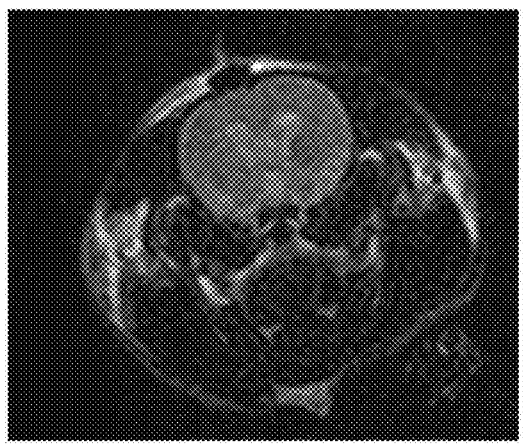
FIG. 41 is a brain MRI image diagram of brain of stem cells with Ferrocenecarboxylic-pep1 group treated with Ferrocenecarboxyic-pep1.
Figure 41:
Figure 42:
FIG. 42 is a MRI diagram of brain stem cells with Ferrocenecarboxylic-pep1 group not treated with Ferrocenecarboxylic-pep1.
Figure 42:
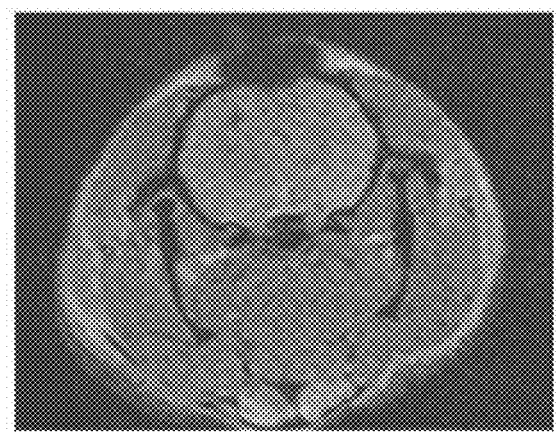
Figure 43:
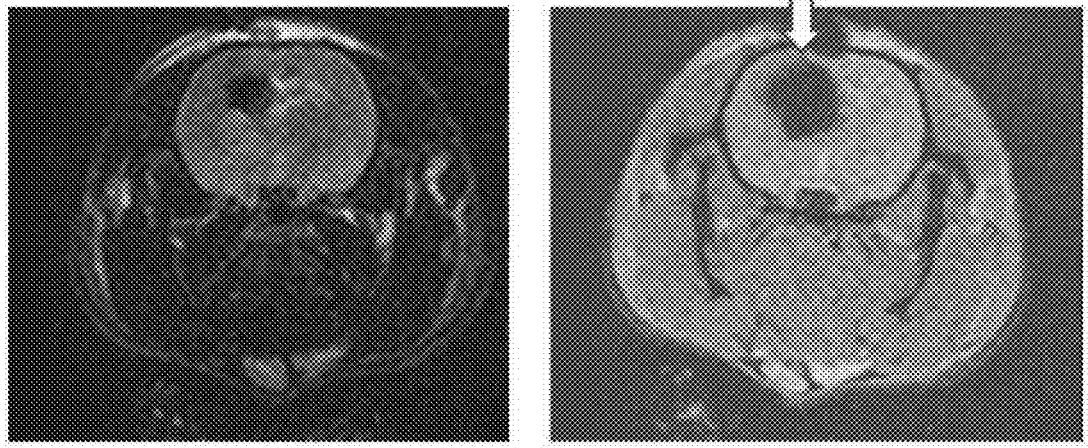
FIG. 43 is a MRI diagram of brain of Ferrocenecarbxylic-pep1 group.
Figure 44:
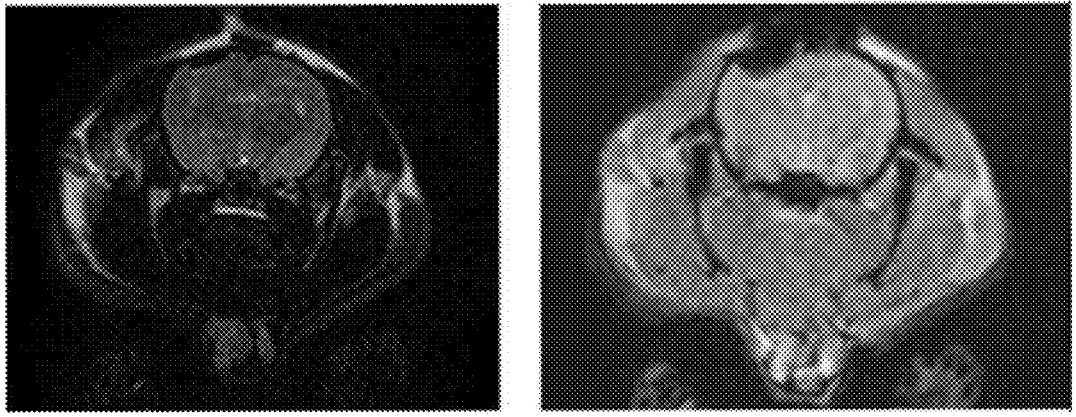
FIG. 44 is a MRI diagram of brain of saline group.

The results are shown in FIG. 41 to FIG. 44. FIG. 41 is a MRI image representing a brain which stem cells with Ferrocenecaroxyolic-pep1 group was transplanted and FIG. 42 is a MRI image representing the brain which stem cells without Ferrocenecarboxylic-pep1 were transplanted, FIG. 43 is a MRI image representing a brain which Ferrocenecarboxylic-pep1 group was transplanted and FIG. 44 is a MRI image representing a brain which saline group was transplanted. As shown in FIG. 41 to FIG. 44, detection of neural stem cells treated with Ferrocenecarboxyli-pep1 is outstanding compared to neural stem cells not treated with Ferrocenecarboxylic-pep1. On the other hand, detection of a brain with Ferrocenecarboxylic-pep1 group was transplanted (FIG. 43) was outstanding compared to a detection of a brain where Saline group was transplanted (FIG. 44).

Example 5: Cell Penetrating Property of PEP1 to Transport Macro-Molecules (Proteins, DNA and siRNA)

1. Cell Penetrating Property of CPP-GFP Conjugate (1) Manufacture of CPP-GFP Conjugate A conjugate of a peptide of SEQ ID NO: 1 and Green Fluorescent protein was manufactured as follows.

Figure 45:
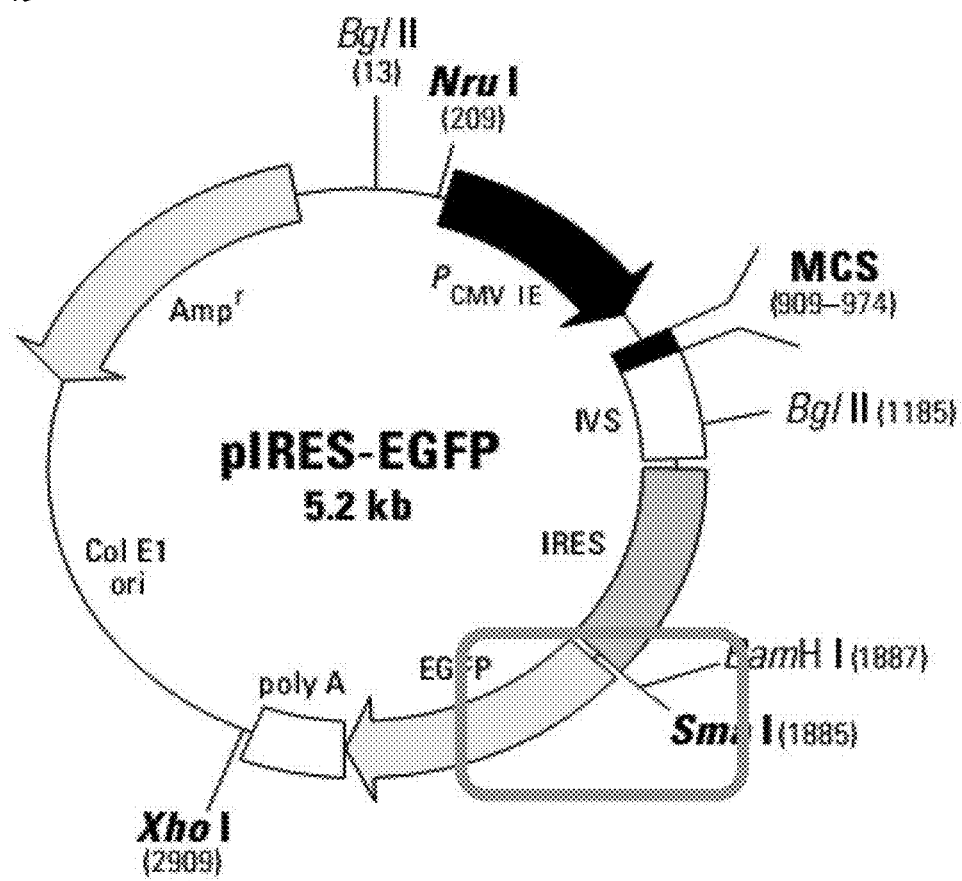
FIG. 45 represents a pET28a(+) vector (Promega) to generate a conjugate of the peptide with SEQ ID NO: 1 and Green Fluorescent Protein (GFP).

Firstly, as shown by FIG. 45, primers were produced to clone Green Fluorescent proteins (SEQ ID NO: 6, SEQ ID NO: 7) in pET28a(+) vector (Promega). Primer was produced to have EcoRI restriction site at 5', HindIII restriction site at 3', 21 bp of GFP 신반부 sequences at next to the part EcoRI restriction site was added, a stop codon at next to the part HindIII restriction site was added. For production of DNA of GFP-CPP protein, the 5' was produced same as GFP and the front of GFP was produced to have sequences coding the CPP. For example, in the case of the peptide of SEQ ID NO: 1, it was produced to have the following sequences: GAA GCG CGC CCG GCG CTG ACC AGC CGC CTG CGC TTT ATT CCG AAA (SEQ ID NO: 3). Examples for comparison, to produce TAT-GFP, the following sequences; TAT GGT CGT AAA AAA CGT CAA CGT CGT CGT (SEQ ID NO: 11), were added to the front of GFP.

EGFP was obtained by PCR using the vector represented as a diagram in FIG. 45 as a template. When producing a primer, 16p is attached to the front of EGFP in a case of EGFP-16p (GAA GCG CGC CCG GCG CTG CTG ACC AGC CGC CTG CGC TTT ATT CCG AAA). In a case of EGFP-TAT, TAT is produced to the front of EGFP when producing a primer TAT.

When expressing the primer in *E. coli* 16P and TAT are modified for *E.coli* codon usage.

Figure 46:
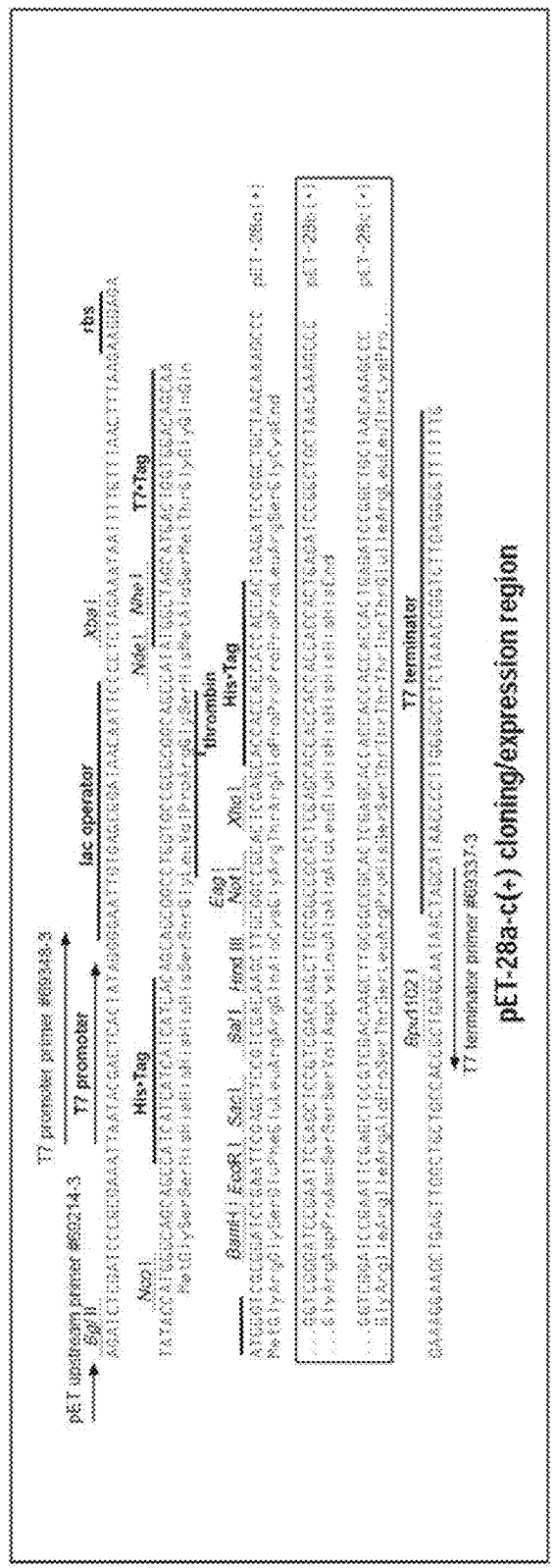
FIG. 46 represents a map of pET-28a vector and FIG. 47 is a diagram of cloning.
Figure 47:
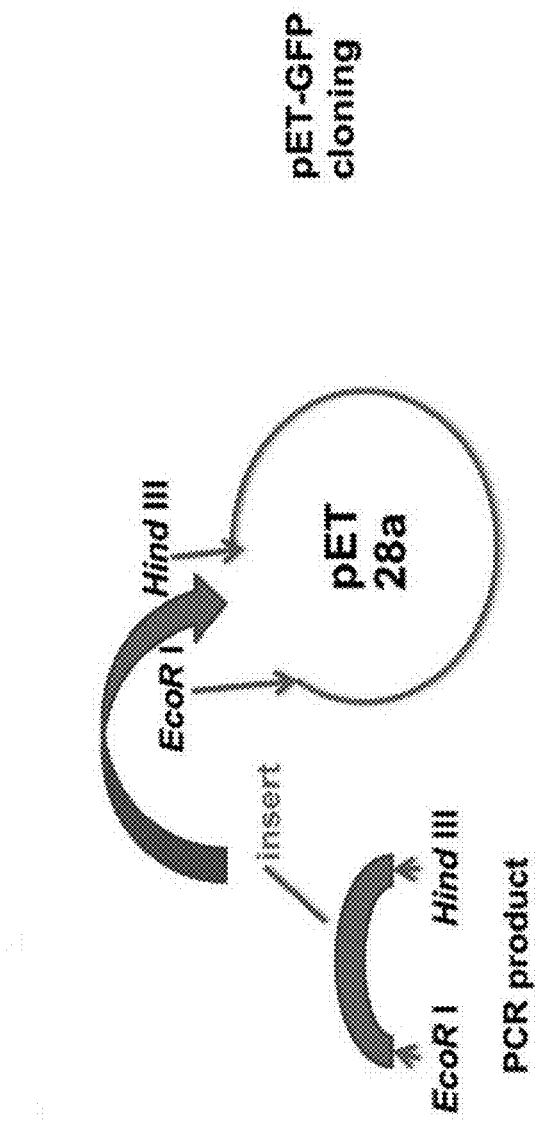

FIG. 46 is a mimetic diagram representing pET-28a vector. FIG. 47 is a mimetic diagram of cloning.

The forward primer was produced by adding 21 GFP sequences behind the CPP coding sequences and the reverse primer was produced by adding parts of C-terminal sequences of GFP, using the above primer and pET-28a-GFP vector as a template, and PCR was performed. PCR was performed at 95° C., 5 min, 30 cycle 95° C. 5 min (denaturation), 63° C. 30 sec (annealing), 72° C. 7 min and 10 pmol of each primer was used. Fragments of GFP, GFP-CPP DNA were amplified at above PCR conditions, and fragments were cloned at EcoRI and HindIII part of pET28a(+) vector and the vector expressing GFP, GFP-CPP was obtained. (FIG. 47)

Figure 48:
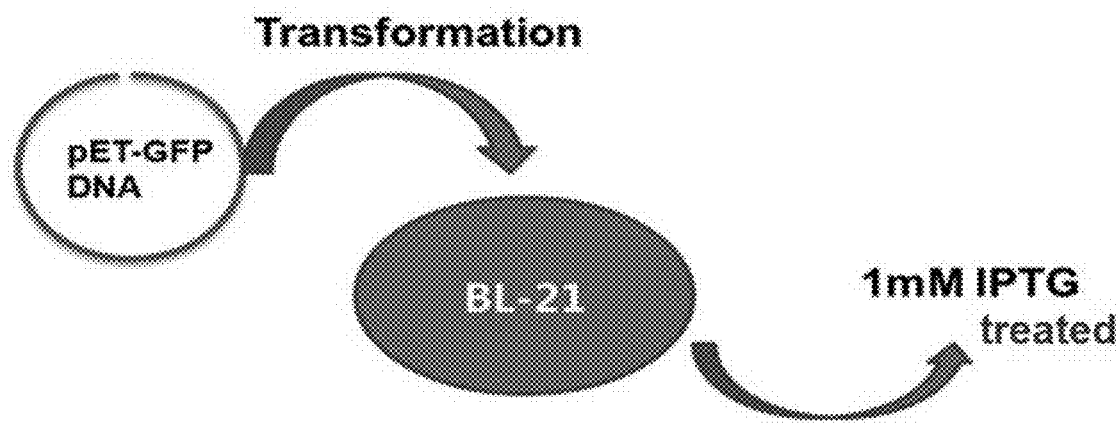
FIG. 48 shows the cloning strategy used to generate GFP expression plasmid in pET vector.

Protein was separated by transforming above vector in bacteria. Specifically, *E. coli* *E. coli* BL21(DE3) (Invitrogen, Carlsbad, Calif., USA) was transformed with each of above vector and grown in a 5 ml of LB/Kanamycin and moved to 100 ml medium and cultured in the medium. Kanamycin was added at volume ratio of 1/1000. The vector was spinner cultured at 37° C. for 2 to 3 hours and was grown until within 0.6-0.8 range by measuring absorbance and 10 mM of IPTG (Isopropyl beta-D-1-thiogalactopyranoside) was treated. The vector was cultured for additional 3~4 hours and centrifugated at 5000 rpm for 5 minutes. (FIG. 48)

Figure 49:
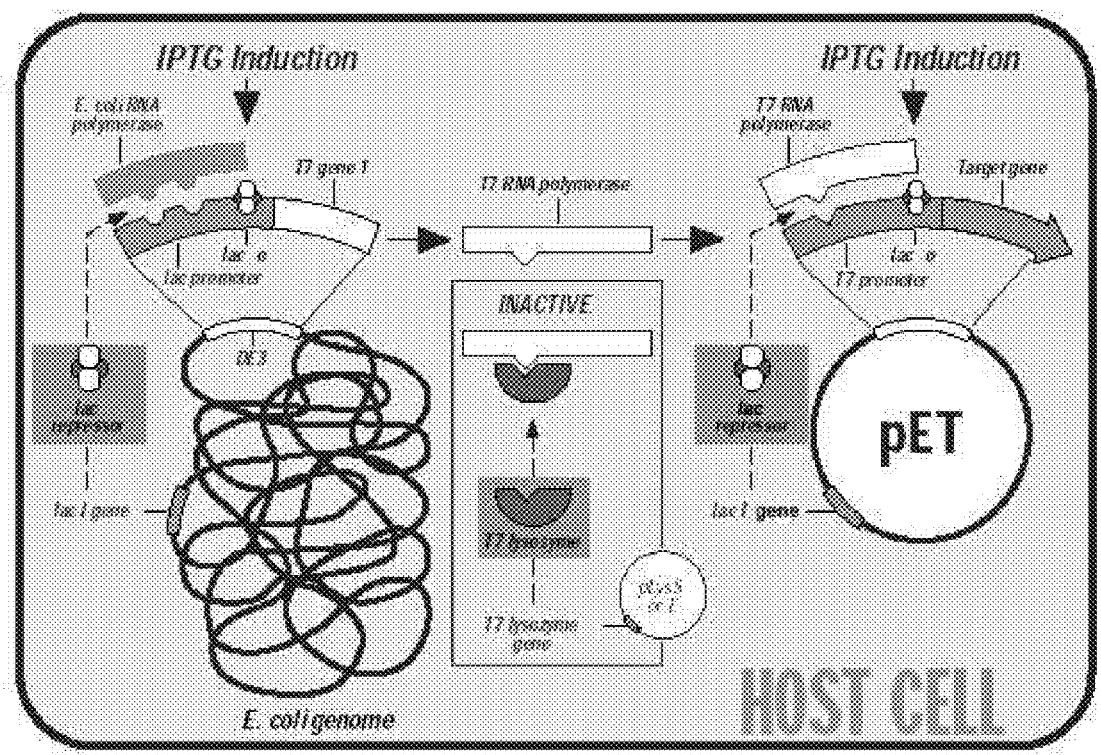
FIG. 49 shows a principle of IPTG induction in bacterial transformation.

The principle of treatment of 1 mM IPTG herein is as follows. The conditions of treatment is that before treating IPTG, BL-21 transformant (100 ml) was grown at 37° C. for 2-3 hours with O.D about 0.6-0.8, and protein was extracted. In the case of EGFP-TAT, after treatment with IPTG, EGFP-TT was o/n at 16° C. Purified protein can be obtained from the sample using His tag purification method. (FIG. 49)

The result of centrifugation of expressed protein showed over-expression of protein represented as green can be confirmed visually. The over-expressed protein was separated using protein separation kit (Prod, #21277, Thermo Scientific, IL, USA), His tag purification kit, according to the manufacturer's instructions.

After separation, proteins were dialyzed purified and concentrated. Specifically, proteins were purified using sterilized 4° C. PBS. Firstly, dialysis bag was balanced with PBS, above separated protein solution was added to the bag with 5 ml syringe, and dialyzed at 4° C. by stirring. To increase concentration of protein and to remove unnecessary substances, the dialyzed proteins were concentrated by centrifugation at 3,000 rpm 4° C. in BIBASPIN 20 (Prod, #VS2092, Sartorius Stedin biotech, Germany).

(2) Cell Line Culture $5 \times 10^5$ of cell line was divided in a 6-well plate using HepG2 cells (human hepatocellular carcinoma cells) obtained from ATCC and cultured in MEM medium containing 10% fetal bovine serum (Invitrogen, USA), 100 µg/ml penicillin, 100 units/ml streptomycin at 37° C., 5% $CO_2$ incubator for 12 hours. Each CHO (Chinese Hamster Ovary cells), HeLA (human cervical cancer cells), Huh? (human hepatocellular carcinoma cells), MCF7 (human breast cancer cells) cell line was cultured in each MEM RPMI 1640 medium containing 10% fetal bovine serum (Invitrogen, USA), 2 mmol/ml L-glutamin, 100 µg/ml penicillin and 100 units/ml streptomycin at 37° C., 5% $CO_2$ incubator.

(3) Fluorescence Microscope

Figure 50:
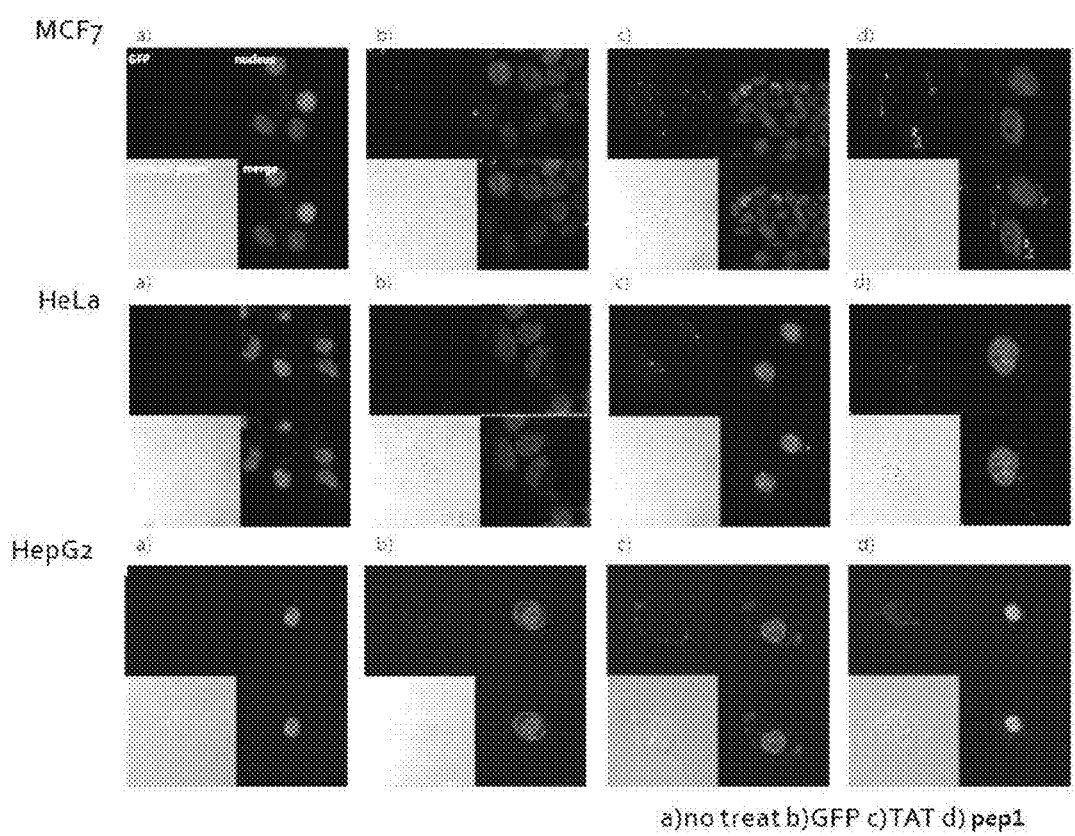
FIG. 50 represents the result of cell penetrating property of GFP combined with pep 1 in pep 1 in various cell lines analyzed by a fluorescence microscope.

After washing cell line with PBS, starvation was induced for an hour in OPTI-MEM. MEM. 1 uM of GFP (SEQ ID NO: 6, SEQ ID NO: 7), TAT (YGRKKRRQRRR)-GFP (manufactured in Example 5.1(1)), pep1-GFP (manufactured in Example 5.1(1)) were treated and cultured at 37° C., 5% $CO_2$ incubator for 18 hours. After washing cell line with PBS, cells were observed at 488 nm wherein they were divided in 1 ml of PBS. Fluorescence microscope analysis showed penetration of TAT into the cell and localization in the nucleus and localization of pep1 in the cytoplasm. The result confirmed that pep1 has higher cell penetrating property in MCF cell line than TAT and after penetration of the cell; pep1 was localized in the cytoplasm. (FIG. 50)

(4) Flow Cytometry

Figure 51:
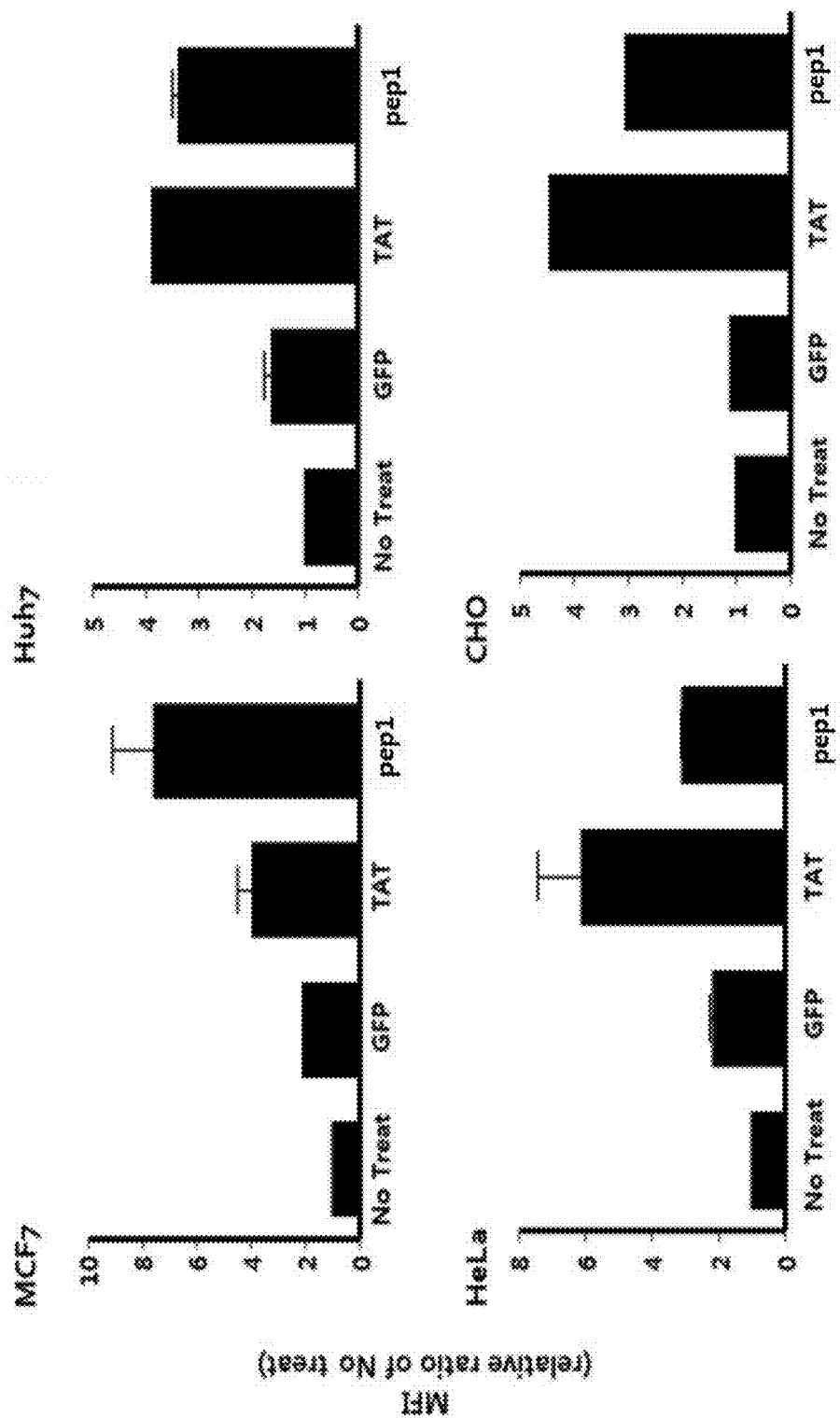
FIG. 51 represents the result of flow cytometric analyses showing cellular uptake of GFP, TAT, and pep1 in various cell lines.

After washing cell line with PBS, starvation was induced for an hour in OPTI-MEM. 1 uM of GFP, TAT-GFP and 16merGFp were treated and cultured at 37° C., 5% $CO_2$ incubator for 2 hours. After repeating the step of washing with PBS 3 times, cell lines were suspended in 0.5 ml 1×FACS buffer and fluorescence of them was analyzed with FACS Calibur (Becton Dickinson). Cellular uptake aspects of GFP, TAT-GFP and pep1-GFP were compared and analyzed with untreated cell lines as control. GFP combined with pep1 was treated with various cell lines and flow cytometry was performed. The result showed that cellular uptake of pep1 was increased more than 2 times than TAT in MCF7 cell line, but in other cell lines, the cellular uptake of pep1 was not higher than TAT. (FIG. 51)

Figures 52, 53:
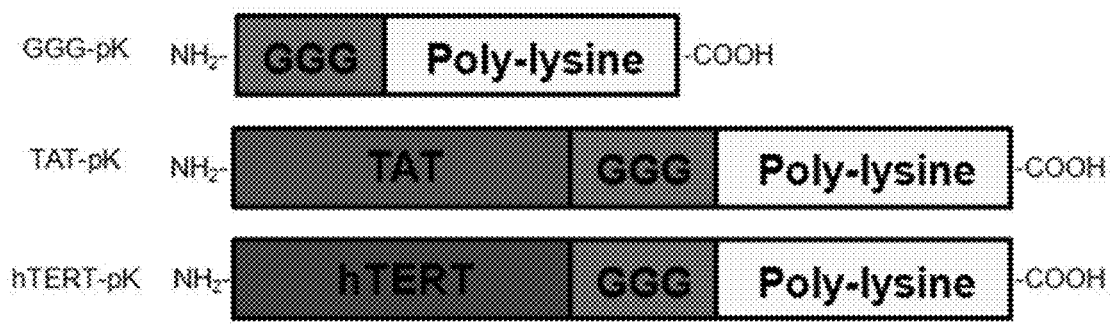
FIG. 52 represents the primary structure of peptide used to generate DNA (poly-lysine)-cpp conjugate.
FIG. 53 is a schematics of the poly-lysine conjugates in FIG. 52.

2. Cell Penetrating Property of DNA Conjugate (1) Manufacture of DNA (poly-lysine)-CPP The peptides with previously known cell penetrating property (GGG, TAT) and telomerase derived peptide, hTERT, were combined with 15mer lysine. Cations are abundant in polylysine and therefore they combine well with anionic DNA. Peptide synthesis was carried out by Peptron, the synthesized peptide was diluted with distilled water with concentration of 1 mg/ml. FIG. 52 represents the primary structure of peptide used in the experiment.

FIG. 53 is a mimetic diagram of peptide used in the experiment.

(2) Cell Line Culture

Each CHO (Chinese Hamster Ovary cells), HeLA (human cervical cancer cells), Huh7 (human hepatocellular carcinoma cells), MCF7 (human breast cancer cells) cell line was cultured in DMEM, MEM and RPMI 1640 medium respectively containing 10% fetal bovine serum (Invitrogen, USA), 2 mmol/ml L-glutamin, 100 µg/ml penicillin and 100 units/ml streptomycin at 37° C., 5% $CO_2$ incubator.

(3) Gel Electrophoresis

To investigate combination degree of DNA-peptide complex, 0.05-5 ug of peptide and 0.5 ug of Generuler 1 kb DNA ladder (Fermentas) was mixed and was on standby in room temperature for 10 mins. DNA-peptide complex was injected into 1% agarose gel containing 0.5 mg/ml Ethidium Bromide (EtBr) and reacted at 100 v in 1×TAE buffer for 30 mins.

Figure 54:
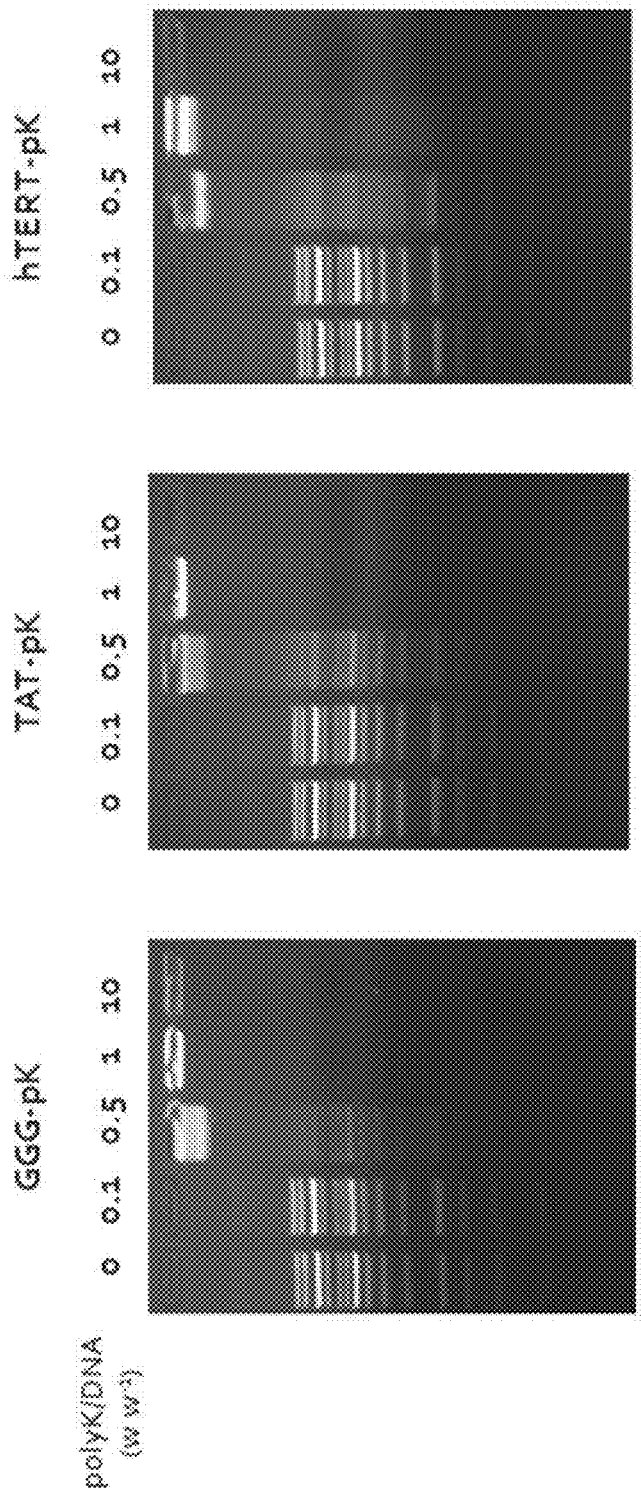
FIG. 54 represents the electrophoretic mobility of DNA combined with the peptide.

The result of electrophoresis of peptide-DNA complex showed that all of peptides were combined well with DNA (FIG. 54). When the peptides and DNA are well combined, immobilization of DNA takes place as DNA is neutralized. According to the result of this experiment, immobilization was observed when (w/w) is more than 1.

(4) Analysis of Transport Ability of Luciferase using pep1 Peptide.

$5 \times 10^4 \sim 1 \times 10^5$ of above specified cell line was cultured in each well of a 12-well plate and washed with PBS and the medium was placed with OPTI-MEM. piRES2-EGFP vector was produced by inserting luciferase DNA to OPTI-MEM and pIRES2-EGFP vector. 2 ug of pIRES2-EGFP luciferase vector was mixed with 1, 2, 4, 8 multiple (w/w) of each peptide and the complex of 100 ul/well total volume was produced. The produced DNA-peptide complex was inserted into each well and cultured at 37° C., 5% $CO_2$ for 4 hours. After washing cells, medium was replaced with complete media and was cultured at 37° C., 5% $CO_2$ for additional 20 hours. The medium was removed 24 hours after DNA-peptide complex injection, and after washing the cells with PBS twice, 50 ul of lysis buffer was injected into each well. The luciferase assay was performed on cell lysate obtained from cell shaking for 15 minutes in room temperature. Luminescence was measured by adding 100 ul of luciferase substrate to 20 ul of cell lysate. The result recorded the average value standardized by BSA assay.

Figure 55:
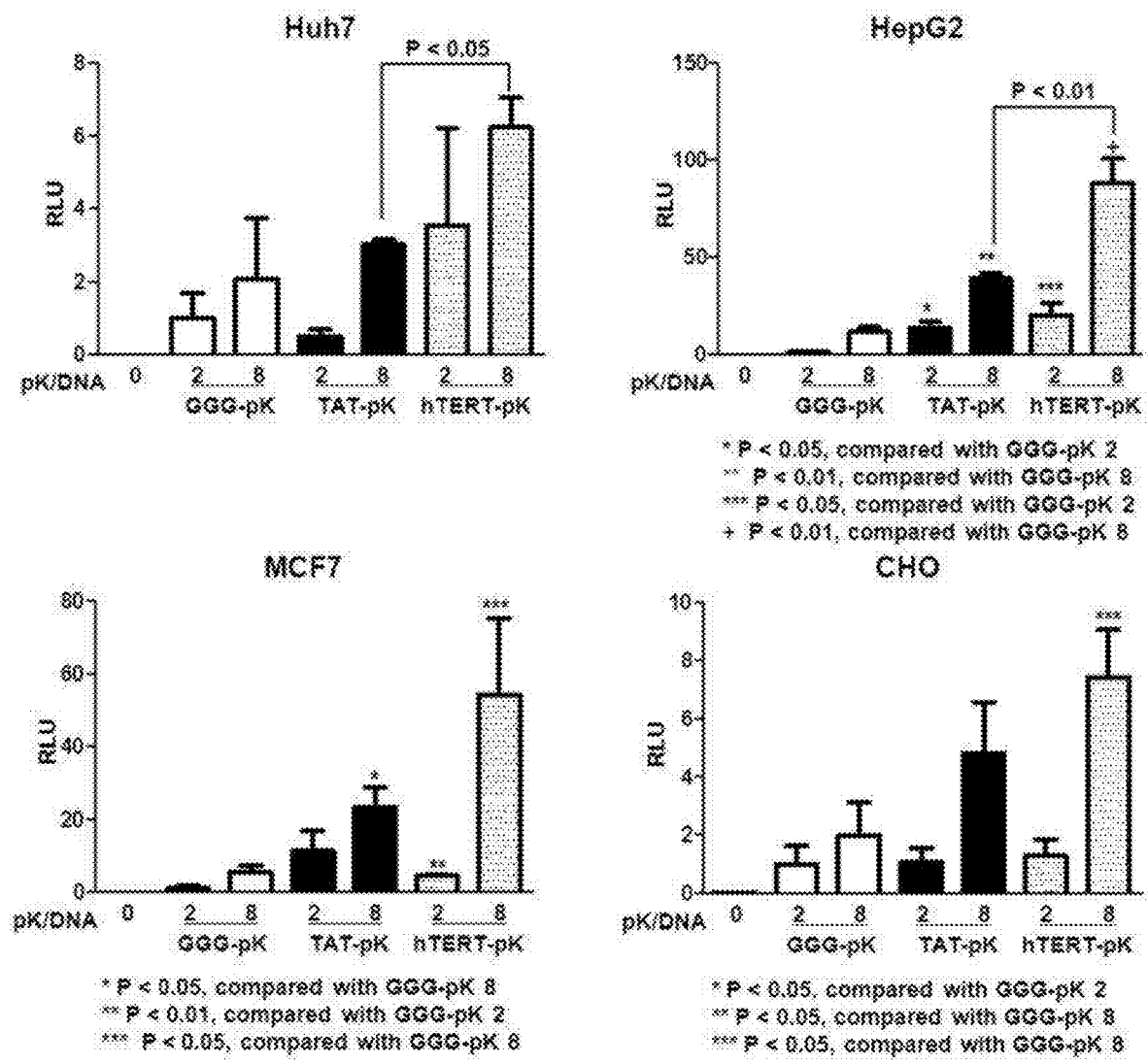
FIG. 55 represents the result of cell penetrating property of DNA delivered by pep1 conjugated to poly-lysine, as measured by hTERT-dependent luciferase assay in various cell lines.

The result of luciferase analysis verified that hTERT-pk showed higher luciferase expression than control groups (TAT-pK, GGG-pK) at all concentration. Especially, at a concentration of 8 times compared to DNA, hTERT-pK showed a significant level of luciferase expression compared to TAT-pK and GGG-pK. (FIG. 55)

3. Cell Penetrating Property of SiRNA-CPP (1) Manufacture of siRNA-CPP Conjugate The basic framework of the peptide, Trt-Mercaptoacetyl-Ahx-E(OtBu)-A-R(Pbf)-P-A-L-L-T(tBu)-R(Pbf)L-R(Pbf)-

F-I-P-K(Boc)-2-chloro-Trityl Resin was manufactured according to the manufacturing methods described in the Example 1. Ahs herein means 6-aminohexanoic acid. The synthesis of manufactured Trt-Mercaptoacetyl-Ahx-E (OtBu)-A-R(Pbf)-P-A-L-L-T(tBu)-R(Pbf)L-R(Pbf)-F-I-P-K(Boc)-2-chloro-Trityl Resin was verified by HPLC and mass analysis.

SiLuc-pep1 conjugate was manufactured by conjugation of siRNA sequences with above synthesized pep1. Specifically, siRNA sequences used in conjugation with pep1 are as follows.

```
SiLuc sense (5'→3'):
                                         (SEQ ID NO: 4)
CUUACGCUGAGUACUUCGA (dTdT)

SiLuc anti-sense (5'→3'):
                                         (SEQ ID NO: 5)
UCGAAGUACUCAGCGUAA (dTdT)
```

The manufacturing method is that Maleimide modified SiLuc (75 umol) supplied by Bionia, Korea was melted in PBS buffer (1×1 ml) and was conjugated by reacting in room temperature for 2 hours. Conjugation was performed by reacting thiol group of the peptide and Maleimide of siRNA. Conjugation reaction was verified using Ellman's reagent and 5,5'-dithiobis-(2-nitrobenzeoic acid or DTNB). Ellman's reagent is a chemical used to quantify concentration or number of thiol groups in a sample.

siRNA sequences used in the experiment are for luciferase DNA purpose and siRNA of siRNA of siLuc-scrambled pep1 [siLuc conjugation with Mercaptoacetyl-Ahx-LRALPK-RPFISRLTEA], siLuc-Tat(47-57) [siLuc conjugation with Mercaptoacetyl-Ahx-YGRKKRRQRRR], siLuc-Penetratin [siLuc conjugation with Mercaptoacetyl-Ahx-RQIKIWF-QNRRMKWKK], siLuc-pep1 [siLuc conjugation with Mercaptoacetyl-Ahx-EARPALLTSRLRFIPK]provided by Peptron where we asked for peptide synthesis. Si0Cont-scrambled pep1, siCont-Tat (47-57), siCont-Penetratin, siCont-pep1 were used as control. Luciferase siRNA and negative siRNA (Cat #: SN-1012, AccuTarget Negative control siRNA) which are commercially sold by Blonia were used as a positive control and a negative control respectively.

Sequences of siRNA are as follows.

```
SiLuc sense (5'→3'):
                                         (SEQ ID NO: 4)
CUUACGCUGAGUACUUCGAdTdT SiLuc antisense (5'→3'):
                                         (SEQ ID NO: 5)
UCGAAGUACUCAGCGUAAGdTdT
```

Sequences of SiCont are as follows.

```
SiCont sense (5'→3'):
                                         (SEQ ID NO: 8)
GCACCUAUAACAACGGUAGdTdT SiCont antisense (5'→3'):
                                         (SEQ ID NO: 9)
CUACCGUUGUUAUAGGUGCdTdT
```

(2) Cell Line Culture

Huh7 (human hepatocellular carcinoma) cells obtained from ATCC was cultured in a RPMI 1640 medium (Hyclon) containing 10% fetal bovine serum (Invitrogen Co., Carlsbad, Calif., USA), 2 mmol/ml L-glutamine, 100 ug/ml penicillin and 100 units/ml of streptomycin at 37° C., 5% $CO_2$ incubator.

(3) Luciferase Assay $2 \times 10^5$ of Huh7 cells were inserted into each well of a 24 well plate and were grown. Transient transfection on the cells was performed using 2 ug of luciferase objective DNA and lipofectamin 2000 (Invitrogen Co., Carlsbad, Calif., USA). After 4 hours, lipofectamin 2000 was perfectly washed with PBS several times; siRNA of final concentration of 400 nm was treated in 500 ul of Opti-MEM (Invitrogen Co., Carlsbad, Calif., USA) and was reacted at 37° C. incubator for 16 hours. To terminate the reaction, cells were washed with PBS and proteins were lysed using Reporter Lysis Buffer (Progema Co., Madison, Wis., USA) solution and the luminescence was measured by luminometer (Turner BioSystem, Sunnyvale, Calif., USA) using luciferase reagent (Promega Co., Madison, Wis., USA). Efficacy of siRNA was corrected by Bradford protein assay.

Figure 57:
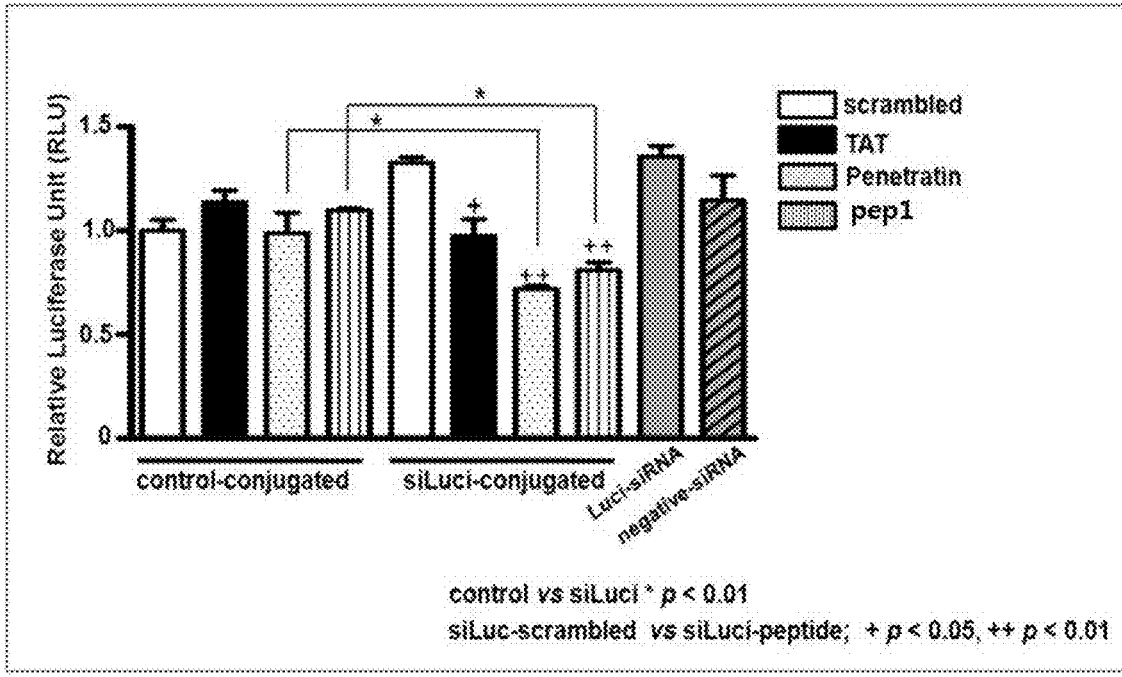
FIG. 57 represents the result of luciferase assay showing reduction in luciferase activity by proper entry of luciferase siRNA conjugated to pep1 into Huh7 cell line

To verify cell penetrating property of pep1, siRNA for luciferase purpose was produced produced and luciferase activation was measured using Huh7 (human hepatocelular carcinoma) cells and CHO cell line. The result verified that activation of penetratine and pep1 in siRNA combined with luciferase was reduced approx. 28%, 20% compared with penetratin and pep1 in siRNA combined with control in Huh cell line. In contrast to this, no significant difference in activation of was observed when scrambled and TAT in siRNA which was combined with luciferase and control. Also, when comparing luciferase activation between Tat and scrambled combined with luciferase and siRNA of pentratin and pep1, 27%, 55%, 40% of activation suppression was observed respectively (FIG. 57)

Figure 58:
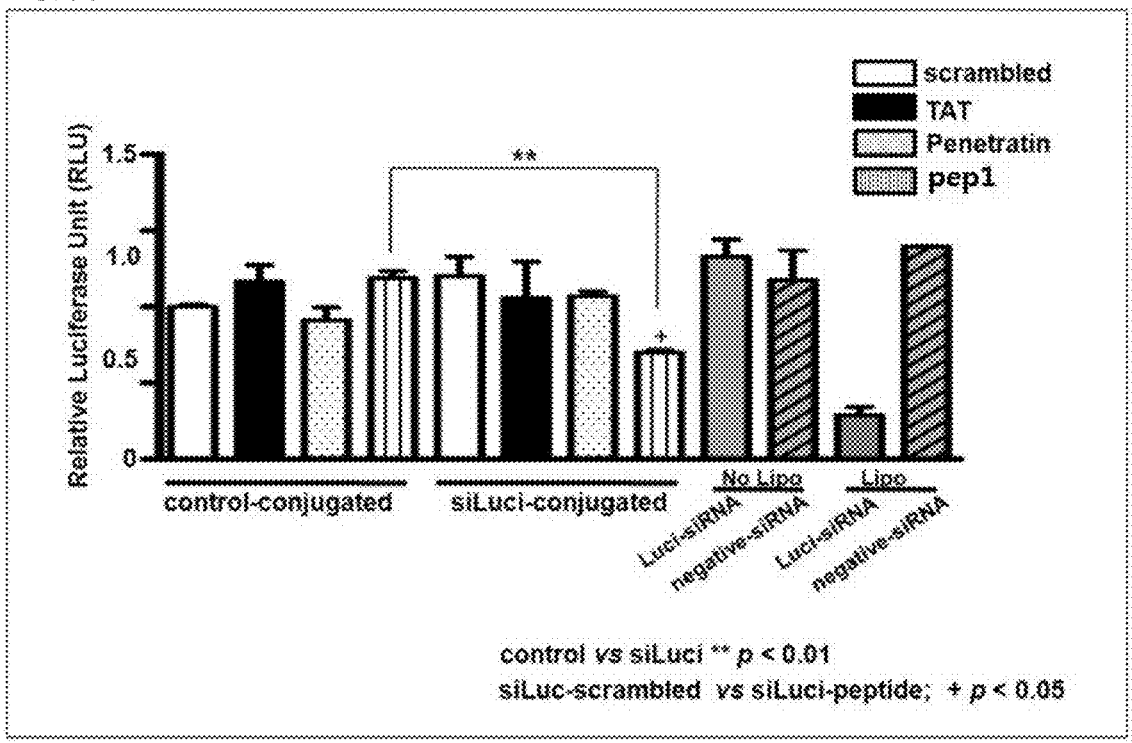
FIG. 58 represents the result of luciferase assay showing reduction in luciferase activity by proper entry of luciferase siRNA conjugated to pep1 in CHO cell line.

Unlike the other siRNA, siRNA conjugated with pep1 showed about 30% inhibition of luciferase activity in CHO cell. Thus, cell penetrating ability of pep 1 could be confirmed by observing inhibition luciferase activity using siRNA. (FIG. 58).

(4) Flow Cytometry Analysis on Transport Ability of siRNA siRNA sequences used in the experiment target HBx DNA and combined siHBV, sence-5' GAG GAC UCU UGG ACU CUC A dTdT-3' (SEQ ID NO: 3), antisense-5' UGA GAG UCC AAG AGUC CCU C dTdT-3')3' (SEQ ID NO: 13) with fluorescein. siRNA synthesis was performed by BIONEER, Korea, and the synthesized siRNA was purified by HPLC.

Figure 56:
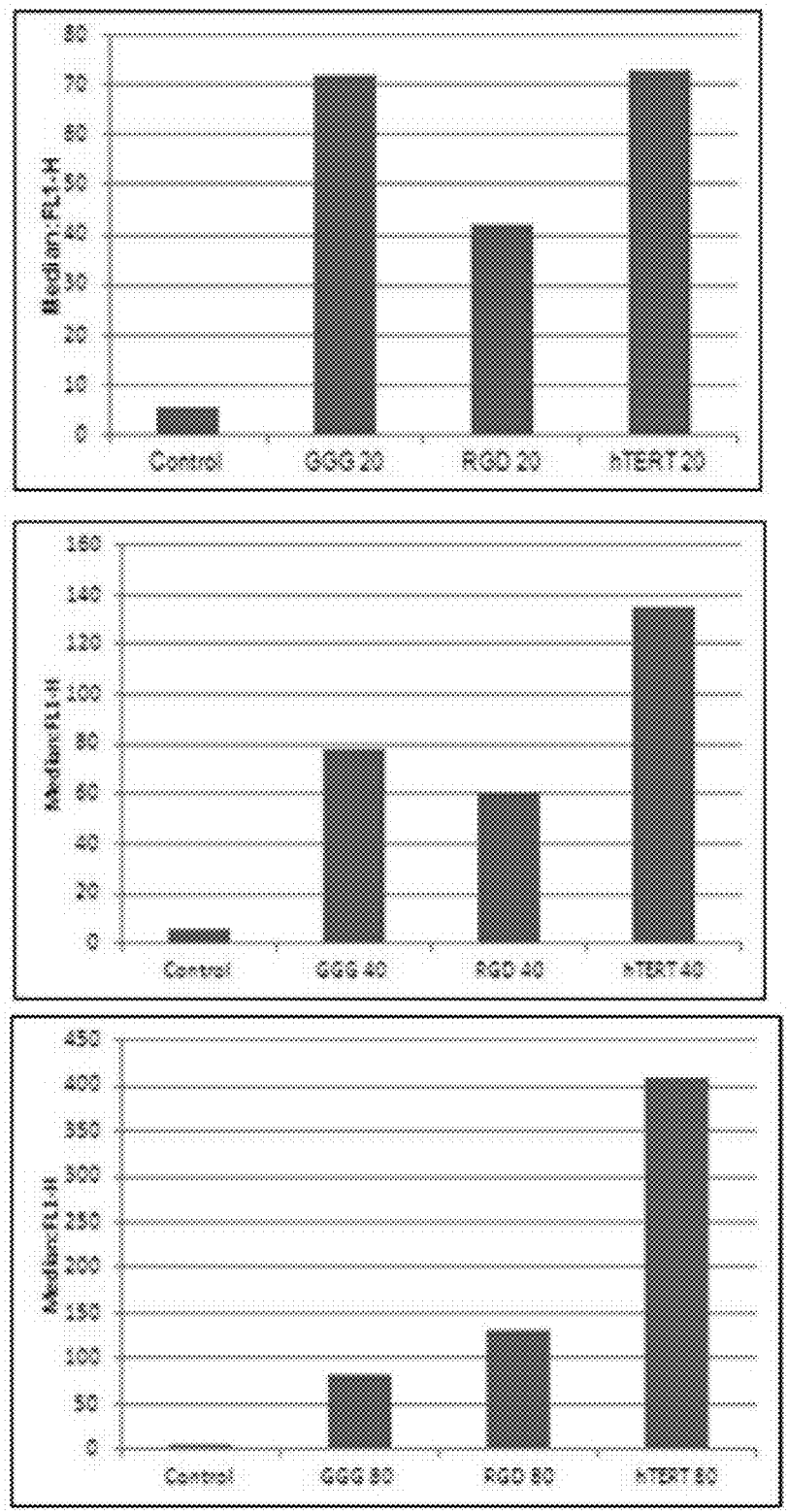
FIG. 56 represents the result of the degree of cellular uptake of siRNA by poly-lysine-pep1-FITC. combined with Poly-lysine-pep1-FITC to deliver into the cell.

$1 \times 10^5$ of HepG2 was cultured in each well of 24-well plate a day before and the medium was replaced with Opti-MEM. 4 hours after cell culture, FITC-labeled siRNA (siHBV) and the peptide of each molar ratio was added and mixed with 300 ul of Opti-MEM to produce the complex. siRNA was inserted to have a final concentration of 10 uM and was cultured at 37° C., 5% $CO_2$ for an hour. Trypsin was treated and was on standby in room temperature for 5 mins, and washed with PBS three times. 500 ul of FACS buffer was injected into each well and fluorescence substances other than cells were removed by repeating centrifugation three times at 300 rpm and 4° C. Total of 10,000 cells of FITC fluorescence were measured by flow cytometry (BD FACSCalibur System; Becton Dickinson, France). The result of cellular uptake analysis by flow cytometry verified that hTERT-pk sowed FITC-labeled siRNA cellular uptake 2.5 times higher than control group (RGD-pK, GGG-pK) at a concentration of above 20 molar ratio (FIG. 56).

Example 6: Local Transport Ability of CPP-FITC Conjugate to Mitochondria

1. Microscope Analysis
(1) Cell Line Culture

MCH7 (Human breast adenocarcinoma) adherent cell line obtained from ATCC was was used. The cell line was cultured in a RPMI 1640 medium (Sigma) containing 10% fetal bovine serum (Invitrogen, USA), 100 µg/ml penicillin, 100 units/ml streptomycin at 37° C., 5% $CO_2$ incubator.

A conjugate of FITC combined to C-terminal of peptide (SEQ ID NO:1) was manufactured as described in above Example 2.

(2) Confocal Microscope Analysis

Above cell line was divided to occupy 50% of 2-chamber slide glicer (NUNC, Lab Tek) surface and was cultured at 37° C., 5% $CO_2$ incubator for 12 hours. The medium was then removed and washed with PBS once and was cultured in 1 ml of OPTI-MEM (Sigma) for an hour and starvation was induced. 100 uM of a conjugate which FITC was combined to C-terminal of the peptide (SEQ ID NO: 1) was added to each chamber to become 50 µl(10 µM) and was cultured at 37° C., 5% $CO_2$ incubator for 2 hours.

The medium was then removed and washed with PBS (Phosphate buffered saline, ph 7.4) three times. At each chamber, 0.5 mL of 4% Paraformadehyde (PFA) was added and was fixed in room temperature for 20 mins. The cells were washed with 1×PBS and washed with 4% PFA twice swiftly.

Above cells were treated with 500 nM of TO-PRO-3 Iodide 642/661 nm (Invitrogen) and dyed the nucleus of cells in room temperature for 10 mins. Mitochondria were dyed with 250 nM of mototracker deep red FM 644/655 nm (Invitrogen) after treating them in room temperature for 15 mins. Solution was removed and the cells were washed with 1×PBS three times and plastic chamber was removed. After removing the chamber, VECTASHIELD mounting medium (Vector Laboratories) was dropped on a slide, slide glass was covered and confocal laser scanning system was performed avoiding light at FITC was measured at a wavelength of 488 nm with TO-PROR-3 Iodide (Invitrogen) and mitotrackerR deep red (Invitrogen) was measured at a wavelength of 633 nm.

Figure 59:
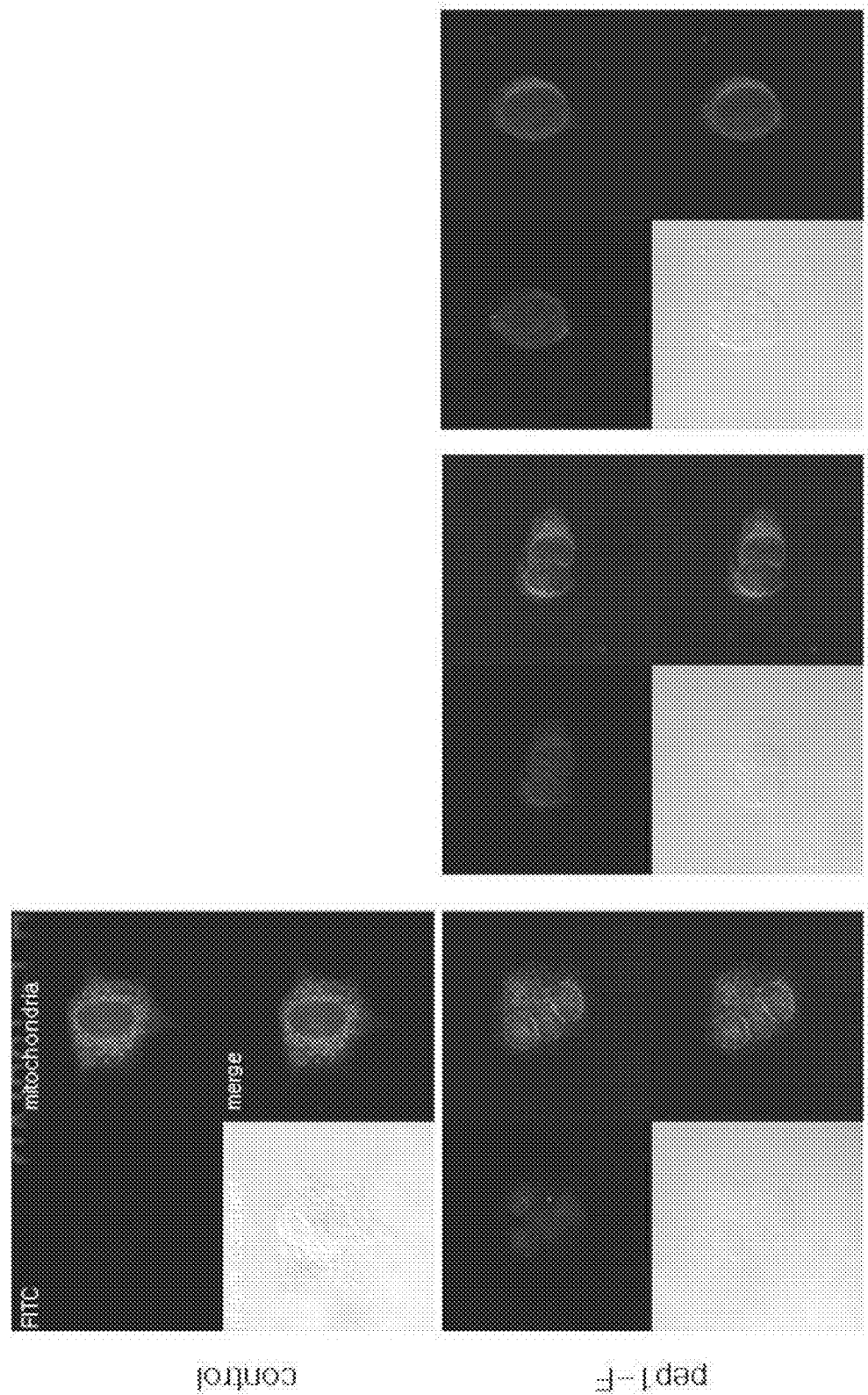
FIG. 59 is a diagram which represents the result of cellular localization of pep1-FITC conjugate with mitochondrial localization markers, Mitotrackers® with deep red FM 644/665 nm (Invitrogen) (A) Treatment of pep1-GFP conjugate in MCF-7 cells only (B) Treatment of mitochondrial localization marker, Mitotrackers® deep red FM 644/665 nm (Invitrogen) only (c) Phase contrast of cell, (D), a combined diagram of A and B.

The results are shown in FIG. 59. The results of dying a conjugate with FITC combined combined at C-terminal of the peptide (SEQ ID NO: 1) and mitochondria localization markers, Mototracker® deep red FM 644/655 nm (invitrogen), are (A) Single treatment of a conjugate with FITC combined at C-terminal of the peptide (SEQ ID NO: 1) in MCF cell, (B) single treatment of mitochondrial localization marker, mototracker deep red FM 644/665 nm (Invitrogen) (c) Phase contrast of cells, (D) Combination of images of A and B. With these results, it can be verified that telomerase derived peptide is localized within mitochondria.

2. Antibodies Combination

A pep-GFP conjugate manufactured according to methods described in Example 5. 1(1), was treated in $2\times10^7$ of MCF7 (Human breast adenocarcinoma) adherent cell line obtained from ATCC and the western blot was performed with mitochondrial hsp70 antibody. After treatment of GFP only, treatment of 1 lmer-GFP, treatment of ccg-GFP and Western blot analysis with hsp70 antibody was performed as examples of a comparison. Specifically, western blot analysis was performed as method described below.

$2\times10^7$ of MCF cell line was prepared and mitochondria was separated using Mitochondrial separation kit (Themo science, #89874) according to the corresponding protocol. Specifically, 800 ul of Reagent A was added to cell pellet, and was vortexed at a medium velocity for 5 seconds. After then, cells were placed in ice for 2 minutes and cell suspension was moved to a Dounce tissue grinder and the suspension was grinded on ice. Lysed cells were then moved to the original tube. 800 ul of Reagent C was added to the original tube and rinsed the grinder with 200 ul of Reagent A. After gently mixing, 700 g of the cells were centrifugated for 10 mins. The supernatant was moved to a new test tube, and centrifugated again at 3,000 g for 15 mins. The supernatant was discarded and 500 ul of Reagent C was added to the pellet containing mitochondria and centrifugated at 12,000 g for 5 mins. The supernatant was discarded and the pellet was placed in ice. 100 ul of buffer produced by adding 2% CHAPS to TBS (25 mM Tris, 0.15 M NaCl, pH 7.2) was vortexed for a minute. The buffer was centrifugated at 12,000 g for 2 mins, the soluble mitochondria protein was immunoprecipitated with test proteins as below.

The test proteins are pep1-GFP conjugate manufactured as described in Example 5. 1(1), 5. 1(1), GFP, 11mer-GFP, ccg-GFP were used as control. 11mer-GFP is a conjugate of 11mer protein combined with GFP wherein 11mer protein consists of 11 amino acids derived from HBV. Ccg is replication origin of Hepatitis B virus.

Figure 60:
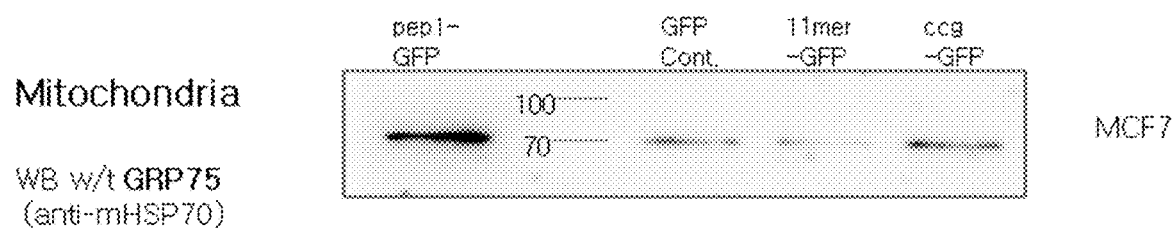
FIG. 60 represents the result of western blot analysis of pep1-GFP conjugate with mitochondrial hsp70 antibody; wherein the conjugate was treated with MCF7 (Human breast adenocarcinoma) cell line.
Figure 61:
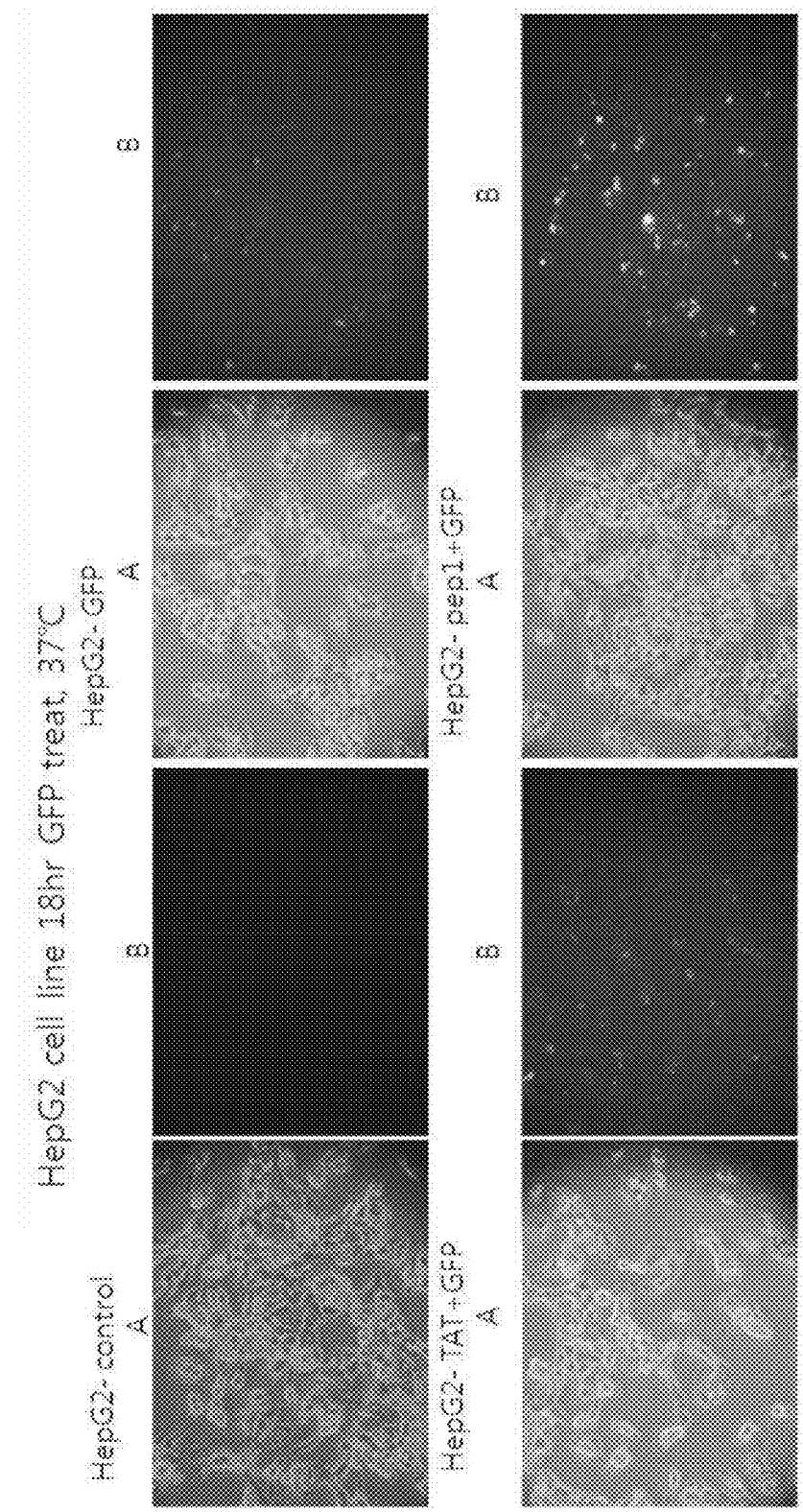
FIG. 61 is a diagram representing cellular uptake of pep1-GFP in HepG2 cell line.

To attach each of above test proteins and control protein to the resin, 6× His labeled cobalt resin was prepared (Prod. #89964, Thermo Scientific, UL, USA). 50-100 µl of the resin was added to a column and washed with 500 µl of washing buffer five times. Each expression protein was added to the column, was left by mixing at 4° C. for 30 min to 1 hour. After then, 500 µl of expression protein-resin polymer was washed with washing buffer for 5 times. The prepared mitochondria supernatant prepared above was added here and left overnight at 4° C. by stirring. On the next day, the resin was washed with the same method, the resin was eluted by adding 200 µl of elution buffer. The result is shown in the FIG. 60. The result verified that hsp70 antibody of mitochondria combine only to pep1-GFP.

The invention claimed is:

1. A conjugate of a carrier peptide and an active ingredient,
wherein the carrier peptide is an isolated peptide 16 amino acids in length and consists of the amino acid sequence of SEQ ID NO: 1;
wherein the carrier peptide and the active ingredient are connected via a covalent bond, or via a linker;
and the active ingredient is not telomerase or a fragment thereof.

2. The conjugate according to claim 1, wherein the active ingredient is a protein.

3. The conjugate according to claim 1, wherein the active ingredient is connected to the C-terminus of the carrier peptide.

4. A composition comprising the conjugate according to claim 1.

5. The composition according to claim 4, wherein the active ingredient is for treatment of disease, and the composition is a pharmaceutical composition.

6. A mitochondria targeting delivery system for an active ingredient,
wherein the delivery system comprises the conjugate according to claim 1, and
wherein the carrier peptide is a peptide that moves into a mitochondria locally and delivers the active ingredient to the mitochondria.

7. A composition for modulating mitochondria activity,
wherein the composition comprises the conjugate according to claim 1,
wherein the carrier peptide is a peptide that moves into a mitochondria locally and delivers the active ingredient to the mitochondria.

8. The conjugate according to claim 2, wherein the protein is a cytokine, antibody, fragment of antibody, therapeutic enzyme, soluble receptor, or ligand.

9. The conjugate according to claim 2, wherein the protein is an antibody or a fragment of antibody.

10. The conjugate according to claim 2, wherein the protein is an enzyme or enzyme inhibitor.

11. The conjugate according to claim 2, wherein the protein is a soluble receptor or ligand.

12. The conjugate according to claim 2, wherein the protein is a vaccine.

13. The conjugate according to claim 2, wherein the protein is a signal transfer protein.

14. The conjugate according to claim 2, wherein the protein is a hormone or hormone analogue.

15. The conjugate according to claim 2, wherein the linker is a Hynic linker.

16. The conjugate according to claim 1, wherein more than one carrier peptide are connected to one active ingredient.

* * * * *

SEQUENCE LISTING

```
<160> NUMBER OF SEQ ID NOS: 13

<210> SEQ ID NO 1
<211> LENGTH: 16
<212> TYPE: PRT
<213> ORGANISM: Homo sapiens

<400> SEQUENCE: 1

Glu Ala Arg Pro Ala Leu Leu Thr Ser Arg Leu Arg Phe Ile Pro Lys
1               5                   10                  15
```

<210> SEQ ID NO 2
<211> LENGTH: 1132
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln

-continued

```
                370                 375                 380
Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
                420                 425                 430

Gly Ser Val Ala Ala Pro Glu Glu Asp Thr Asp Pro Arg Arg Leu
                435                 440                 445

Val Gln Leu Leu Arg Gln His Ser Ser Pro Trp Gln Val Tyr Gly Phe
                450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
                515                 520                 525

Val Pro Ala Ala Glu His Arg Leu Arg Glu Glu Ile Leu Ala Lys Phe
                530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
                595                 600                 605

His Arg Glu Ala Arg Pro Ala Leu Leu Thr Ser Arg Leu Arg Phe Ile
                610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
                660                 665                 670

Pro Gly Leu Leu Gly Ala Ser Val Leu Gly Leu Asp Asp Ile His Arg
                675                 680                 685

Ala Trp Arg Thr Phe Val Leu Arg Val Arg Ala Gln Asp Pro Pro Pro
                690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
                755                 760                 765

Leu Gln Pro Tyr Met Arg Gln Phe Val Ala His Leu Gln Glu Thr Ser
                770                 775                 780

Pro Leu Arg Asp Ala Val Val Ile Glu Gln Ser Ser Ser Leu Asn Glu
785                 790                 795                 800
```

Ala Ser Ser Gly Leu Phe Asp Val Phe Leu Arg Phe Met Cys His His
            805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
            835                 840                 845

Met Glu Asn Lys Leu Phe Ala Gly Ile Arg Arg Asp Gly Leu Leu Leu
            850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
            885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
            915                 920                 925

Pro Trp Cys Gly Leu Leu Leu Asp Thr Arg Thr Leu Glu Val Gln Ser
            930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Lys Leu Phe Gly
            965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
            995                 1000                1005

Ala Tyr Arg Phe His Ala Cys Val Leu Gln Leu Pro Phe His Gln
            1010                1015                1020

Gln Val Trp Lys Asn Pro Thr Phe Phe Leu Arg Val Ile Ser Asp
            1025                1030                1035

Thr Ala Ser Leu Cys Tyr Ser Ile Leu Lys Ala Lys Asn Ala Gly
            1040                1045                1050

Met Ser Leu Gly Ala Lys Gly Ala Ala Gly Pro Leu Pro Ser Glu
            1055                1060                1065

Ala Val Gln Trp Leu Cys His Gln Ala Phe Leu Leu Lys Leu Thr
            1070                1075                1080

Arg His Arg Val Thr Tyr Val Pro Leu Leu Gly Ser Leu Arg Thr
            1085                1090                1095

Ala Gln Thr Gln Leu Ser Arg Lys Leu Pro Gly Thr Thr Leu Thr
            1100                1105                1110

Ala Leu Glu Ala Ala Ala Asn Pro Ala Leu Pro Ser Asp Phe Lys
            1115                1120                1125

Thr Ile Leu Asp
            1130

<210> SEQ ID NO 3
<211> LENGTH: 48
<212> TYPE: DNA
<213> ORGANISM: Homo sapiens

<400> SEQUENCE: 3
gaagcgcgcc cggcgctgct gaccagccgc ctgcgcttta ttccgaaa        48

<210> SEQ ID NO 4

<211> LENGTH: 21
<212> TYPE: RNA
<213> ORGANISM: Artificial Sequence
<220> FEATURE:
<223> OTHER INFORMATION: siRNA sense
<220> FEATURE:
<221> NAME/KEY: variation
<222> LOCATION: (20)..(21)
<223> OTHER INFORMATION: n is deoxythymidine (dT)
<220> FEATURE:
<221> NAME/KEY: misc_feature
<222> LOCATION: (20)..(21)
<223> OTHER INFORMATION: n is a, c, g, or u

<400> SEQUENCE: 4
cuuacgcuga guacuucgan n                                                   21

<210> SEQ ID NO 5
<211> LENGTH: 21
<212> TYPE: RNA
<213> ORGANISM: Artificial Sequence
<220> FEATURE:
<223> OTHER INFORMATION: siRNA antisense
<220> FEATURE:
<221> NAME/KEY: variation
<222> LOCATION: (20)..(21)
<223> OTHER INFORMATION: n is deoxythymidine (dT)
<220> FEATURE:
<221> NAME/KEY: misc_feature
<222> LOCATION: (20)..(21)
<223> OTHER INFORMATION: n is a, c, g, or u

<400> SEQUENCE: 5
ucgaaguacu cagcguaagn n                                                   21

<210> SEQ ID NO 6
<211> LENGTH: 239
<212> TYPE: PRT
<213> ORGANISM: Artificial Sequence
<220> FEATURE:
<223> OTHER INFORMATION: Green Fluorescent Protein

<400> SEQUENCE: 6

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser 165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 7
<211> LENGTH: 720
<212> TYPE: DNA
<213> ORGANISM: Artificial Sequence
<220> FEATURE:
<223> OTHER INFORMATION: Green Fluorescent Protein

<400> SEQUENCE: 7
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctgggggcac     420 aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720

<210> SEQ ID NO 8
<211> LENGTH: 21
<212> TYPE: RNA
<213> ORGANISM: Artificial Sequence
<220> FEATURE:
<223> OTHER INFORMATION: siCont sense
<220> FEATURE:
<221> NAME/KEY: variation
<222> LOCATION: (20)..(21)
<223> OTHER INFORMATION: n is deoxythymidine (dT)
<220> FEATURE:
<221> NAME/KEY: misc_feature
<222> LOCATION: (20)..(21)
<223> OTHER INFORMATION: n is a, c, g, or u

<400> SEQUENCE: 8
gcaccuauaa caacgguagn n                                                21

<210> SEQ ID NO 9
<211> LENGTH: 21
<212> TYPE: RNA
<213> ORGANISM: Artificial Sequence
<220> FEATURE:
<223> OTHER INFORMATION: siCont antisense
<220> FEATURE:
<221> NAME/KEY: variation
<222> LOCATION: (20)..(21)
<223> OTHER INFORMATION: n is deoxythymidine (dT)

```
<220> FEATURE:
<221> NAME/KEY: misc_feature
<222> LOCATION: (20)..(21)
<223> OTHER INFORMATION: n is a, c, g, or u

<400> SEQUENCE: 9
cuaccguugu uauaggugcn n                                              21

<210> SEQ ID NO 10
<211> LENGTH: 11
<212> TYPE: PRT
<213> ORGANISM: Human immunodeficiency virus

<400> SEQUENCE: 10

Tyr Gly Arg Lys Lys Arg Arg Gln Arg Arg Arg
1               5                   10

<210> SEQ ID NO 11
<211> LENGTH: 33
<212> TYPE: DNA
<213> ORGANISM: Human immunodeficiency virus

<400> SEQUENCE: 11
tatggtcgta aaaacgtcg tcaacgtcgt cgt                                  33

<210> SEQ ID NO 12
<211> LENGTH: 21
<212> TYPE: RNA
<213> ORGANISM: Artificial Sequence
<220> FEATURE:
<223> OTHER INFORMATION: siRNA sense
<220> FEATURE:
<221> NAME/KEY: variation
<222> LOCATION: (20)..(21)
<223> OTHER INFORMATION: n is deoxythymidine (dT)
<220> FEATURE:
<221> NAME/KEY: misc_feature
<222> LOCATION: (20)..(21)
<223> OTHER INFORMATION: n is a, c, g, or u

<400> SEQUENCE: 12
gaggacucuu ggacucucan n                                              21

<210> SEQ ID NO 13
<211> LENGTH: 21
<212> TYPE: RNA
<213> ORGANISM: Artificial Sequence
<220> FEATURE:
<223> OTHER INFORMATION: siRNA antisense
<220> FEATURE:
<221> NAME/KEY: variation
<222> LOCATION: (20)..(21)
<223> OTHER INFORMATION: n is deoxythymidine (dT)
<220> FEATURE:
<221> NAME/KEY: misc_feature
<222> LOCATION: (20)..(21)
<223> OTHER INFORMATION: n is a, c, g, or u

<400> SEQUENCE: 13
ugagagucca agaguccucn n                                              21
```